(12) United States Patent
Mahfouz

(10) Patent No.: US 10,130,478 B2
(45) Date of Patent: Nov. 20, 2018

(54) ETHNIC-SPECIFIC ORTHOPAEDIC IMPLANTS AND CUSTOM CUTTING JIGS

(71) Applicant: ZIMMER INC., Warsaw, IN (US)

(72) Inventor: Mohamed Rashwan Mahfouz, Knoxville, TN (US)

(73) Assignee: ZIMMER, INC., Warsaw, IN (US)

(*) Notice: Subject to any disclaimer, the term of this patent is extended or adjusted under 35 U.S.C. 154(b) by 55 days.

(21) Appl. No.: 14/734,491

(22) Filed: Jun. 9, 2015

(65) Prior Publication Data

US 2016/0000571 A1  Jan. 7, 2016

Related U.S. Application Data

(60) Division of application No. 13/268,262, filed on Oct. 7, 2011, now Pat. No. 9,078,755, which is a
(Continued)

(51) Int. Cl.
  *A61F 2/38*     (2006.01)
  *A61B 17/14*   (2006.01)
(Continued)

(52) U.S. Cl.
  CPC ............ *A61F 2/3859* (2013.01); *A61B 17/14* (2013.01); *A61B 17/155* (2013.01);
(Continued)

(58) Field of Classification Search
  CPC .......... A61F 2/38; A61F 2/3859; A61F 2/389; A61F 2002/3863; A61F 2002/30939; A61F 2/3094; A61F 2/30942; A61F 2002/30943; A61F 2002/30945; A61F 2002/30947; A61F 2002/30948; A61F 2002/3095; A61F 2002/30952; A61F 2002/30955; A61F 2002/30962; A61F 2002/30968;
(Continued)

(56) References Cited

U.S. PATENT DOCUMENTS 4,841,975 A   6/1989  Woolson
4,888,021 A * 12/1989 Forte ...................... A61F 2/385
                                                  623/20.19
(Continued)

FOREIGN PATENT DOCUMENTS

AU   2004293091 A1   6/2005
AU   2004293104 A1   6/2005
(Continued)

OTHER PUBLICATIONS

Extended European Search Report, Application No. EP 12837887.4, dated Apr. 20, 2016.
(Continued)

*Primary Examiner* — Alvin Stewart
(74) *Attorney, Agent, or Firm* — Norton Rose Fulbright Canada LLP

(57) ABSTRACT

An orthopedic implant comprising: (a) a distal femoral component comprising a first condyle bearing surface having a first profile comprising at least three consecutive arcs of curvature; and (b) a proximal tibial component comprising a first condyle bearing surface having a second profile comprising at least three parallel arcs of curvature.

16 Claims, 74 Drawing Sheets

Related U.S. Application Data continuation-in-part of application No. 13/203,012, filed as application No. PCT/US2010/025466 on Feb. 25, 2010, now Pat. No. 8,989,460.

(60) Provisional application No. 61/530,177, filed on Sep. 1, 2011, provisional application No. 61/208,509, filed on Feb. 25, 2009, provisional application No. 61/222,560, filed on Jul. 2, 2009.

(51) Int. Cl.
*A61B 17/15* (2006.01)
*A61B 17/16* (2006.01)
*A61B 17/17* (2006.01)
*A61B 17/56* (2006.01)
*A61F 2/30* (2006.01)

(52) U.S. Cl.
CPC .......... *A61B 17/1626* (2013.01); *A61F 2/389* (2013.01); *A61B 17/1675* (2013.01); *A61B 17/1764* (2013.01); *A61B 2017/568* (2013.01); *A61F 2002/30952* (2013.01); *Y10T 29/49* (2015.01)

(58) Field of Classification Search
CPC .... A61F 2002/3097; A61F 2002/30971; A61F 17/155; A61F 17/1675; A61F 17/1764; A61F 2017/568; B33Y 80/00
See application file for complete search history.

(56) References Cited

U.S. PATENT DOCUMENTS

| | | | |
|---|---|---|---|
| 5,098,383 | A | 3/1992 | Hemmy et al. |
| 5,490,854 | A | 2/1996 | Fisher et al. |
| 5,609,643 | A | 3/1997 | Colleran et al. |
| 5,768,134 | A | 6/1998 | Swaelens et al. |
| 5,871,018 | A | 2/1999 | Delp et al. |
| 5,916,219 | A | 6/1999 | Matsuno et al. |
| 7,239,908 | B1 | 7/2007 | Alexander et al. |
| 7,269,241 | B2 | 9/2007 | Siltanen et al. |
| 7,357,057 | B2 | 4/2008 | Chiang |
| 7,468,075 | B2 | 12/2008 | Lang et al. |
| 7,510,557 | B1 | 3/2009 | Bonutti |
| 7,534,263 | B2 | 5/2009 | Burdulis |
| 7,618,451 | B2 | 11/2009 | Berez et al. |
| 7,634,119 | B2 | 12/2009 | Tsougarakis et al. |
| 7,717,956 | B2 | 5/2010 | Lang |
| 7,796,791 | B2 | 9/2010 | Tsougarakis et al. |
| 7,799,077 | B2 | 9/2010 | Lang et al. |
| 7,806,896 | B1 | 10/2010 | Bonutti |
| 7,806,897 | B1 | 10/2010 | Bonutti |
| 7,967,868 | B2 * | 6/2011 | White .................. A61B 17/154 623/20.35 |
| 7,981,158 | B2 | 7/2011 | Fitz et al. |
| 8,062,302 | B2 | 11/2011 | Lang et al. |
| 8,066,708 | B2 | 11/2011 | Lang et al. |
| 8,070,752 | B2 | 12/2011 | Metzger et al. |
| 8,077,950 | B2 | 12/2011 | Tsougarakis et al. |
| 8,083,745 | B2 | 12/2011 | Lang et al. |
| 8,092,465 | B2 | 1/2012 | Metzger et al. |
| 8,094,900 | B2 | 1/2012 | Steines et al. |
| 8,105,330 | B2 | 1/2012 | Fitz et al. |
| 8,122,582 | B2 | 2/2012 | Burdulis, Jr. et al. |
| 8,133,234 | B2 | 3/2012 | Meridew et al. |
| 8,160,345 | B2 * | 4/2012 | Pavlovskaia ........... B33Y 50/00 382/131 |
| 8,175,683 | B2 | 5/2012 | Roose |
| 8,221,430 | B2 | 7/2012 | Park et al. |
| 8,234,097 | B2 | 7/2012 | Steines et al. |
| 8,241,293 | B2 | 8/2012 | Stone et al. |
| 8,282,646 | B2 | 10/2012 | Schoenefeld et al. |
| 8,298,237 | B2 | 10/2012 | Schoenefeld |
| 8,337,501 | B2 | 12/2012 | Fitz et al. |
| 8,337,507 | B2 | 12/2012 | Lang et al. |
| 8,343,218 | B2 | 1/2013 | Lang et al. |
| 8,366,771 | B2 | 2/2013 | Burdulis et al. |
| 8,377,129 | B2 | 2/2013 | Fitz et al. |
| 8,439,926 | B2 | 5/2013 | Bojarski et al. |
| 8,460,304 | B2 | 6/2013 | Fitz et al. |
| 8,480,754 | B2 | 7/2013 | Bojarski et al. |
| 8,500,740 | B2 | 8/2013 | Bojarski et al. |
| 8,529,568 | B2 | 9/2013 | Bouadi |
| 8,529,630 | B2 | 9/2013 | Bojarski |
| 8,585,708 | B2 | 9/2013 | Fitz et al. |
| 8,545,569 | B2 | 10/2013 | Fitz et al. |
| 8,551,099 | B2 | 10/2013 | Lang |
| 8,551,102 | B2 | 10/2013 | Fitz et al. |
| 8,551,103 | B2 | 10/2013 | Fitz et al. |
| 8,551,169 | B2 | 10/2013 | Fitz et al. |
| 8,556,906 | B2 | 10/2013 | Fitz et al. |
| 8,556,907 | B2 | 10/2013 | Fitz et al. |
| 8,556,971 | B2 | 10/2013 | Lang |
| 8,556,983 | B2 * | 10/2013 | Bojarski ................ A61F 2/3859 606/86 R |
| 8,561,278 | B2 | 10/2013 | Fitz et al. |
| 8,562,611 | B2 | 10/2013 | Fitz et al. |
| 8,562,618 | B2 | 10/2013 | Fitz et al. |
| 8,568,479 | B2 | 10/2013 | Fitz et al. |
| 8,568,480 | B2 | 10/2013 | Fitz et al. |
| 8,617,172 | B2 | 12/2013 | Fitz et al. |
| 8,617,242 | B2 * | 12/2013 | Philipp ............... A61F 2/30756 623/18.11 |
| 8,623,026 | B2 | 1/2014 | Wong et al. |
| 8,634,617 | B2 | 1/2014 | Tsougarakis et al. |
| 8,638,998 | B2 | 1/2014 | Steines et al. |
| 8,641,716 | B2 | 2/2014 | Fitz et al. |
| 8,657,827 | B2 | 2/2014 | Fitz et al. |
| 8,682,052 | B2 | 3/2014 | Fitz et al. |
| 9,078,755 | B2 * | 7/2015 | Mahfouz ................ A61B 17/14 |
| 9,517,134 | B2 * | 12/2016 | Lang ................... A61F 2/30756 |
| 9,603,711 | B2 * | 3/2017 | Bojarski ............. A61F 2/30942 |
| 2002/0055692 | A1 | 5/2002 | Tanaka et al. |
| 2003/0040806 | A1 | 2/2003 | MacDonald |
| 2003/0055502 | A1 | 3/2003 | Lang et al. |
| 2003/0181831 | A1 | 9/2003 | Tanaka et al. |
| 2003/0216669 | A1 * | 11/2003 | Lang ................... A61B 5/4528 600/587 |
| 2004/0039259 | A1 | 2/2004 | Krause et al. |
| 2004/0068187 | A1 | 4/2004 | Krause et al. |
| 2004/0098132 | A1 | 5/2004 | Andriacchi et al. |
| 2004/0133276 | A1 | 7/2004 | Lang et al. |
| 2004/0138754 | A1 | 7/2004 | Lang et al. |
| 2004/0147927 | A1 * | 7/2004 | Tsougarakis ........ A61F 2/30756 606/53 |
| 2004/0153079 | A1 | 8/2004 | Tsougarakis et al. |
| 2004/0204644 | A1 | 10/2004 | Tsougarakis et al. |
| 2004/0204760 | A1 * | 10/2004 | Fitz .................... A61F 2/30756 623/14.12 |
| 2004/0236424 | A1 | 11/2004 | Berez et al. |
| 2005/0010444 | A1 | 1/2005 | Iliff |
| 2005/0197709 | A1 | 9/2005 | Schaefer et al. |
| 2005/0197814 | A1 | 9/2005 | Aram et al. |
| 2005/0234461 | A1 | 10/2005 | Burdulis et al. |
| 2005/0267584 | A1 * | 12/2005 | Burdulis, Jr. ....... A61F 2/30942 623/20.19 |
| 2006/0111722 | A1 | 5/2006 | Bouadi |
| 2006/0195198 | A1 | 8/2006 | James |
| 2007/0081706 | A1 | 4/2007 | Zhou et al. |
| 2007/0083266 | A1 | 4/2007 | Lang |
| 2007/0100462 | A1 | 5/2007 | Lang et al. |
| 2007/0118243 | A1 * | 5/2007 | Schroeder ............ G16H 50/50 700/118 |
| 2007/0156171 | A1 | 7/2007 | Lang et al. |
| 2007/0157783 | A1 | 7/2007 | Chiang |
| 2007/0168225 | A1 | 7/2007 | Haider et al. |
| 2007/0179626 | A1 | 8/2007 | de la Barrera et al. |
| 2007/0198022 | A1 | 8/2007 | Lang et al. |
| 2007/0226986 | A1 | 10/2007 | Park et al. |
| 2007/0233141 | A1 | 10/2007 | Park et al. |
| 2007/0233269 | A1 | 10/2007 | Steines et al. |
| 2007/0250169 | A1 | 10/2007 | Lang |

(56) References Cited

U.S. PATENT DOCUMENTS

| | | | |
|---|---|---|---|
| 2007/0255288 A1* | 11/2007 | Mahfouz | A61B 5/1075 606/102 |
| 2007/0276214 A1 | 11/2007 | Dachille et al. | |
| 2008/0058945 A1 | 3/2008 | Hajaj et al. | |
| 2008/0097187 A1 | 4/2008 | Gielen et al. | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0172125 A1 | 7/2008 | Ek | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0043556 A1 | 2/2009 | Axelson et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarksi et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0054572 A1 | 3/2010 | Tsougarakis et al. | |
| 2010/0082035 A1 | 4/2010 | Keefer | |
| 2010/0087829 A1 | 4/2010 | Metzger et al. | |
| 2010/0152741 A1 | 6/2010 | Park et al. | |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |
| 2010/0174376 A1 | 7/2010 | Lang et al. | |
| 2010/0185202 A1 | 7/2010 | Lester et al. | |
| 2010/0191244 A1 | 7/2010 | White et al. | |
| 2010/0212138 A1 | 8/2010 | Carroll et al. | |
| 2010/0217270 A1 | 8/2010 | Polinski et al. | |
| 2010/0217338 A1 | 8/2010 | Carroll et al. | |
| 2010/0228257 A1 | 9/2010 | Bonutti | |
| 2010/0234849 A1 | 9/2010 | Bouadi | |
| 2010/0256479 A1 | 10/2010 | Park et al. | |
| 2010/0262150 A1 | 10/2010 | Lian | |
| 2010/0274534 A1 | 10/2010 | Steines et al. | |
| 2010/0281678 A1 | 11/2010 | Burdulis, Jr. et al. | |
| 2010/0286700 A1 | 11/2010 | Snider et al. | |
| 2010/0298894 A1 | 11/2010 | Bojarski et al. | |
| 2010/0303313 A1 | 12/2010 | Lang et al. | |
| 2010/0303317 A1 | 12/2010 | Tsougarakis et al. | |
| 2010/0303324 A1 | 12/2010 | Lang et al. | |
| 2010/0305573 A1 | 12/2010 | Fitz | |
| 2010/0305574 A1 | 12/2010 | Fitz et al. | |
| 2010/0305708 A1 | 12/2010 | Lang et al. | |
| 2010/0305907 A1 | 12/2010 | Fitz et al. | |
| 2010/0329530 A1 | 12/2010 | Lang et al. | |
| 2011/0015636 A1 | 1/2011 | Katrana et al. | |
| 2011/0015637 A1 | 1/2011 | De Smedt et al. | |
| 2011/0015639 A1 | 1/2011 | Metzger et al. | |
| 2011/0022179 A1* | 1/2011 | Andriacchi | A61F 2/38 623/20.18 |
| 2011/0029091 A1 | 2/2011 | Bojarski et al. | |
| 2011/0029093 A1* | 2/2011 | Bojarski | A61F 2/30942 623/20.35 |
| 2011/0040168 A1 | 2/2011 | Arnaud et al. | |
| 2011/0054478 A1 | 3/2011 | Vanasse et al. | |
| 2011/0060341 A1 | 3/2011 | Angibaud et al. | |
| 2011/0066193 A1 | 3/2011 | Lang et al. | |
| 2011/0066245 A1 | 3/2011 | Lang et al. | |
| 2011/0071533 A1 | 3/2011 | Metzger et al. | |
| 2011/0071581 A1 | 3/2011 | Lang et al. | |
| 2011/0071645 A1 | 3/2011 | Bojarski et al. | |
| 2011/0071802 A1 | 3/2011 | Bojarski et al. | |
| 2011/0087332 A1 | 4/2011 | Bojarski et al. | |
| 2011/0092977 A1 | 4/2011 | Salehi et al. | |
| 2011/0093108 A1 | 4/2011 | Ashby et al. | |
| 2011/0106093 A1 | 5/2011 | Romano et al. | |
| 2011/0125275 A1 | 5/2011 | Lipman et al. | |
| 2011/0144760 A1 | 6/2011 | Wong et al. | |
| 2011/0160736 A1 | 6/2011 | Meridew et al. | |
| 2011/0160867 A1 | 6/2011 | Meridew et al. | |
| 2011/0166578 A1 | 7/2011 | Stone et al. | |
| 2011/0172672 A1 | 7/2011 | Dubeau et al. | |
| 2011/0184419 A1 | 7/2011 | Meridew et al. | |
| 2011/0196377 A1 | 8/2011 | Hodorek et al. | |
| 2011/0213368 A1 | 9/2011 | Fitz et al. | |
| 2011/0213373 A1 | 9/2011 | Fitz et al. | |
| 2011/0213374 A1 | 9/2011 | Fitz et al. | |
| 2011/0213376 A1 | 9/2011 | Maxson et al. | |
| 2011/0213377 A1 | 9/2011 | Lang et al. | |
| 2011/0213427 A1 | 9/2011 | Fitz et al. | |
| 2011/0213428 A1 | 9/2011 | Fitz et al. | |
| 2011/0213429 A1 | 9/2011 | Lang et al. | |
| 2011/0213430 A1 | 9/2011 | Lang et al. | |
| 2011/0213431 A1 | 9/2011 | Fitz et al. | |
| 2011/0214279 A1 | 9/2011 | Park et al. | |
| 2011/0218539 A1 | 9/2011 | Fitz et al. | |
| 2011/0218545 A1 | 9/2011 | Catanzarite et al. | |
| 2011/0218584 A1 | 9/2011 | Fitz et al. | |
| 2011/0224674 A1 | 9/2011 | White et al. | |
| 2011/0230888 A1 | 9/2011 | Lang et al. | |
| 2011/0238073 A1 | 9/2011 | Lang et al. | |
| 2011/0245835 A1 | 10/2011 | Dodds et al. | |
| 2011/0266265 A1* | 11/2011 | Lang | A61F 2/30756 219/121.72 |
| 2011/0295329 A1 | 12/2011 | Fitz et al. | |
| 2011/0295378 A1 | 12/2011 | Bojarski et al. | |
| 2011/0313423 A1 | 12/2011 | Lang et al. | |
| 2011/0313424 A1 | 12/2011 | Bono et al. | |
| 2011/0319897 A1 | 12/2011 | Lang et al. | |
| 2011/0319900 A1 | 12/2011 | Lang et al. | |
| 2012/0010711 A1 | 1/2012 | Antonyshyn et al. | |
| 2012/0029520 A1 | 2/2012 | Lang et al. | |
| 2012/0041445 A1 | 2/2012 | Roose et al. | |
| 2012/0041446 A1 | 2/2012 | Wong et al. | |
| 2012/0065640 A1 | 3/2012 | Metzger et al. | |
| 2012/0066892 A1 | 3/2012 | Lang et al. | |
| 2012/0071881 A1 | 3/2012 | Lang et al. | |
| 2012/0071882 A1 | 3/2012 | Lang et al. | |
| 2012/0071883 A1 | 3/2012 | Lang et al. | |
| 2012/0072185 A1 | 3/2012 | Lang et al. | |
| 2012/0078254 A1 | 3/2012 | Ashby et al. | |
| 2012/0078258 A1 | 3/2012 | Lo et al. | |
| 2012/0078259 A1 | 3/2012 | Meridew | |
| 2012/0093377 A1 | 4/2012 | Tsougarakis et al. | |
| 2012/0101503 A1 | 4/2012 | Lang et al. | |
| 2012/0109138 A1 | 5/2012 | Meridew et al. | |
| 2012/0116203 A1 | 5/2012 | Vancraen et al. | |
| 2012/0116562 A1 | 5/2012 | Agnihotri et al. | |
| 2012/0123422 A1 | 5/2012 | Agnihotri et al. | |
| 2012/0123423 A1 | 5/2012 | Fryman | |
| 2012/0130382 A1 | 5/2012 | Iannotti et al. | |
| 2012/0130687 A1* | 5/2012 | Otto | A61B 5/103 703/1 |

(56) References Cited

U.S. PATENT DOCUMENTS

| | | |
|---|---|---|
| 2012/0141034 A1 | 6/2012 | Iannotti et al. |
| 2012/0143197 A1 | 6/2012 | Lang et al. |
| 2012/0151730 A1* | 6/2012 | Fitz .................... A61B 5/4528 29/407.01 |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0265496 A1* | 10/2012 | Mahfouz .................... A61B 17/14 703/1 |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1* | 1/2013 | Fitz .................... A61B 5/4528 606/1 |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1* | 4/2013 | Fitz .................... A61B 5/4528 29/407.09 |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0226305 A1* | 8/2013 | Donno .................... A61F 2/3859 623/20.35 |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2016/0000571 A1* | 1/2016 | Mahfouz .................... A61B 17/14 623/20.32 |
| 2017/0252879 A1* | 9/2017 | Sanford .................... A61B 17/00 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |

(56) References Cited

FOREIGN PATENT DOCUMENTS

| | | |
|---|---|---|
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2002085435 | 3/2002 |
| JP | 2004202126 | 7/2004 |
| JP | 2006510403 A | 3/2006 |
| JP | 2006263241 | 10/2006 |
| JP | 2007514470 | 6/2007 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012518519 | 8/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109467 | 9/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 | 9/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010099359 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011/071979 | 6/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |

(56) References Cited

FOREIGN PATENT DOCUMENTS

| WO | 2014008444 A1 | 1/2014 |
|----|---------------|--------|
| WO | 2014035991 A1 | 3/2014 |
| WO | 2014047514 A1 | 3/2014 |

OTHER PUBLICATIONS

Taylor et al, "Computer-Integrated Surgery, Technology and Clinical Applications", The MIT Press, Cambridge, MA, London, UK, pp. 451-463, 1995.

Hofmann et al, "Natural-Knee II System", Intermedics Orthopedics, Austin, TX, 1995.

Mahfouz et al., "Three-dimensional Morphology of the Knee Reveals Ethnic Differences", Clin. Orthop. Relat. Res., Vol. 470, No. 1, Jan. 2012, pp. 172-185.

Dennis et al., "Multicenter Determination of In Vivo Kinematics After Total Knee Arthroplasty" Coventry Award Paper, Clinical Orthopaedics and Related Research, No. 416, pp. 37-57, c 2003 Lippincott Williams & Wilkins, Inc., USA.

Mahfouz et al., "A Robust Method for Registration of Three-Dimensional Knee Implant Models to Two-Dimensional Flouroscopy Images", IEEE Transactions on Medical Imaging, vol. 22, No. 12, Dec. 2003, c 2003 IEEE, USA.

Mahfouz et al., "Automatic Methods for Characterization of Sexual Dimorphism of Adult Femora: Distal Femur", Computer Methods in Biomechanics and Biomedical Engineering, 2007, iFirst Article, 1-10, c 2007 Taylor & Francis, GB.

Mahfouz et al., "Patella Sex Determination by 3D Statistical Shape Models and Nonlinear Classifiers", Forensic Science International, FSI-5154, pp. 1-10, c 2007 Elsevier Ireland Ltd., IE.

Merkl et al., "Unsupervised Three-Dimensional Segmentation of Medical Images Using an Anatomical Bone Atlas", Published in Biomedical Conference in Singapore, Dec. 2005, University of Tennessee/Department of Mechanical, Aerospace and Biomedical Engineering, Knoxville, TN, USA.

International Search Report and Written Opinion dated Jul. 1, 2010 for PCT/US2010/025466.

International Preliminary Report on Patentability dated Jun. 7, 2011 for PCT/US2010/025466.

International Search Report and Written Opinion dated Apr. 23, 2010 for PCTUS2010/025467.

International Preliminary Report on Patentability dated Oct. 11, 2011 for PCTUS2010/025467.

Supplementary European Search Report, Application No. EP 10746865 dated Jun. 17, 2015.

Shapiro et al., "Similarity-Based Retrieval for Biomedical Applications", Studies in Computational Intelligence, Springer, 73, pp. 355-387, 2008.

\* cited by examiner

ETHNIC-SPECIFIC ORTHOPAEDIC IMPLANTS AND CUSTOM CUTTING JIGS

CROSS REFERENCE TO RELATED APPLICATIONS

The present application is a divisional of U.S. patent application Ser. No. 13/268,262 filed Oct. 7, 2011 which claims the benefit of U.S. Provisional Patent Application Ser. No. 61/530,177 filed Sep. 1, 2011 and is a continuation-in-part of U.S. Non-provisional patent application Ser. No. 13/203,012 filed Aug. 24, 2011, which is a 371 application of PCT/US2010/25466 filed Feb. 25, 2010 and claims the benefit of U.S. Provisional Patent Application Ser. No. 61/208,509 filed Feb. 25, 2009 and U.S. Provisional Patent Application Ser. No. 61/222,560 filed Jul. 2, 2009, the disclosure of each of which is incorporated herein by reference.

FIELD OF THE INVENTION

The present disclosure relates to orthopaedic implants and orthopaedic cutting jigs and, more specifically, to methods and devices utilized to design orthopaedic implants and orthopaedic jigs for use with joint replacement and revision procedures.

INTRODUCTION TO THE INVENTION

Of primary interest to the knee prosthetics industry is the analysis of the intrinsic shape differences of the knee joint between different ethnic populations for development of implantable orthopaedic devices. The study presented is thus three-fold: by developing a novel automatic feature detection algorithm, a set of automated measurements can be defined based on highly morphometric variant regions, which then allows for a statistical framework when analyzing different populations' knee joint differences.

Ethnic differences in lower limb morphology focus on the differences between Asian and Western populations because this variation is of great import in implant design. For example, Chinese femora are more anteriorly bowed and externally rotated with smaller intramedullary canals and smaller distal condyles than Caucasian femora. Likewise, Caucasian femora are larger than Japanese femora in terms of length and distal condyle dimensions. Ethnic differences in proximal femur bone mineral density (BMD) and hip axis length also exists between American Blacks and Whites. The combined effects of higher BMD, shorter hip axis length, and shorter intertrochanteric width may explain the lower prevalence of osteoporotic fractures in Black women compared to their White counterparts. Similarly, elderly Asian and Black men have been found to have thicker cortices and higher BMD than White and Hispanic men, which may contribute to greater bone strength in these ethnic groups. In general, Blacks have thicker bone cortices, narrower endosteal diameters, and greater BMD than Whites. Interestingly, though, these traits are most pronounced in African Blacks compared to American Blacks.

The following analysis considers metric and geometric morphometric variation in the lower limb of modern American Blacks, Whites and East Asians. Three-dimensional statistical bone atlases are used in order to facilitate rapid and accurate data collection in the form of automated measurements, as well as measurements used in biomedical studies and some newly-devised measurements. The shape analysis is conducted with a statistical treatment combining Principal Components Analysis (PCA) and Multiple Discriminant Analysis; metric analysis is performed using t-tests, power tests, and linear discriminant analysis in the Implant Design and Analysis Suite (see co-pending U.S. patent application Ser. No. 12/673,640, entitled, IMPLANT DESIGN ANALYSIS SUITE, the disclosure of which is incorporated herein by reference) system. The results of these analyses add to the existing knowledge of morphological variation in the knee joint and provide useful information that can be extracted for knee prosthesis design as will be outlined in the remainder of this disclosure.

The instant approach may make use of Computed Tomography (CT) scans for data collection combined with the computational power and precision offered by statistical bone atlases. An exemplary data set that comprises 943 male and female individuals (81.5% American White, 9% American Black and 9.5% East Asians, where the overall male/female ratio 65/35%) was scanned using CT scans. Only normal femora and tibia were included in this study; femora or tibia with severe osteophytes and other abnormalities were specifically excluded. Only one femur and tibia was chosen from each individual, with no preference taken to either right or left side.

The bones were CT scanned using 0.625 mm×0.625 mm×0.625 mm cubic voxels. The result is high resolution, three dimensional radiographs in the form of DICOM image slices. This stacked image data was then segmented and surface models were generated. This process has been found to be reliable with negligible inter- and intra-observer error. These models were then added to the ethnicity-specific statistical bone atlases.

Briefly, a bone atlas is an average mold, or template mesh, that captures the primary shape variation of a bone and allows for the comparison of global shape differences between groups or populations. Bone atlases were developed initially for automatic medical image segmentation; however, it can be used as a way to digitally recreate a bone and conduct statistical shape analyses. In addition, bone atlases have proven useful in biological anthropology as a means of studying sexual dimorphism and for reconstructing hominid fossils and making shape comparisons among fossil species.

For the ethnicity difference analysis, a previously developed technique for creating a statistical representation of bone shape was employed in a novel manner. Three separate statistical atlases of femora were compiled with one atlas containing only American White femora, one atlas containing only American Black femora, and one atlas containing only East Asian femora. Likewise, three separate atlases were created for the tibia and divided in the same manner (i.e., American White, Black tibiae and East Asians). The processes of creating these statistical atlases and adding bones to the atlases are outlined hereafter.

First, all of the bone models in the dataset were compared, and a bone model with average shape characteristics was selected to act as a template mesh. The points in the template mesh were then matched to corresponding points in all of the other training models. This ensures that all of the bones have the same number of vertices and the same triangular connectivity. Next, a series of registration and warping techniques was used to select corresponding points on all the other bone models in the training set. This process of picking point correspondences on new models to be added to the atlas is 'non-trivial'. The matching algorithm described hereafter uses several well-known techniques of computer vision, as well as a novel contribution for final surface alignment.

During the first step in the matching algorithm, the centroids of the template mesh and the new mesh were aligned, and the template mesh was pre-scaled to match the bounding box dimensions of the new mesh. Second, a rigid alignment of the template mesh to the new mesh was performed using a standard vertex-to-vertex Iterative Closest Point (ICP) algorithm. Third, after rigid alignment, a general affine transformation was performed without iteration. This method was applied to align the template mesh to the new mesh using 12 degrees of freedom (including rotations, translations, scaling, and shear). After the affine transformation step, the template and new model have reached the limits of linear transformation, but local portions of the models still remain significantly distant. Since the goal of final surface-to-surface matching is to create new points on the surface of the new model that will have similar local spatial characteristics as the template model, a novel non-linear iterative warping approach was developed to reduce misalignment.

To achieve point correspondence, an iterative algorithm is used where the closest vertex-to-vertex correspondences are found from the template to the new model as before, but now the correspondences from the new model to the template model are also found. Using both of these point correspondences, points on the template mesh are moved toward locations on the new mesh using a non-symmetric weighting of the vectors of correspondence. Next, a subroutine consisting of an iterative smoothing algorithm is applied to the now-deformed template mesh. This smoothing algorithm seeks to average the size of adjacent triangles on the template mesh, thereby eliminating discontinuities. At the beginning of the warping algorithm, the smoothing algorithm uses the actual areas of the surrounding triangles to dictate the smoothing vector applied to each point, which aids in effectively removing outlying points with large triangles. Consequently, at the beginning of the process, the template mesh makes large steps, and larger smoothing is required. Toward the end of the process, however, the smoothing vector is normalized by the total area of the surrounding triangles, which allows for greater expansion of the template mesh into areas of high curvature. After this procedure has been completed on all the femora and tibiae in their respective atlases, the atlases are ready for morphological shape analyses and automated metric comparisons.

An innovative statistical treatment was used to analyze global shape differences between the two groups. This method utilizes the power of (linear and nonlinear) PCA both as a means of variable reduction and as a global shape descriptor. This method is designed to find points of high discrimination between different gender and/or different ethnic groups when normalized against the first principal component (PC), which is considered primarily to scale. This procedure highlights areas on models that would be highly discriminating without the use of any other information. The landmarks identified by this algorithm provide adequate discrimination without the use of any other landmarks between ethnic groups. This feature finder algorithm is used to examine femoral and tibial shape differences independent of the size differences between American Whites, Blacks and East Asians.

A wide array of comparisons was made using specific measurements at defined landmarks on the ethnicity-specific statistical atlases. These landmarks were chosen based on surgical importance, clinical relevance, and historical measurements. Since the atlas consists of homologous points on each femur or tibia model, it provides ample information for automating this process. Also, each bone model in the atlas is aligned to the same coordinate frame. A total of 99 femur and 23 tibia measurements, angles, and indices were calculated. Furthermore, for purposes of brevity, only the most significant metric properties are discussed in the results section. Unless otherwise specified, the measurements outlined below represent three dimensional (3D) Euclidean distances between pairs of landmarks, and angles are measured as 3D rotations between vectors. In some instances these measurements were projected onto a plane for comparison with previous work in the field.

The ordered series of methods used pursuant to the instant disclosure evidenced significant global differences among sex and race, which subsequently allowed for isolation of regions likely to be highly different using the feature finder method, and finally allowed for the coding of algorithms to locate and measure surgically relevant anatomic features with a high degree of accuracy and repeatability. Bones with different scales were considered to have the possibility of shape changes dependent on size. In this way, correlations between measured variables and size were removed in order to expose demonstrable shape differences inherent to the ethnicities.

The inventor has used the foregoing analysis to determine that American Blacks have longer, straighter femora with narrower knees than American Whites. In addition, this analysis revealed differences in the dimensions and orientation of the lateral condyle that result in overall shape differences in the distal femur: American Blacks have a trapezoidal-shaped knee, and American Whites have a more square-shaped knee. For each group, the differences in the distal femur are echoed in the adjacent tibia, whereby American Blacks have a longer lateral tibial condyle. The mean medial-lateral length of the tibial plateau is slightly longer in Blacks than in Whites, but this difference was not overly significant given the sample size. However, American Blacks do have significantly longer and more robust tibiae. In this study, major shape difference was found between East Asian population and both American whites and American blacks.

Although racial differences in lower limb morphology are apparent and register statistically significant, there may be more statistical noise in the American Black sample versus the American White sample. This noise may be a result of the combined effects of genetic admixture since their arrival in the United States, as well as relaxed selection in a more temperate environment. Nonetheless, as discussed earlier, the effects of admixture have not erased the distinctive morphological differences between these subgroups of the American population.

In order, to understand normal knee joint kinematics, one must first understand the anatomy of the articulating surfaces of the knee joint. The knee joint is the articulation of the two largest bones in the human lower extremity, the tibia and the femur. The articular surfaces at the knee joint consists of the curved surfaces that form the lateral and medial condyles of the distal portion of the femur and are in contact with the lateral and medial tibial plateaus of the proximal portion of the tibia.

The femoral condyles blend into an anterior groove, the trochlea, which is the articulation for the patella or kneecap. The tibial plateaus are separated by an intercondylar eminence, which serves as an attachment point for the anterior cruciate ligament and the menisci. The tibial plateaus are also asymmetric, with the lateral plateau the smaller of the two. Anatomical studies of the femorotibial articulation have shown that the medial compartment has greater contact area than the lateral compartment.

The fibula is attached to the tibia's lateral side by a dense membrane along its length and at the ends by cartilaginous joints supported by ligaments. The connection of the bones permits very little relative movement. The proximal tibia-fibular joint is below the level of the tibio-femoral articulation, while the distal ends of the two bones form the proximal end of the ankle joint.

In the normal knee, posterior femoral rollback during an increasing flexion routinely occurs. Greater amounts of posterior femoral rollback have been observed during activities requiring greater magnitudes of flexion such as a deep knee bend maneuver. Posterior rollback is substantially greater at the lateral femorotibial articulation than medially, therefore creating a medial pivot type of axial rotational pattern in which the tibia internally rotates relative to the femur as flexion increases. Numerous kinematic evaluations have found a similar pattern and magnitude of posterior femoral rollback during deep flexion activities. This differs somewhat from axial rotational patterns observed after total knee arthroplasty (TKA), which showed lower magnitudes of axial rotation and occasional pathologic rotational patterns such as lateral pivot rotation and reverse screw-home rotation (tibia externally rotating relative to the femur with increasing flexion).

Also, the anterior translation of the femur on the tibia observed after TKA has numerous potential negative consequences. First, anterior femoral translation results in a more anterior axis of flexion, lessening maximum knee flexion. Second, the quadriceps moment arm is decreased, resulting in reduced quadriceps efficiency. Third, anterior sliding of the femoral component on the tibial polyethylene (PE) surface risks accelerated PE wear.

A primary objective of TKA should be to reproduce the kinematics of a normal knee. At present, this objective is largely overlooked. Numerous in vivo, weight bearing, and fluoroscopic analyses have shown that normal knee kinematics are difficult to obtain after TKA using existing orthopaedic implants. Multiple kinematic abnormalities (reduced posterior femoral rollback, paradoxical anterior femoral translation, reverse axial rotational patterns, and femoral condylar lift-off) are commonly present. Understanding these kinematic variances assisted in design of better TKA implants, which work toward reducing and eliminating these kinematic abnormalities or at least accommodating them without creating adverse conditions that limit implant performance or longevity. Most of the knee implants are off-the-shelve-knee systems, which are designed for average motion—not patient specific kinematics. Accordingly, TKA motion and kinematics of the knee that are indistinguishable from a normal knee should utilize customization for each patient. Currently, customization is a difficult task, but the instant disclosure addresses this customization, in part, by offering a deformable articulating template (DAT) methodology described hereafter.

For purposes of the instant disclosure, radius of curvature is the radius of a circle having a circumferential curvature that approximates the curvature of a rounded object. For example, the radius of curvature is infinite for a straight line, while the radius of decreases from infinity as the curvature increases. In particular, the radius of curvature for a smaller circle is less than the radius of curvature for a larger circle because the curvature of the smaller circle is greater than the curvature of the larger circle. Simply put, the smaller the radius of curvature, the larger the curvature.

The inventor has found that one may map and simulate the curvature of the natural knee condyles by applying two or more radii of curvature along the camming surfaces from anterior to posterior. In particular, it has been found that for the Caucasian population, five distinct radii of curvature closely track the curvature of the camming surfaces of the condyles from anterior to posterior. Moreover, it has been found that asymmetry in the radii of the curvature of the condyles is responsible for imposing an internal rotation of the tibia with respect to the femur during flexion. Beyond 20° of flexion, sliding motion begins on both condyles.

Extension of the knee joint produces a coupled external rotation of the tibia with respect to the femur; this rotation has been described as the "screw-home" movement of the knee. This screw-home movement is due to the existence of a larger area of bearing surface on the medial condyle than on the lateral condyle. When the whole articular surface of the lateral condyle has been used up, the femur rotates around the tibial spine until the joint is screwed home or close packed in extension. As the knee joint flexes and extends, this rotation causes the tibial motion on the femur to assume a spiral or helicoid form that results from the anatomical configuration of the medial femoral condyle. As the tibia slides on the femur from the fully extended position, it descends and ascends the curves of the medial femoral condyle and simultaneously rotates externally. This motion is reversed as the tibia moves back into the fully flexed position. The screw-home mechanism gives more stability to the knee in any position than would be possible if the femorotibial joint was a pure hinge joint.

The meniscal cartilages (menisci) between the femoral condyles and the tibial articular surfaces are two crescentic fibrocartilage structures that serve to deepen the articular surfaces of the tibia for reception of the femoral condyles. On cross-section, the menisci have a wedge-like appearance. The menisci perform several important functions, including (1) load transmission across the joint, (2) enhancement of articular conformity, (3) distribution of the synovial fluid across the articular surface, and (4) prevention of bone impingement during joint motion. When the menisci are present, the load-bearing area for each condyle approximates 6 $cm^2$, but this surface area decreases to approximately 2 $cm^2$ when the menisci are damaged or severely degraded. Therefore, when the effective area of load bearing is increased, the stress transferred to the cartilages is reduced and vice versa.

In the normal knee joint, the anterior cruciate ligament (ACL) and the posterior cruciate ligament (PCL) are intrinsic, lying inside the joint in the intercondylar space. These ligaments control the anterior-posterior and axial rotational motion in the joint. The anterior cruciate ligament provides the primary restraint for anterior movement of the tibia relative to the femur while the posterior cruciate ligament offers the primary restraint to posterior movement of the tibia, accounting for over 90% of the total resistance to this movement.

The morphologic shape of the distal femur should dictate the shape, orientation, and kinematics of the prosthetic replacement used for TKA. Traditional prosthetic designs incorporate symmetric femoral condyles with a centered trochlear groove. Traditional surgical techniques center the femoral component to the distal femur and position it relative to variable bone landmarks. However, documented failure patterns and kinematic studies demonstrate how traditional design and surgical techniques reflect a poor understanding of distal femoral morphology and knee joint kinematics, in addition to a disregard for the patella and its tracking of the distal femur.

The trochlea is designed to guide and hold the patella. Patella tracking is influenced by many different factors: the geometry of the trochlear groove, the geometry of the posterior side of the patella, soft tissue extensor mechanism and the orientation of the tibia. The normal movement of the patella on the femur during flexion is a vertical displacement along the central groove of the femoral patellar surface down the intercondylar notch. The geometry of the trochlear groove and the posterior side of the patella constrains patella tracking, particularly at high flexion angles. The patella is held centrally by the conformity of the facets with the sulcus of the femur and by the patellofemoral ligaments. These ligaments represent a conformation of the capsule into thickened structures on the medial and lateral side of the patella. These ligaments are located superiorly and inferiorly on either side, and extend from the anterior surface of the patella posteriorly to the side of each femoral condyle. These ligaments also constrain the motion of the patella, but can be overruled by the sulcus constraints or by external forces. In a normal knee it is acceptable to presume that the tracking of the patella will be very similar to the orientation of the trochlea. As a result, the orientation of the trochlear groove of a knee prosthesis should be similar to the orientation of the natural trochlea to reproduce this natural patella track.

In sum, the knee joint is an example of very well balanced system. A slight change within this system, affects the whole system. Changes within the patella-femoral joint can have considerable long term effects, as the transmitted forces within this part of the knee joint are relatively high. TKA easily induces changes within the patella-femoral joint. At present, the simulated trochlear groove orientation of TKA components does not conform to the natural trochlear orientation. Accordingly, the groove orientation of future femoral components should incorporate a trochlear groove that simulates the natural orientation of the trochlear groove of a natural femur.

BRIEF DESCRIPTION OF THE DRAWINGS

FIG. 119 is a posterior view of lateral ML and AP tracks.

FIG. 120 is an elevated perspective view showing the sheet body and cartilage cutting body (lateral).

FIG. 121 is an anterior view of a distal femur before and after lateral cartilage removal.

FIG. 122 is a posterior view of a distal femur before and after lateral cartilage removal.

FIG. 123 is an anterior view of an anterior ML track.

FIG. 124 is a bottom view of an anterior ML track,

FIG. 125 is an elevated perspective view showing the sheet body and cartilage cutting body (anterior).

FIG. 126 is an anterior view of a distal femur before and after anterior cartilage removal.

FIG. 127 is a bottom view and an elevated perspective view of a combined cut pathway.

FIG. 128 is an anterior view of a distal femur before and after total cartilage removal.

FIG. 129 is a posterior view of a distal femur before and after total cartilage removal.

FIG. 130 is a profile view of a microsurgical robot guide mounted to a distal femur.

Figure 130:
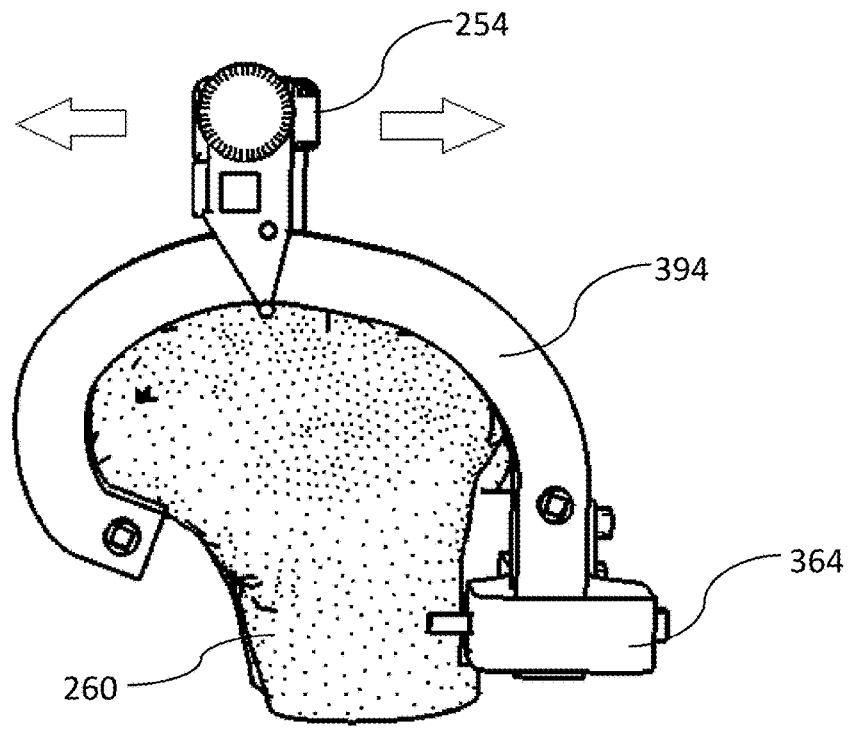
Figure 131:
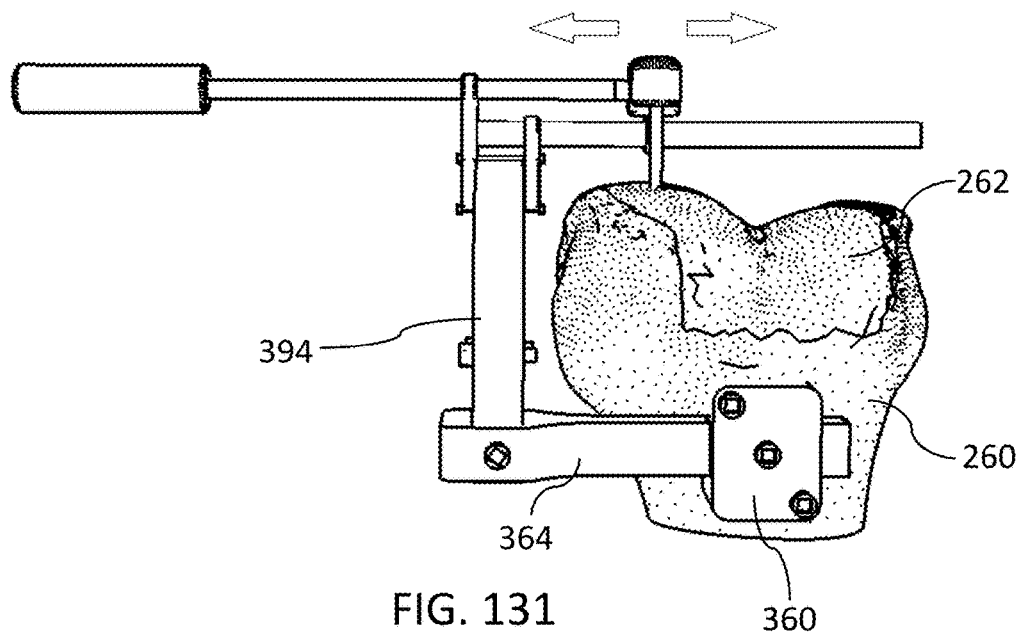

FIG. 131 is an anterior view of the microsurgical robot guide of FIG. 130.

Figure 132:
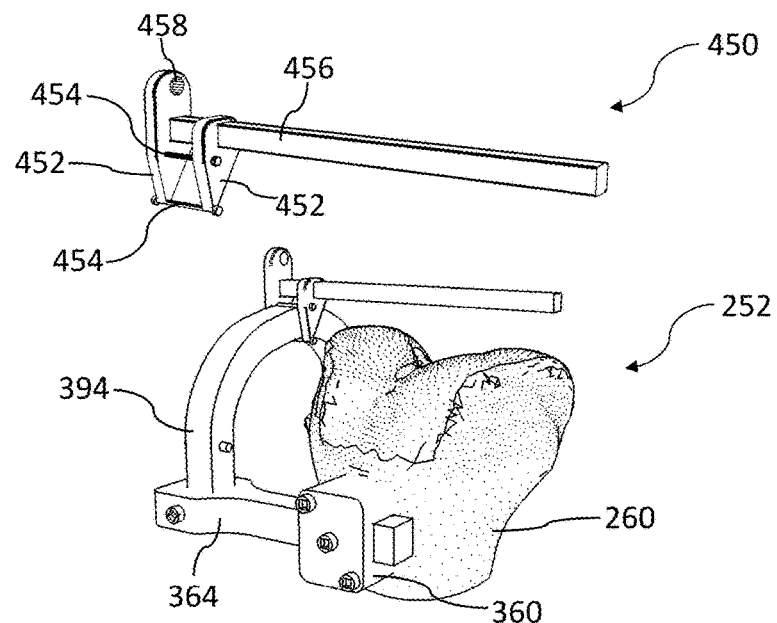

FIG. 132 is an elevated perspective view (from lateral) of the microsurgical robot guide of FIG. 130, along with a separate elevated perspective view of an exemplary support frame (shown without the robot and associated equipment).

Figure 133:
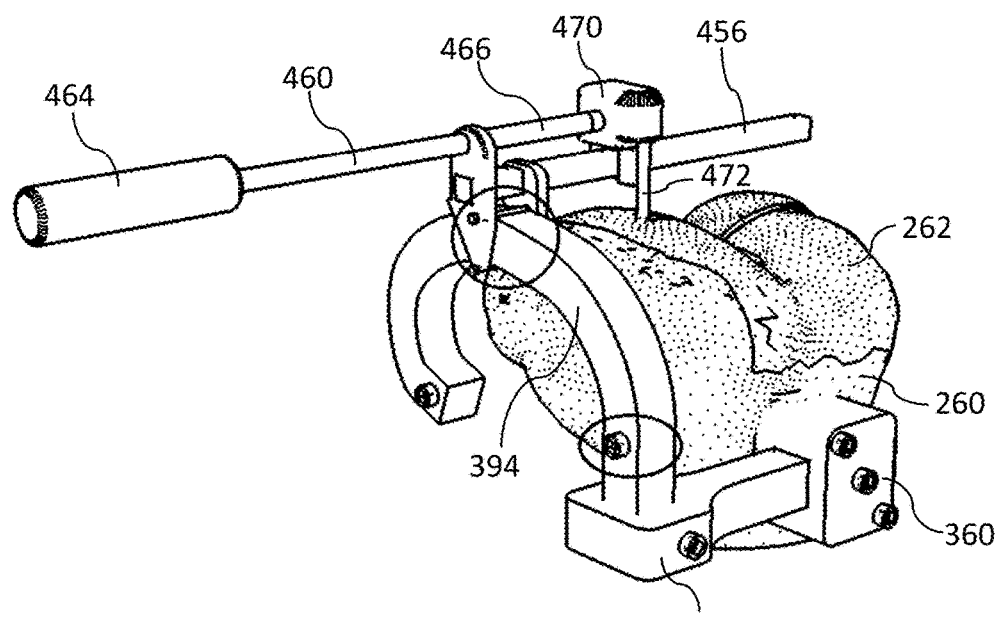

FIG. 133 is an elevated perspective view (from medial) of the microsurgical robot guide of FIG. 130.

Figure 134:
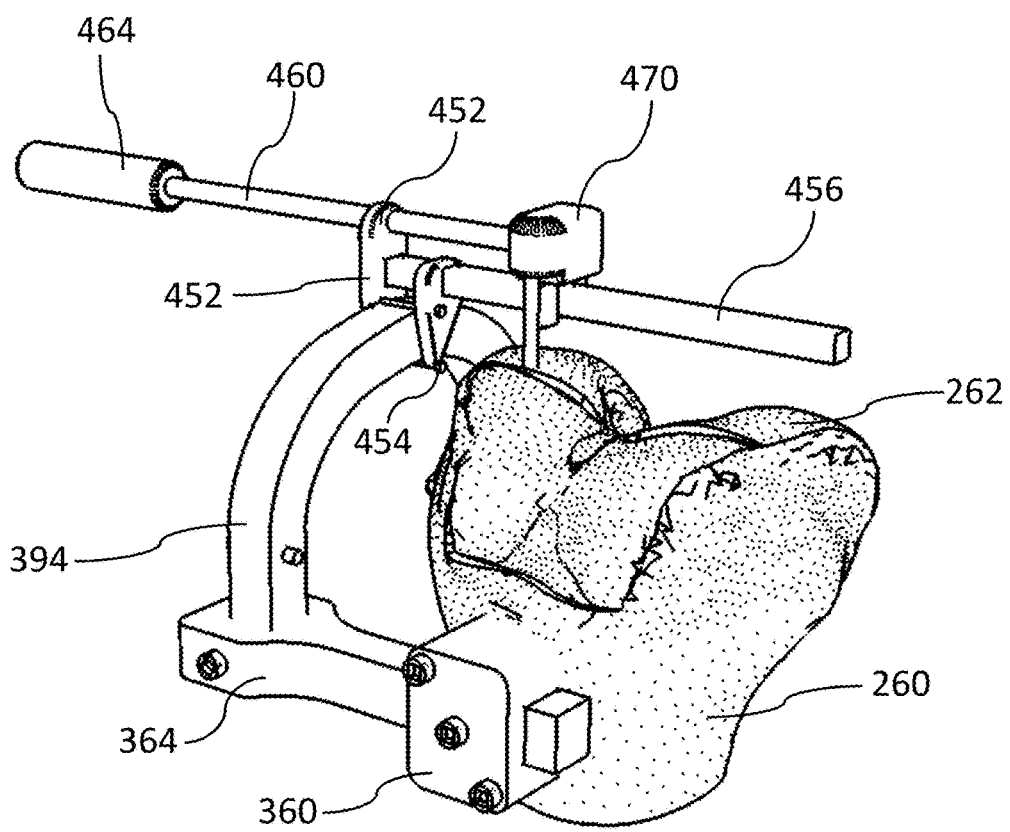

FIG. 134 is an elevated perspective view (from lateral) of the microsurgical robot guide of FIG. 130.

Figure 135:
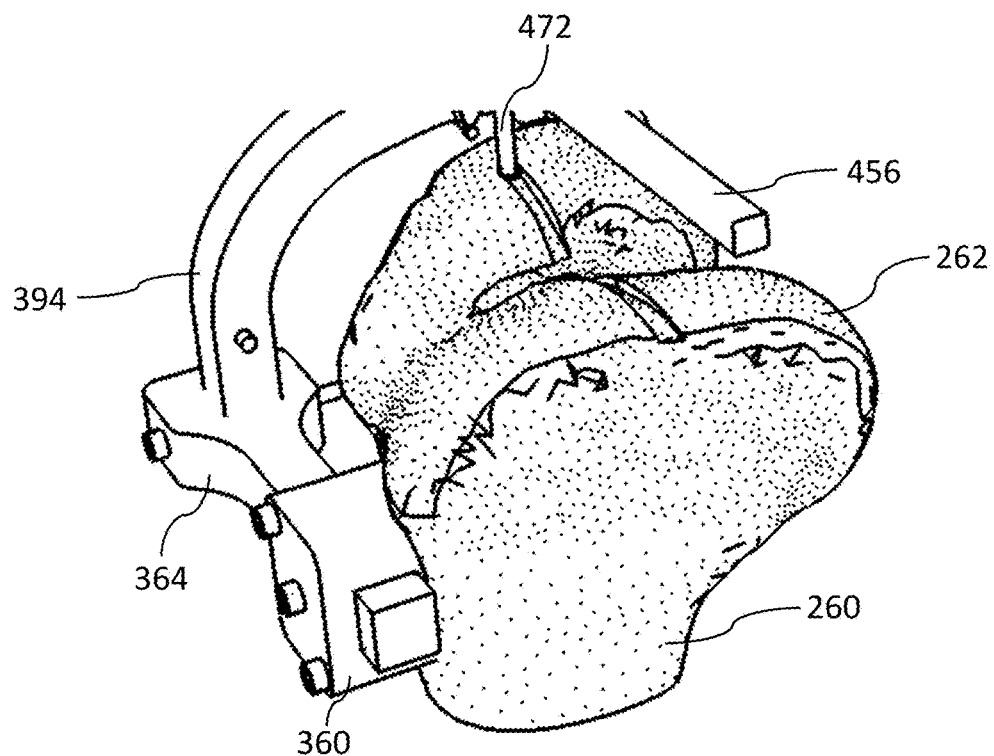

FIG. 135 is an elevated perspective view (from profile, lateral) of the microsurgical robot guide of FIG. 130.

Figure 136:
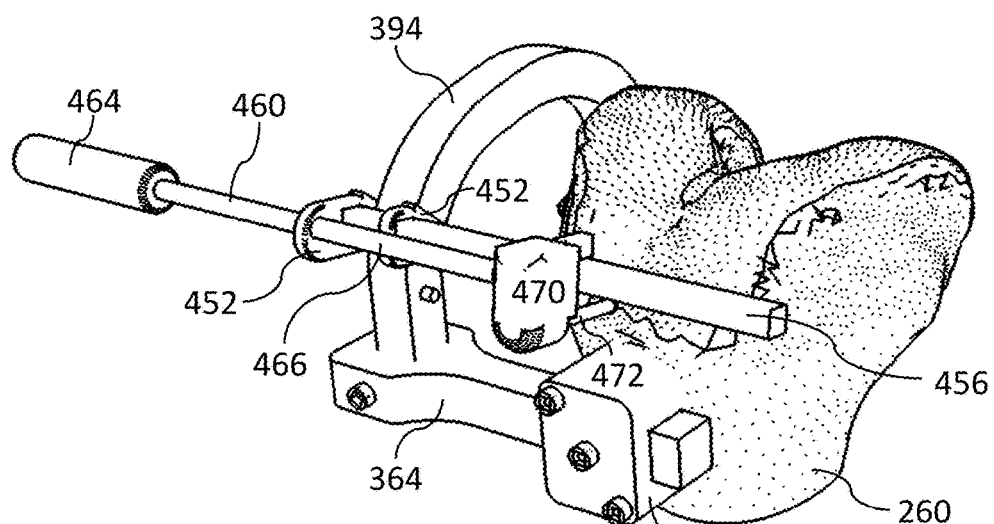

FIG. 136 is an elevated perspective view (from lateral) of the microsurgical robot guide of FIG. 130 showing the microsurgical robot in an anterior position.

DETAILED DESCRIPTION OF EXEMPLARY EMBODIMENTS

The exemplary embodiments of the present invention are described and illustrated below to encompass prosthetic knee implants, jigs for use with preparing tissue to receive prosthetic knee implants, and methods and devices for designing prosthetic knee implants and jigs, as well as microsurgical robots for use with the same. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

The following are definitions that relate to axes, landmarks, and measurements with respect to the distal femur. These definitions also govern the proper construction of these terms as used in the instant disclosure.

Transepicondylar Axis (TEA)—This measurement is known in the anthropological literature as biepicondylar breadth. To compute the clinical transepicondylar axis (TEA), rough sets of vertices were manually defined on an average femur on the most lateral prominence of the lateral epicondyle and the most medial prominence of the medial epicondyle. This step was only performed once, since vertices in the atlas femora are homologous. Using these rough sets of points, a search region of 10 mm radius was defined from the centroid of the rough sets of vertices on both the lateral and medial sides. Defining the vector from each of these centroids then gives a rough direction for the TEA. A pair of points was selected by maximizing the distance in this rough direction; these selected points form the endpoints of the TEA measurement.

Transepicondylar Axis Length (TEAL)—distance between the medial and lateral condyles.

Anteroposterior Height (APH)—distance between anterior cortex points and the posterior plane.

Medial Anteroposterior Height (MAP)—distance between most anterior and posterior aspects of the medial condyle.

Lateral Anteroposterior Height (LAP)—distance between most anterior and posterior aspects of the lateral condyle.

Anatomic Axis—Distal Axis Angle—angle between anatomic axis and axis connecting the two most distal points of the medial and lateral condyles.

Patellar Groove Height (PGH)—distance between aspect of the intercondylar notch and the midpoint between the two most distal points on the medial and lateral condyles.

Anteroposterior Angle Difference (AP-AD)—angle of the vector connecting the two most anterior points on the lateral and medial condyles and the vector relative to the posterior plane.

Anterior Mediolateral Length (AML)—distance between the two most anterior aspects of the medial and lateral condyles.

Posterior Mediolateral Length (PML)—distance between the two most posterior aspects of the medial and lateral condyles.

Distal Mediolateral Length (DML)—distance between the two most distal aspects of the medial and lateral condyles.

Condylar Twist Angle (CTA)—angle between the transepicondylar axis and posterior condylar axis.

The following are definitions that relate to axes, landmarks, and measurements with respect to the proximal tibia. These definitions also govern the proper construction of these terms as used in the instant disclosure.

Mediolateral Width (ML)—maximum width of the tibia plateau in the mediolateral direction.

Anteroposterior Height (AP)—length of the tibial plateau in the anteroposterior direction, passing through the midpoint of the tibial intercondylar eminence.

Eminence Mediolateral Ratio (EM_W)—medial plateau mediolateral width to mediolateral width ratio.

Tuberosity Eminence Vector Angle (TEVA)—angle between anteroposterior direction and a line connecting the intercondylar eminence midpoint and tibial tuberosity.

Lateral Plateau Mediolateral Width (LPW)—length of the lateral tibial plateau in the mediolateral direction.

Lateral Plateau Anteroposterior Height (LPH)—length of the lateral tibial plateau in the anteroposterior direction.

Medial Plateau Mediolateral Height (MPW)—length of the medial tibial plateau in the mediolateral direction.

Medial Plateau Anteroposterior Height (MPH)—length of the medial tibial plateau in the anteroposterior direction.

End of Definitional Section

Morphological differences exist between genders and ethnicities. A first exemplary embodiment comprises a software package utilizing statistical bone atlases to define these morphological differences of the knee. This software package uses the morphological information to create gender and ethnic specific mass customized implants, as well as patient specific implants, for the knee. These knee systems may comprise total cruciate retaining, total posterior stabilized, partial, and unilateral. The exemplary software package is also capable of analyzing and reshaping existing knee systems.

Figure 1A:
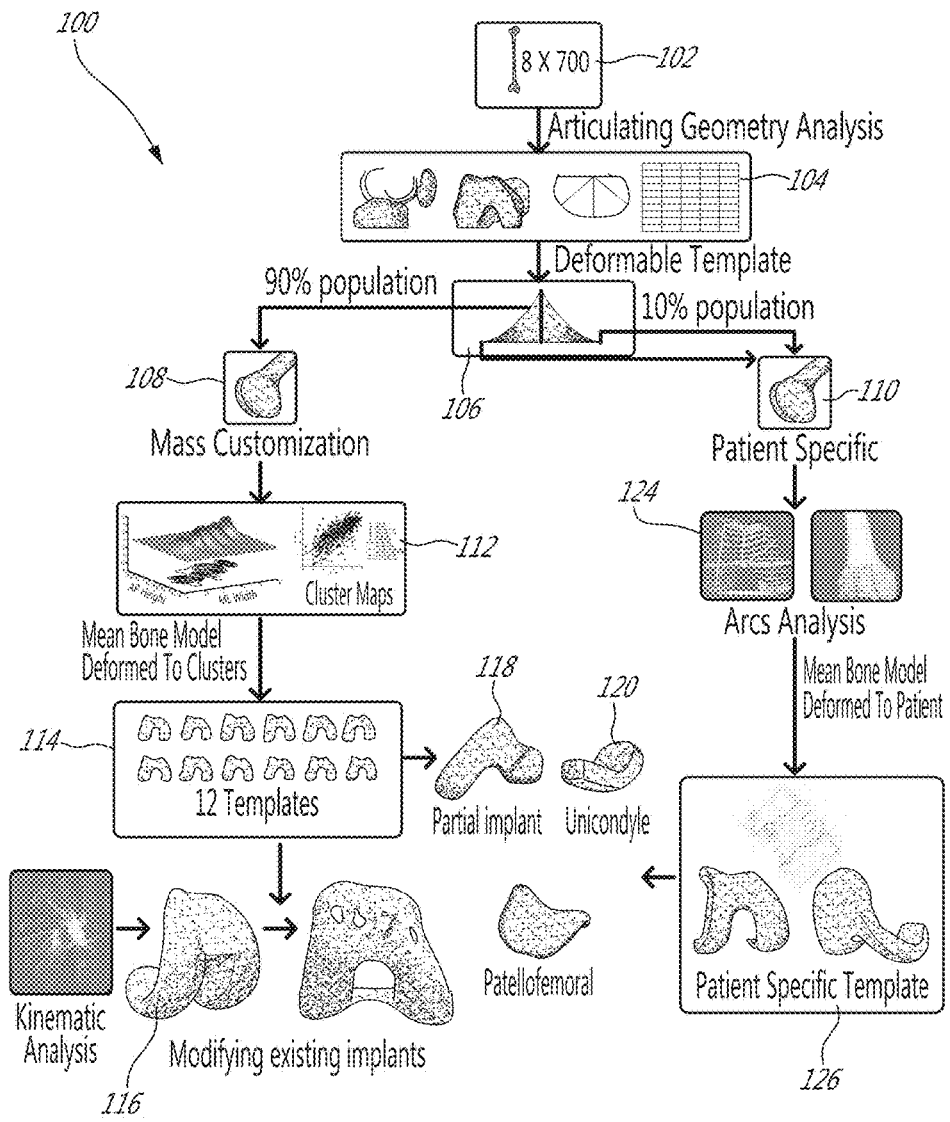
FIG. 1A is a schematic diagram showing how an exemplary software package generates a prosthetic implant design.

Referring to FIG. 1A, an exemplary schematic diagram 100 depicts the high level processes carried out by the exemplary software package to create mass customized or patient specific orthopaedic implants. In exemplary form, the software package starts by importing 102 a patient femur and tibia model for analysis 104 of the articulating geometry according to the patient's gender and ethnicity. After the analysis 104 of the articulating geometry is carried out, the software package determines 106 whether the patient's bone anatomy fits within a range of sizes available for a mass customized implant. Thereafter, the process can go in one of two directions 108, 110: (a) a mass customized orthopaedic implant; or, (b) a patient specific orthopaedic implant.

In the first direction 108, presuming the patient's bone anatomy fits within a range of template sizes available for a mass customized implant 112, the software package selects the appropriate template size 114 for the mass customized implant. For approximately 90% of the population, the patient will fall within the range of template sizes for the mass customized implant family. Thereafter, the software package processes the selected template size and modifies the template to have the contours of the template more closely approximate the contours of the patient's natural anatomy, whether it is a total femoral 116, a partial femoral 118, or a unilateral femoral 120, is then selected for the patient.

Figure 1B:
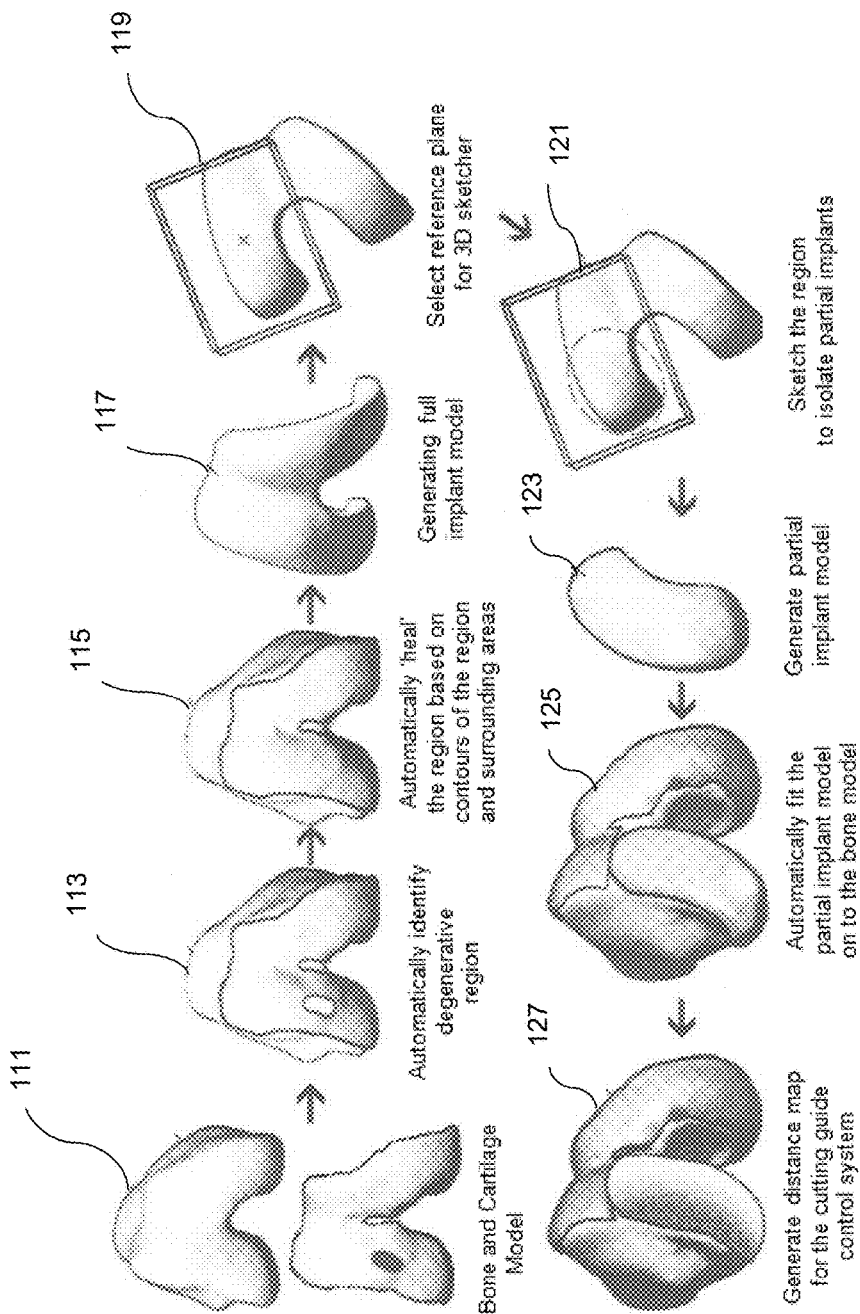
FIG. 1B is a schematic depicting an exemplary process flow for generation of a patient specific prosthetic implant.

Conversely, in the second direction 110 (presuming the patient's bone anatomy does not fit within a range of template sizes available for a mass customized implant, or the consulting physician opts for a patient specific implant over a mass customized implant) and as shown in FIG. 1B, the software package analyzes 124 three dimensional bone models of the patient's actual femur and tibia (constructed from MRI, CT, X-Ray, etc.) using an arc analysis. Prior to analyzing the patient's actual femur and tibia, three dimensional virtual bone models are created 111 that include models of the patient's current cartilage. In circumstances where the cartilage is degenerative, the software package identifies this degeneration 113 and automatically supplements the cartilage model to create a healthy cartilage model 115. Thereafter, the arc analysis 124 identifies and maps the contours of the medial and lateral profiles of the patient's articulating surface, which are parameterized, to create a patient specific template 126. This patient specific template 126 is then further refined/customized to create 117 a patient specific orthopaedic implant 242 (see FIG. 52) (whether total, partial, or unilateral) to fit the patient's needs.

Referring to FIG. 1B, to the extent a partial or unilateral implant is desired, the full implant model is available to have a surface point selected, thereby causing the software package to generate 119 a reference plane. This reference plane is normal to the surface point on the model selected and is manipulatable to define the field of view. In exemplary form, the field of view is manipulated to encompass the areas on the implant model that will be used to construct the partial or unilateral implant. Thereafter, in a region isolation step 121, the user of the software package selects the particular portions of the implant model that will be used to create the partial or unilateral implant. The software then automatically extracts these regions and creates 123 a stand-alone partial or unilateral implant. Thereafter, the stand-along implant is fit 125 onto the dimensional virtual bone models. This fitting includes automatic removal of cartilage and possibly some bone as part of an automatic resurfacing that occurs via the software package. After proper fitting, the stand-alone implant is removed from the bone model, thereby leaving behind bone model with a resurfaced portion. This resurfaced portion of the three dimensional bone model is analyzed 127 by the software package to create three dimensional cutting directions (for an automated or computerized cutter) that allow the cutter to resurface the patient's actual bone to accept the fabricated stand-alone implant.

Figure 2:
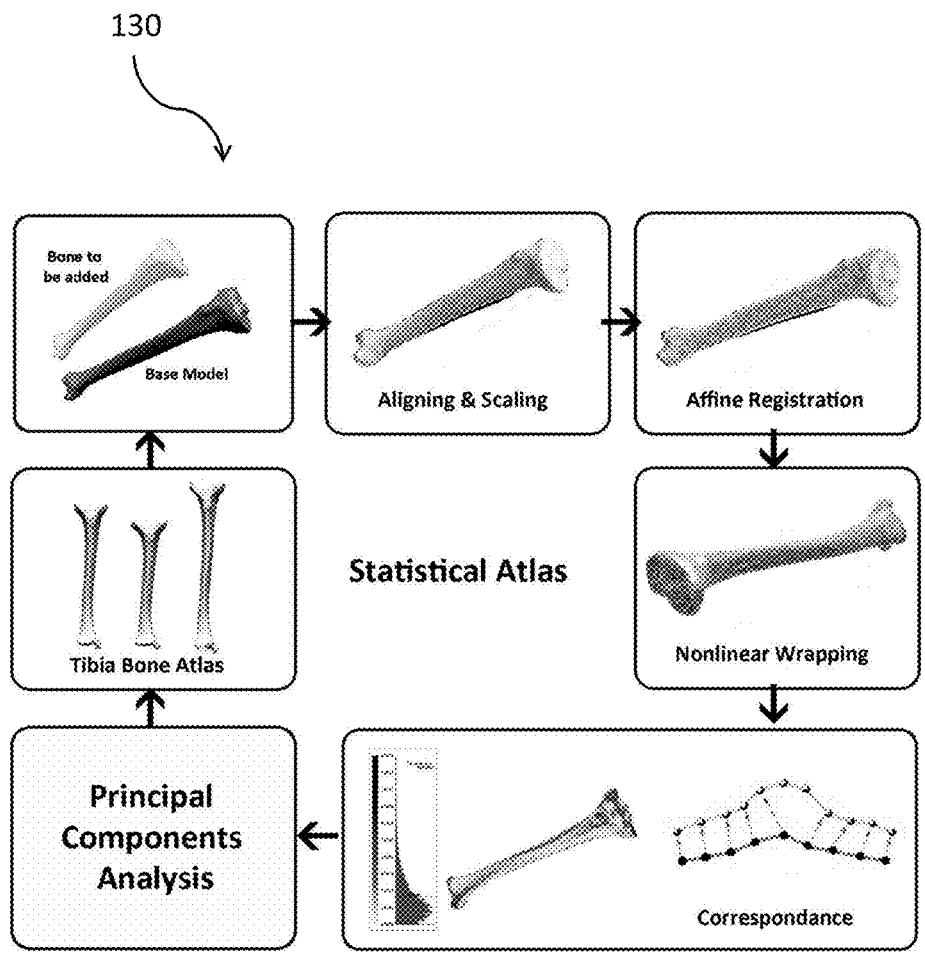
FIG. 2 is a schematic diagram showing a statistical atlas overview.

Referencing FIG. 2, the imaging modality used to acquire the patient femur and tibia models that are imported 102 into the software package may include, without limitation, one or more of computed tomography (CT), magnetic resonance imaging (MRI), and X-radiation (X-rays). Post imaging of the patient's femur and tibia, an electronic model of the patient's femur and tibia are then automatically constructed and added to the software package's bone atlases 130. A bone atlas is an average model that captures the primary shape variations of bones and allows for the comparison of global shape differences between groups or populations. In exemplary form, the software package includes twelve separate statistical atlases 130 of femora and tibiae (six femora and six tibiae) are created that correspond to three ethnicities (Caucasians, African Americans, and Asians) and both genders (male and female). In other words, the software package includes a separate statistical atlas for both the femora and the tibia for a male Caucasian, a female Caucasian, a male African American, a female African American, a male Asian, and a female Asian. By having statistical atlases 130 that are gender and ethnic specific, the resulting atlas tibia and femur are standardized, normalized, and guaranteed to have landmark correspondence across a population.

Figure 3:
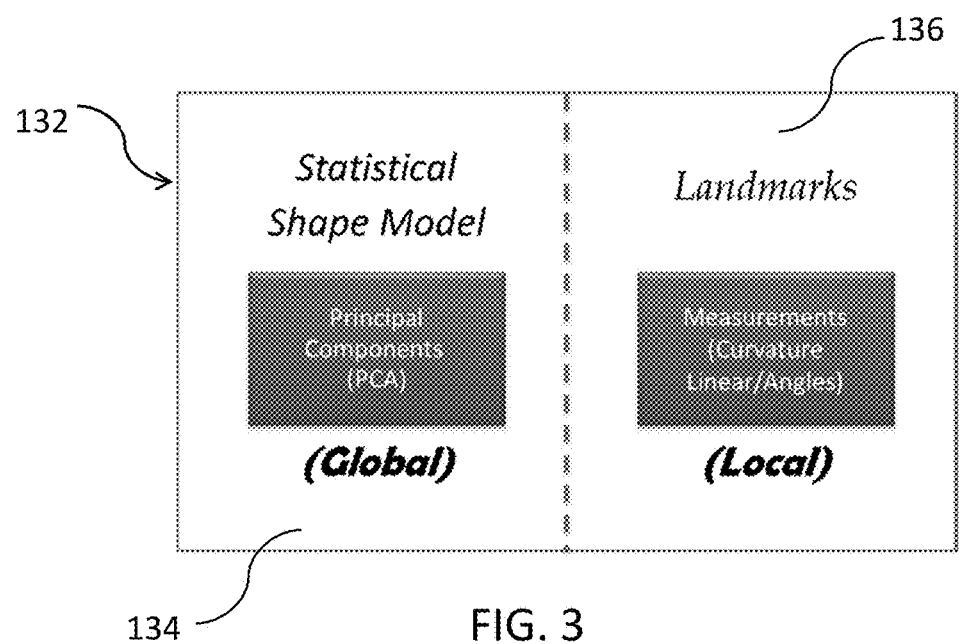
FIG. 3 is a schematic diagram showing a two step feature extraction process carried out by the exemplary software package.

Referring to FIG. 3, a two-step feature extraction methodology 132 is implemented by the exemplary software package to fully identify shape differences among ethnicities. In a first step 134, global shape differences between the sexes in each ethnicity and between the sexes across all ethnicities (in exemplary discussion, three ethnicities) are identified. This first step 134 makes use of principle component analysis, a mathematical tool that reduces the dimensionality of variables while maintaining most of the variance of the original data, both as a means of variable reduction and as a global shape descriptor. Principle component analysis is used by the software package to find points of high discrimination between different sex and ethnic groups when bones falling within these groups are normalized against the first principal component. The first principal component is considered primarily scale and is used to highlight highly discriminatory areas between a standard bone and the bones falling into the different sex and ethnic groups. A principle component analysis algorithm is used by the software package to analyze shape differences (independent of size differences) between the sexes and among the ethnic populations (Caucasians, African Americans, and Asians).

Figure 4:
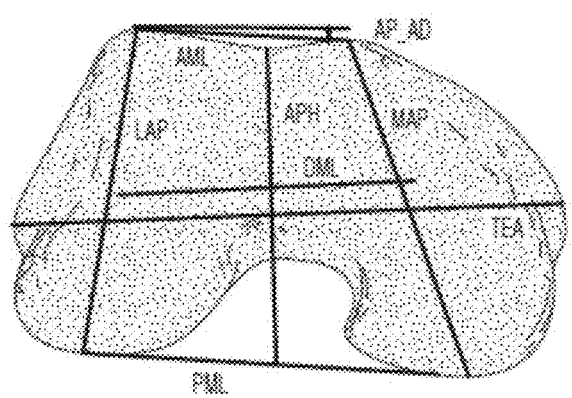
FIG. 4 is a distal view of a femur showing certain anatomic measurements.
Figure 5:
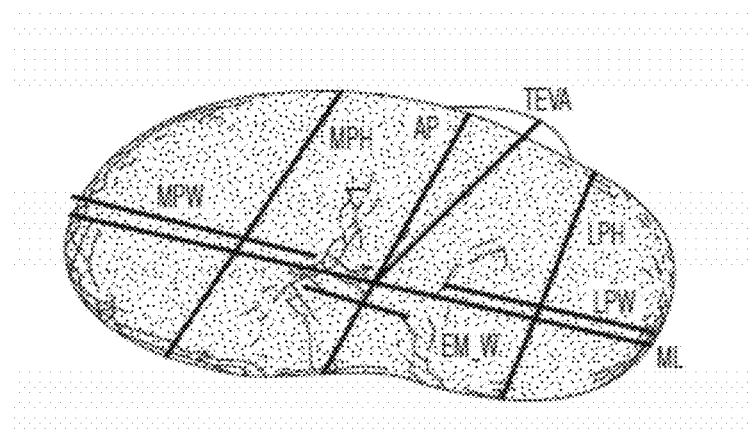
FIG. 5 is a proximal view of a tibia showing certain anatomic measurements.
Figure 6:
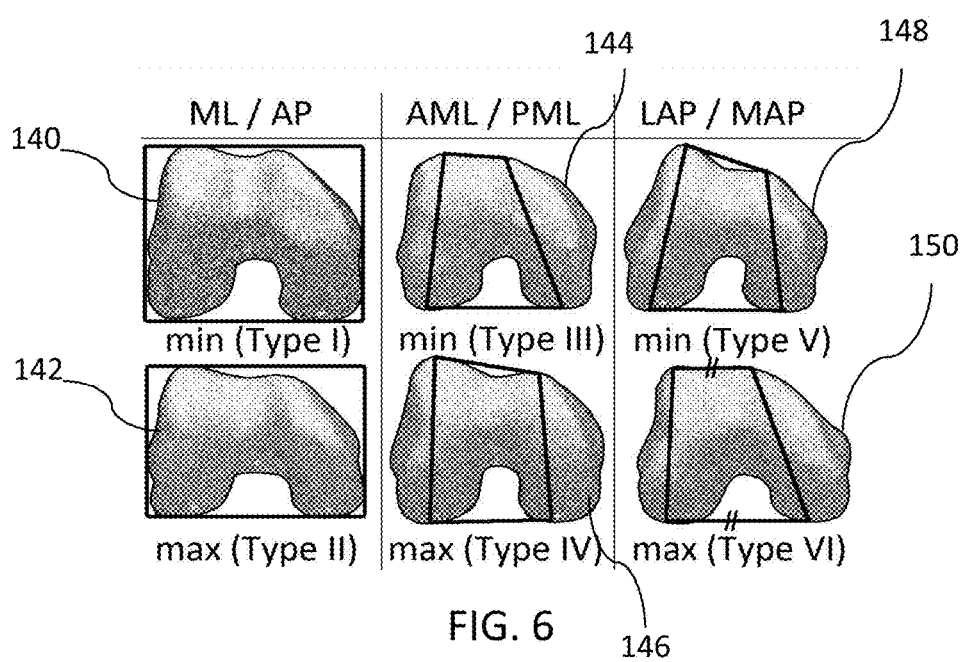
FIG. 6 is a series of distal views of six femurs showing various classification in accordance with the instant disclosure.

Referring to FIGS. 3-5, following the first step 134 is a second step 136 that utilizes anatomic and surgical landmarks to automatically calculate linear measurements, angular measurements, and curvature after a bone is added to the atlas. In FIGS. 4 and 5, each of the measurements taken by the software package for the tibia and femur bone models is marked with a corresponding acronym to show precisely the where the measurements are taken. It should be noted that the measurement acronyms were listed in the preceding definitional section and reference is had to that section for a more detailed explanation of each measurement.

Referencing FIGS. 6-10, the software package uses six classifications 140-150 to describe femoral shape based on three normalized ratios. Type I 140 and Type II 142 classify femoral shape relative to mediolateral width/anteroposterior height (ML/AP), Type III 144 and Type IV 146 classify femoral shape relative to anterior mediolateral length/posterior mediolateral length (AML/PML), and Type V 148 and Type VI 150 classify femoral shape relative to medial anteroposterior height/lateral anteroposterior height (MAP/LAP). By using these six classifications 140-150, the software package identifies morphological differences between ethnicities and gender.

Figure 7:
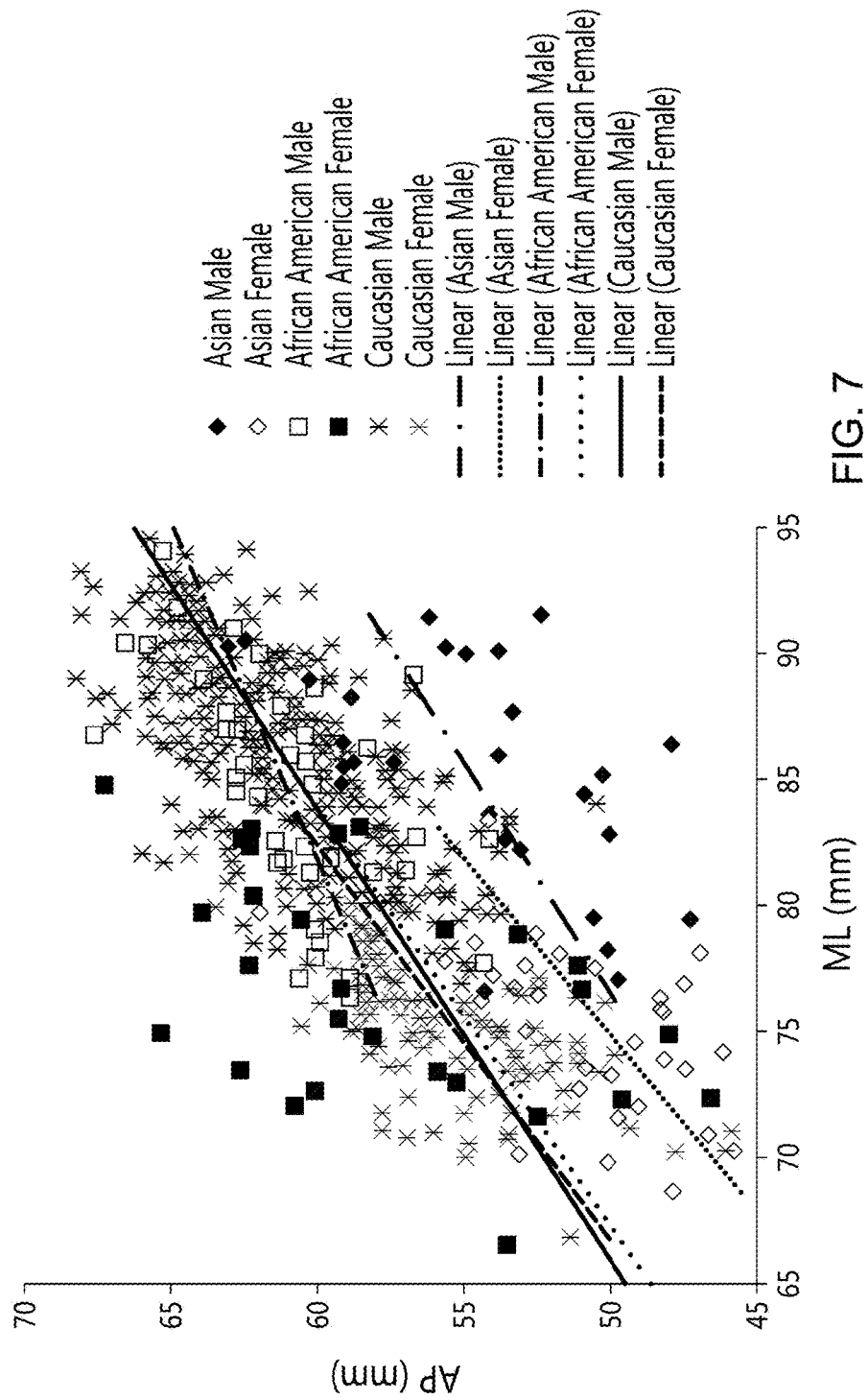
FIG. 7 is a plot showing femoral AP length as a function of ML length for male and female Asians, African Americans, and Caucasians.
Figure 8:
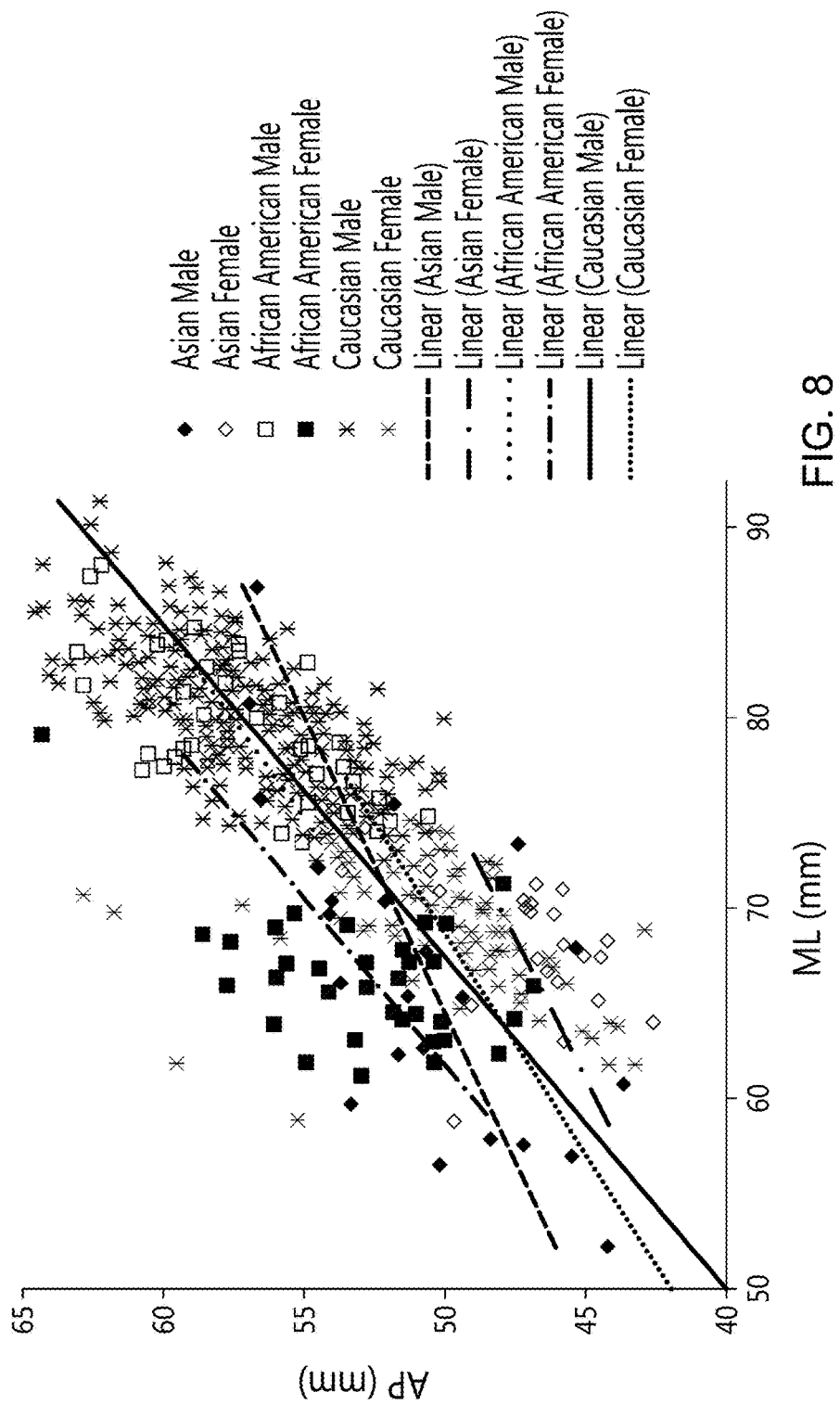
FIG. 8 is a plot showing tibial AP length as a function of ML length for male and female Asians, African Americans, and Caucasians.

As shown in FIGS. 7 and 8, plots of measurements taken for anterior-posterior (AP) height and medial-lateral (ML) width of femurs and tibiae from various ethnicities (Caucasian, African American, and Asian) and genders confirm that significant morphological differences exist between each group.

Figure 9:
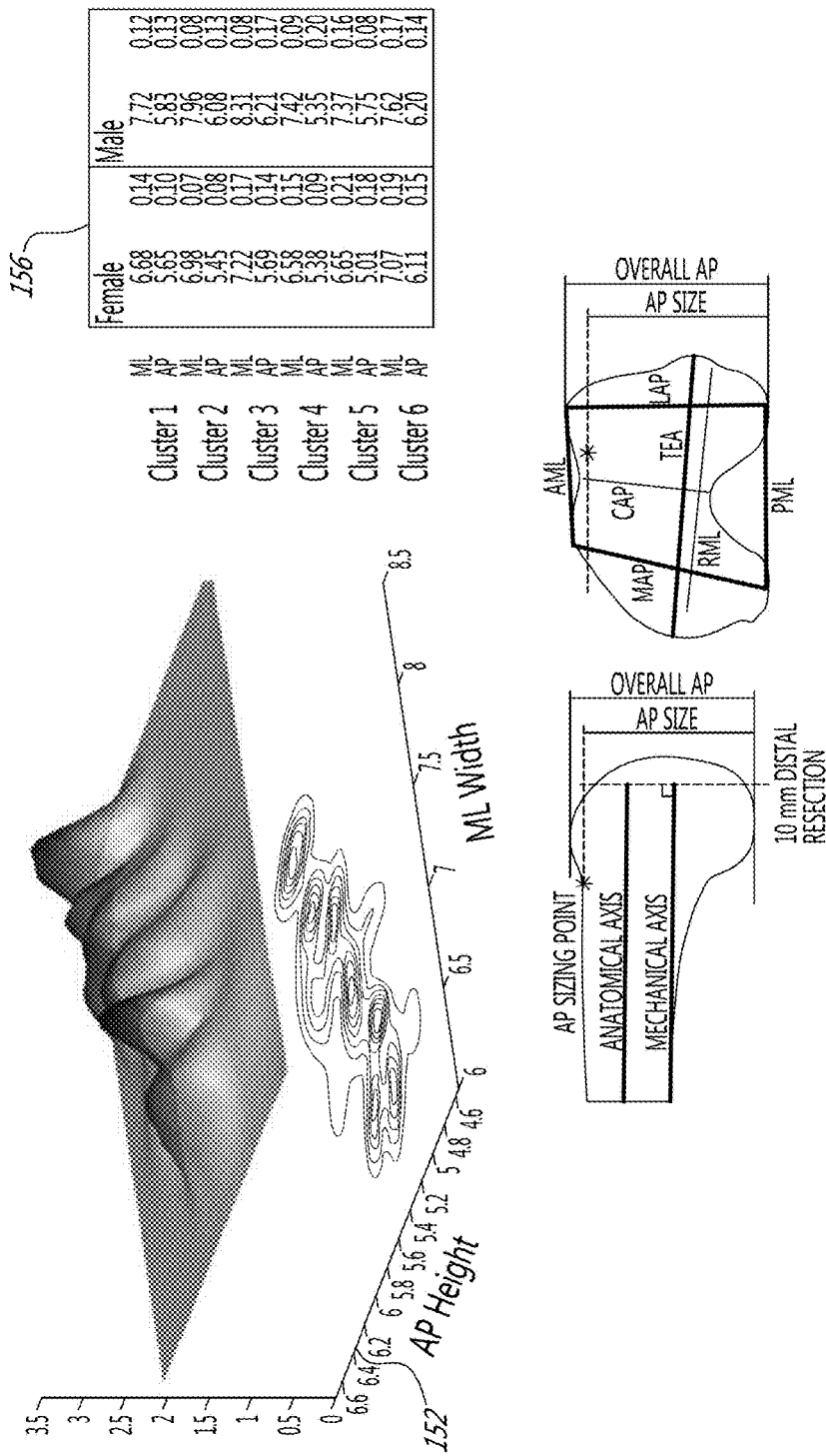
FIG. 9 is a depiction of Caucasian male and female femur size clusters classified by AP and ML dimensions.
Figure 10:
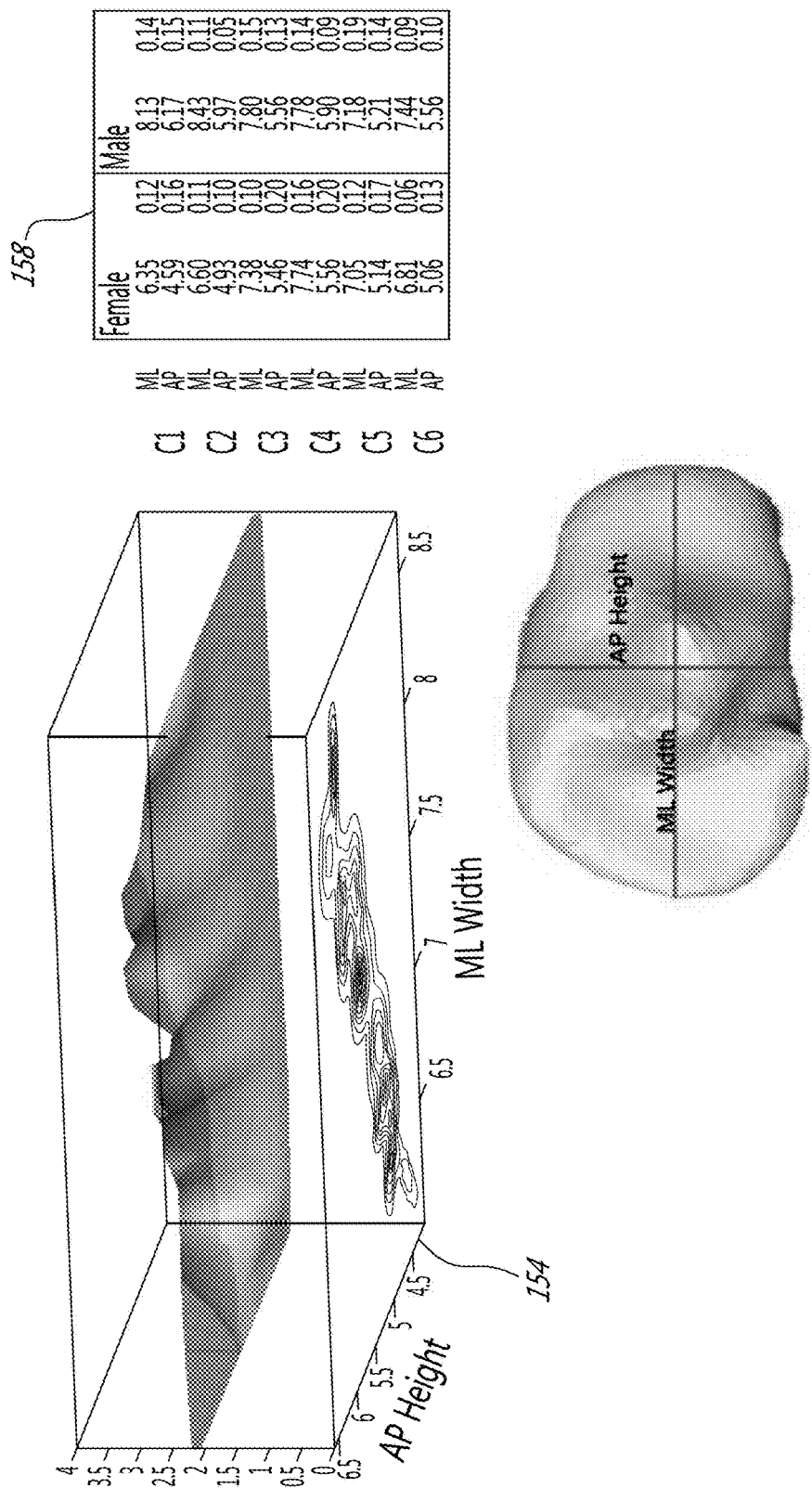
FIG. 10 is a depiction of Caucasian male and female tibia size clusters classified by AP and ML dimensions.

Referring to FIGS. 9, 10, 12 and 13, the software package was used to carry out an exemplary analysis of femoral and tibial ML width and AP height dimensions within the Caucasian male and female populations that yielded six clusters of male and female sizes for a total of twelve Caucasian sizes. In particular, the ML width measurements were plotted against AP height measurements which were plotted against a repetition (i.e., frequency corresponding to the number of similarly shaped bones) factor of both measurements in a third dimension to create the three-dimensional (3D) plots 152, 154 for the femur and tibia. Each projection of a 3D plot represented a separate cluster, resulting in six projections for both the Caucasian male and Caucasian female. Each projection is representative of a separate size. FIGS. 9 and 10 also include charts 156, 158 numerically detailing the six sizes for both Caucasian males and females for the femur and tibia. Dimensions (ML, AP) from the remaining ethnicities are also separable and used by the software package to generate 3D plots providing distinct projections (also referred to herein as "clusters") that correspond to distinct sizes for a respective profile (ethnicity and gender, such as Asian female). For example, an AP dimension is between 57 and 67 millimeters for a male patient of European descent, and a ML dimension is between 80 and 95 millimeters for a male patient of European descent. The software package then generates an average bone model for each projection, where the average bone model represents the average of all of the bones that fall within the projection. This average bone model is referred to herein as a template 160.

Figure 11:
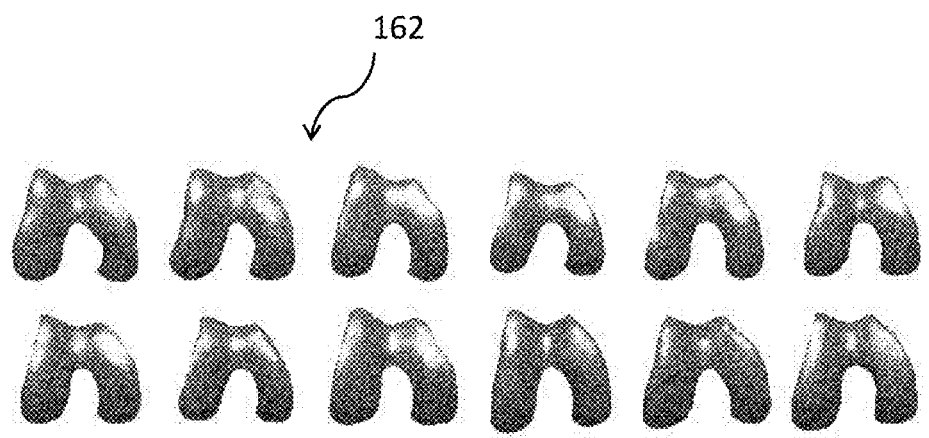
FIG. 11 is a series of Caucasian distal femur templates (male and female) in accordance with the instant disclosure.
Figure 12:
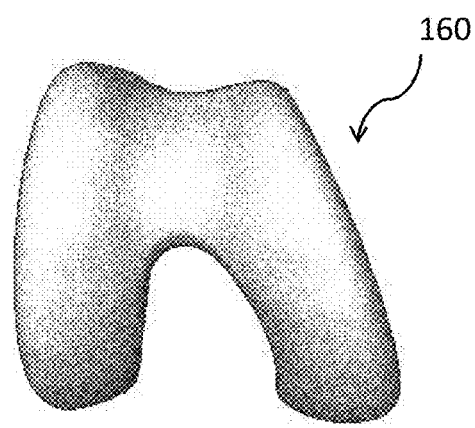
FIG. 12 is an Asian female distal femur template in accordance with the instant disclosure.
Figure 13:
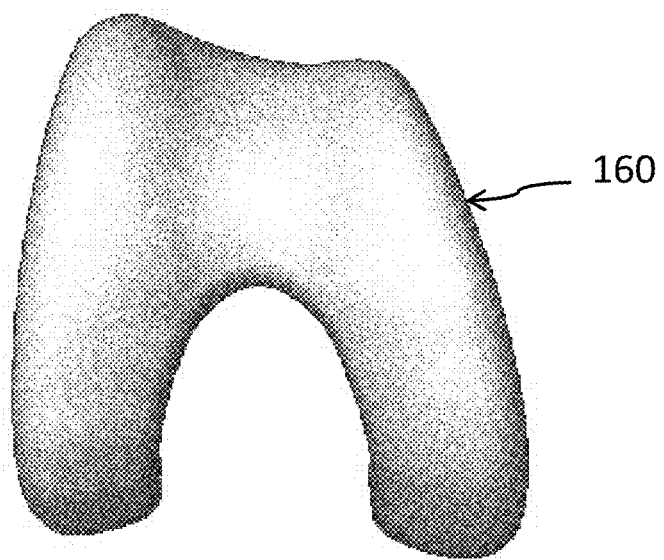
FIG. 13 is an African-American male distal femur template in accordance with the instant disclosure.

Referencing FIGS. 11-13, the software package uses the results of the shape analysis for each ethnicity and gender to create a series of mass customized implant families 162 by using the template bone 160 to create the mass customized implant for that cluster. When a patient is to be fit with a mass customized implant, his/her bone is added to the atlas 130 and classified to assign the bone to a particular cluster. In this manner, the mass customized implant of the assigned cluster is then associated/assigned to the patient.

Referring to FIGS. 1 and 14-16, the exemplary software package utilizes a curvature analysis process 124 to create the mass customized implants and patient specific implants. In exemplary form, the curvature analysis 124 is applied to each template femur 160 and each template tibia 160 within the atlas to generate the profile and curvature for those templates. In contrast, for a patient specific implant, the curvature analysis is applied directly to the patient's femur and tibia models to generate the patient specific profiles and curvature after the patient's femur and tibia models have been added to the atlas 130.

Figure 14:
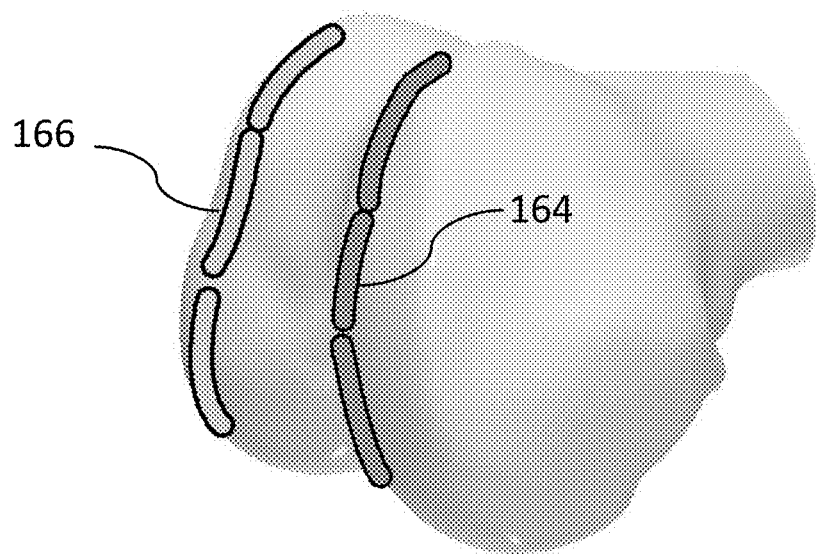
FIG. 14 is an elevated perspective view of a distal femur of an Asian showing the articulating surface approximated by three curves (per condyle).
Figure 15:
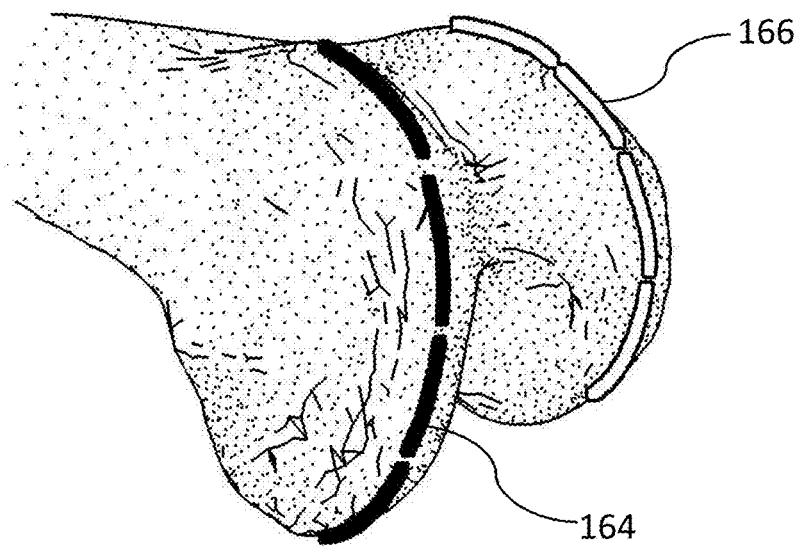
FIG. 15 is an elevated perspective view of a distal femur of a Caucasian showing the articulating surface approximated by four curves.
Figure 16:
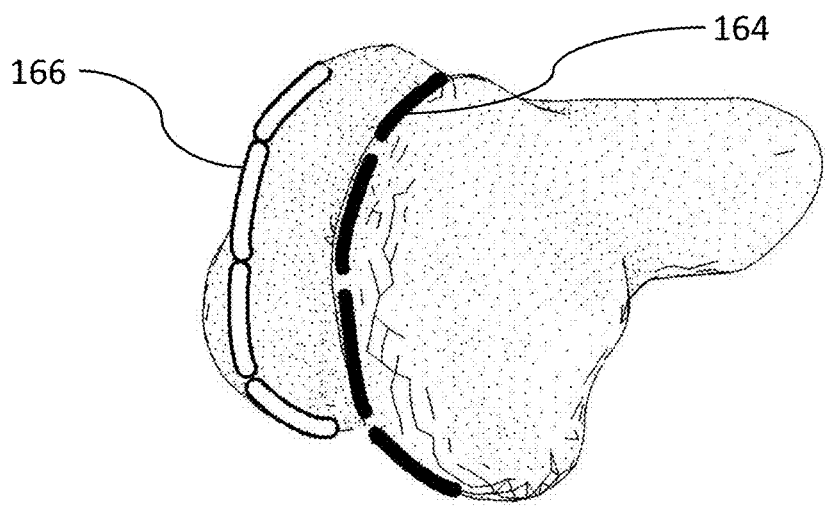
FIG. 16 is an elevated perspective view of a distal femur of an African-American showing the articulating surface approximated by four curves.

To generate the femur template curvature, the femoral surface is analyzed by the software package's atlas 130 to define the medial and lateral curvature profiles as well as the curvature of the distal femur template 160. The medial curvature profile 164 is defined by a plane created by the medial anterior point (most anterior point in medial condyle), the medial distal point (most distal point on medial condyle), and the medial posterior point (most posterior point in medial condyle). A contour profile is then generated that corresponds to the most outward protruding points on the medial condyle surface where this plane intersects the distal femur. A contour profile 166 is also generated that corresponds to the most outward protruding points on the lateral condyle surface where this plane intersects the distal femur. The resulting contour profiles 164, 166 for the medial and lateral condyles do not exhibit uniform curvature. Rather, to match the overall contour profile a series of curves are required to approximate the medial and lateral contour profiles. But the number of curves utilized to match the overall contour profile varies between ethnicities. For example, as shown in FIG. 14, three curves can be used to match the overall contour profiles 164, 166. In contrast, as shown in FIGS. 15 and 16, four curves are required to match the overall contour profiles 164, 166 for Caucasians and African Americans.

Figure 17:
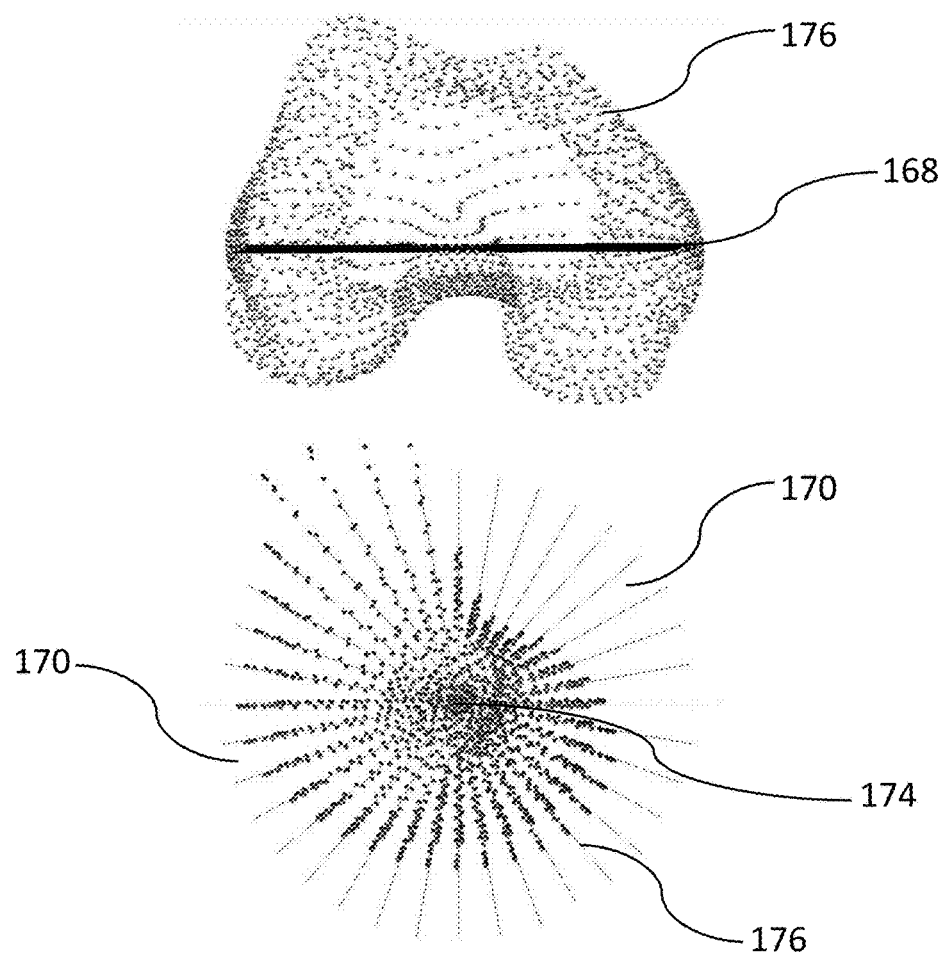
FIG. 17 is a distal view and a profile view of a point cloud representative of a distal femur articulating surface generated by a rotating chopper about the transepicondylar axis.
Figure 18:
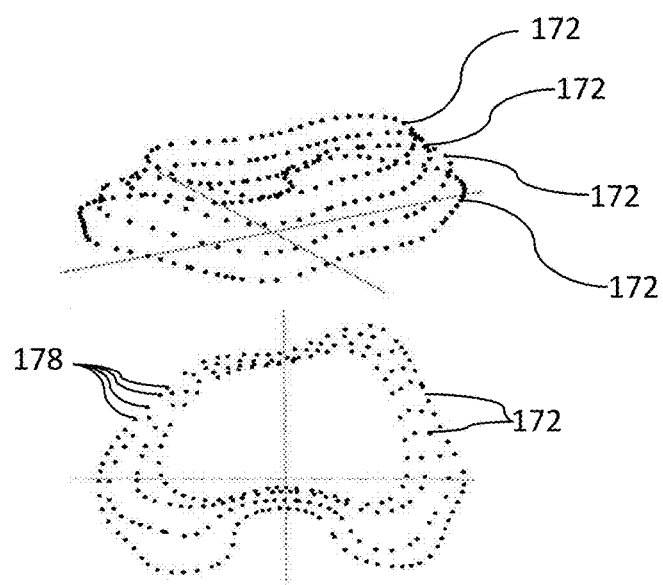
FIG. 18 is an elevated perspective view and an overhead view of a trochlear groove point cloud generated by a horizontal chopper.

Referencing FIGS. 17 and 18, the curvature of the distal femur template 160 is captured using a surface sampling operation referred to herein as a "chopper." Two choppers, one 168 rotating about a common axis extending laterally through the distal femur template to create wedge shape slices 170 and a second extending horizontally to create slices 172 having a uniform thickness, are implemented within the software package. The first rotating chopper 168 operates by rotating a plane about the transepicondylar axis 174 of the femur template 160. The distal surface points of the femur template are sampled every 10 degrees where the chopper plane intersects the bone surface, yielding points 176 collectively representative of the articulating surface curvature of the femur template 160. The horizontal chopper, in contrast to the first chopper, moves along a vertical axis and samples peripheral surface points in defined vertical 5 mm increments along the vertical axis, which yields points 178 collectively representative of the peripheral surface of the femur template.

Figure 19:
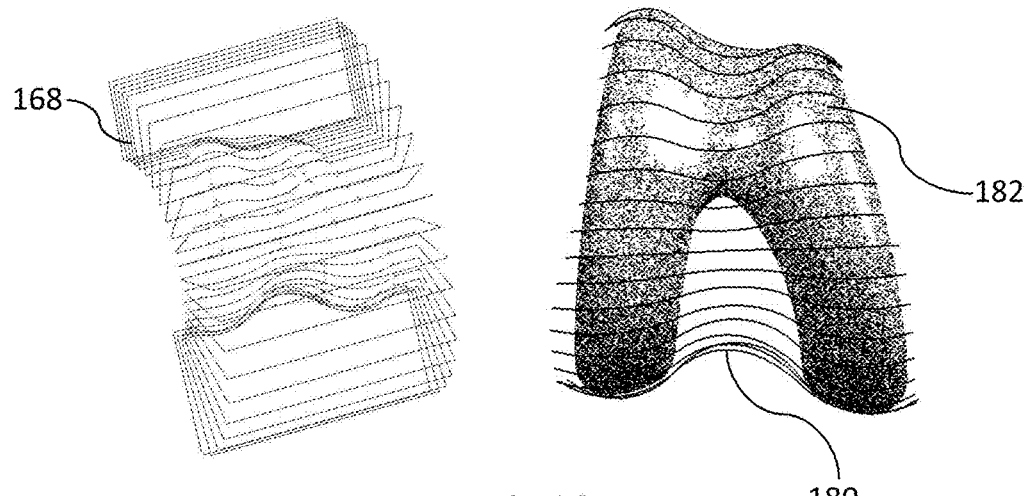
FIG. 19 is an elevated perspective view of the chopper chopping a distal femur about the transepicondylar axis and the resulting implant articulating surfaces.
Figure 20:
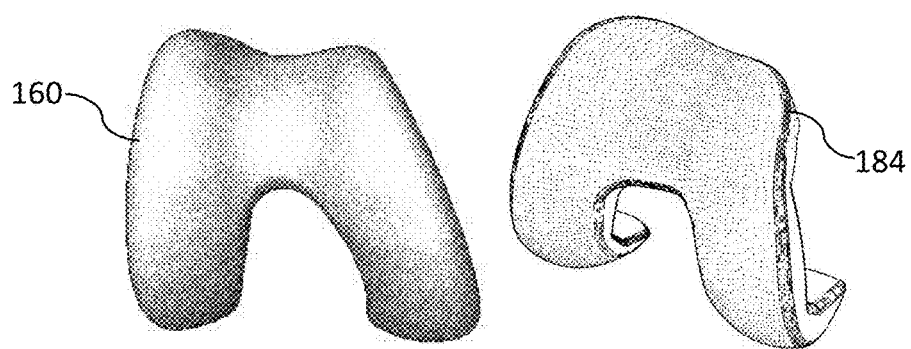
FIG. 20 is a frontal view of an Asian female template and an elevated perspective view of a total femoral implant generated using the template.
Figure 21:
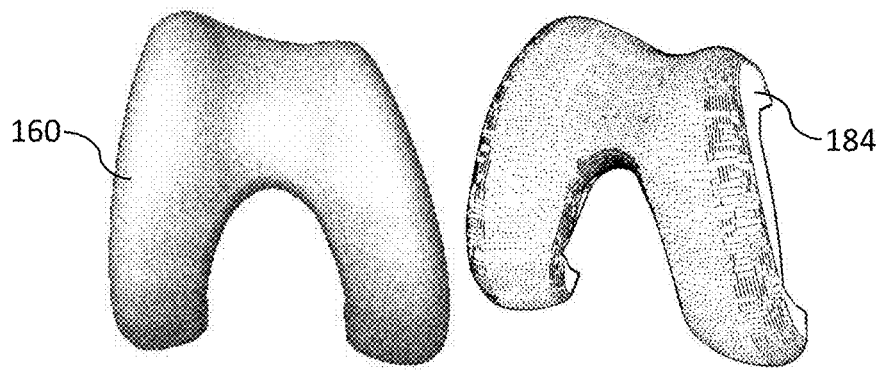
FIG. 21 is a frontal view of an African-American male template and an elevated perspective view of a total femoral implant generated using the template.
Figure 22:
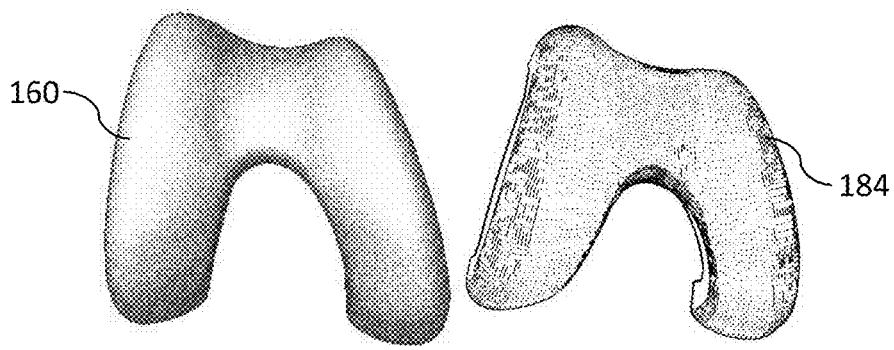
FIG. 22 is a frontal view of a Caucasian male template and an elevated perspective view of a total femoral implant generated using the template.
Figure 23:
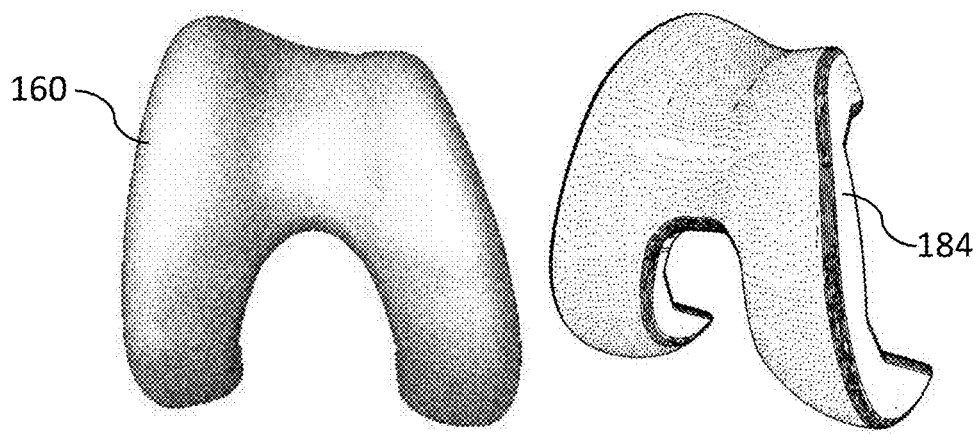
FIG. 23 is a frontal view of a Caucasian female template and an elevated perspective view of a total femoral implant generated using the template.
Figure 24:
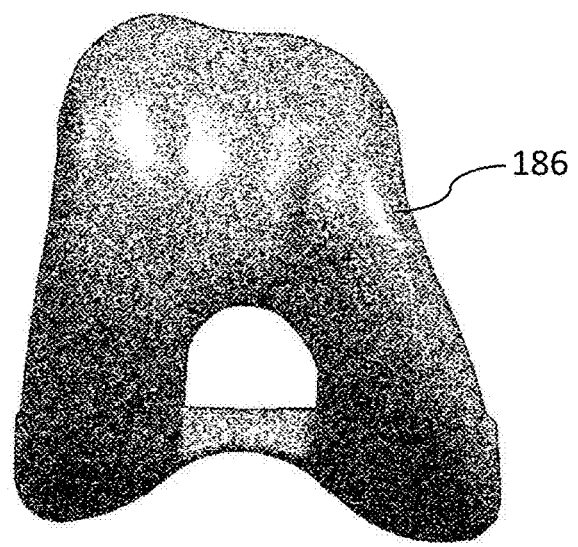
FIG. 24 is a frontal view of a posterior stabilized total femoral implant fabricated in accordance with the instant disclosure.
Figure 25:
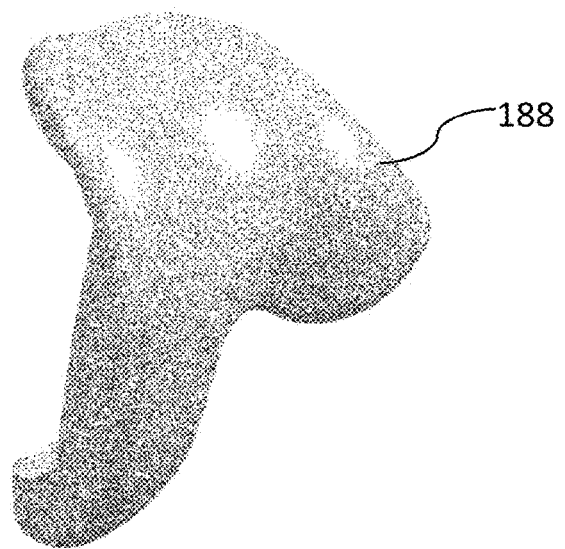
FIG. 25 is an elevated perspective view of a Caucasian male partial femoral implant fabricated in accordance with the instant disclosure.
Figure 26:
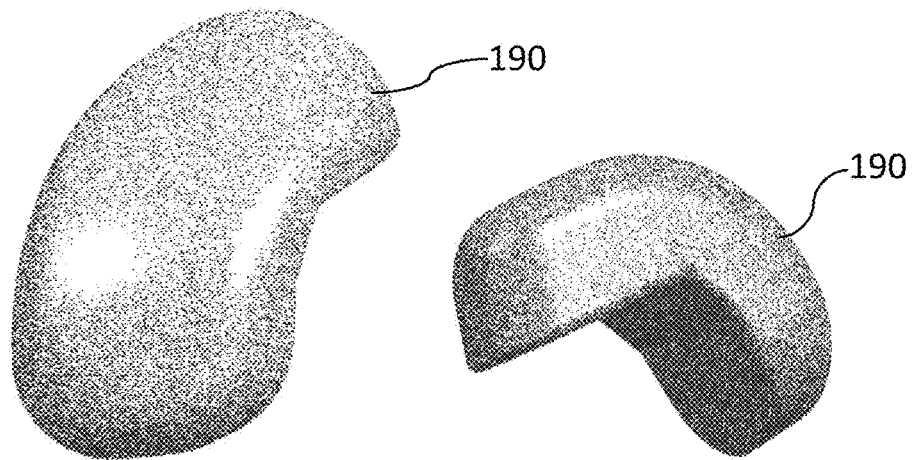
FIG. 26 is an elevated perspective view from the front and rear of a Caucasian male unilateral femoral implant fabricated in accordance with the instant disclosure.
Figure 27:
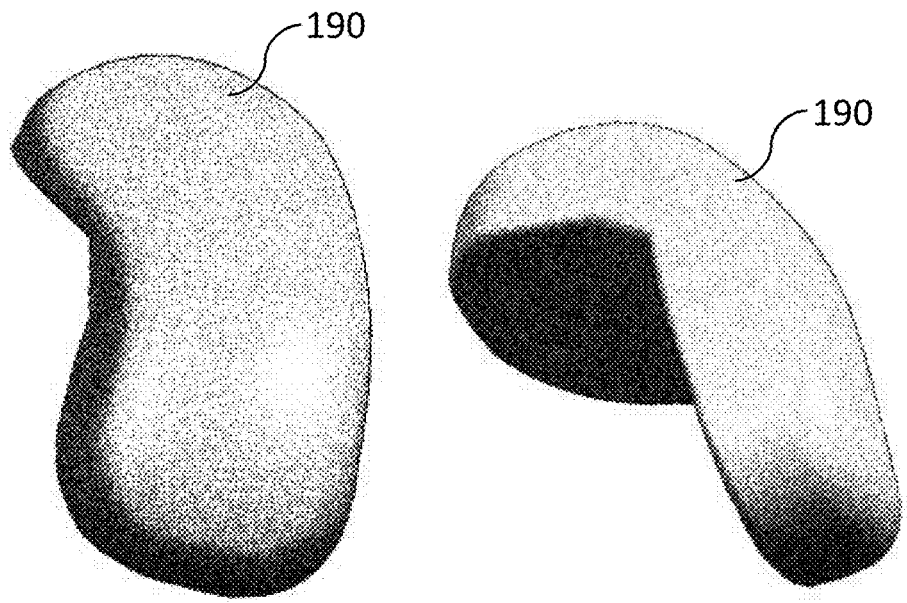
FIG. 27 is an elevated perspective view from the front and rear of an African-American male unilateral femoral implant fabricated in accordance with the instant disclosure.
Figure 28:
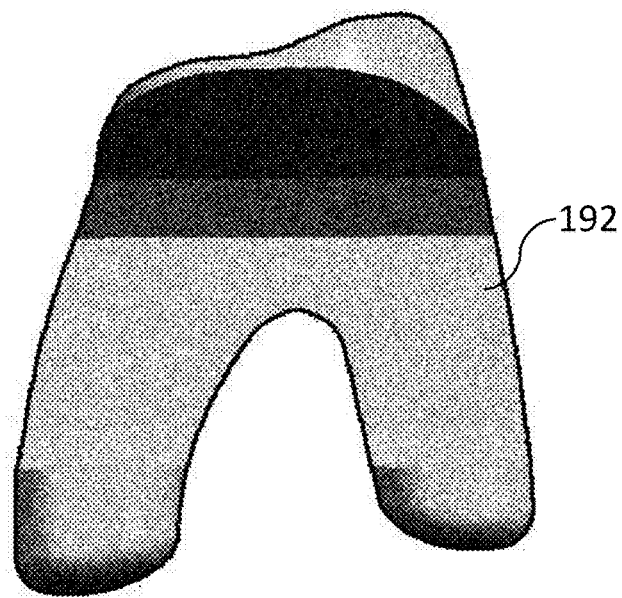
FIG. 28 is a rear, overhead view of a femoral prosthetic component having a rectangular inner surface.
Figure 29:
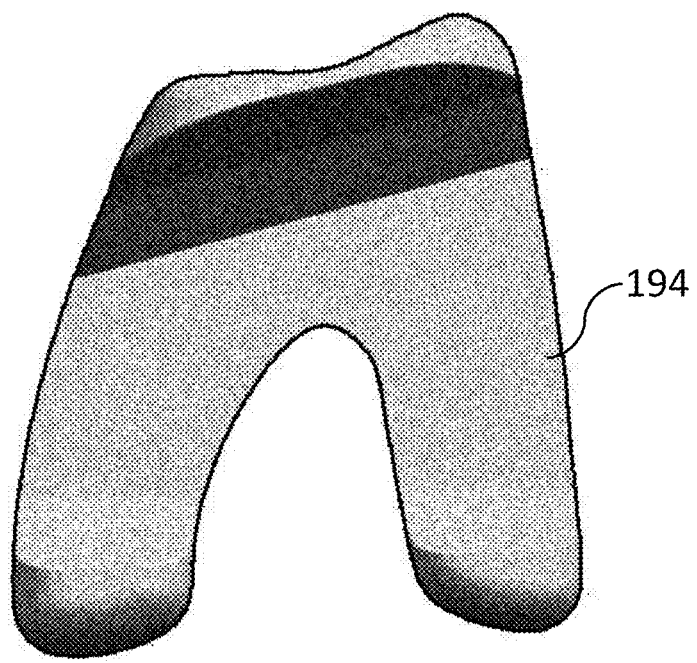
FIG. 29 is a rear, overhead view of a femoral prosthetic component having a trapezoidal inner surface.
Figure 30:
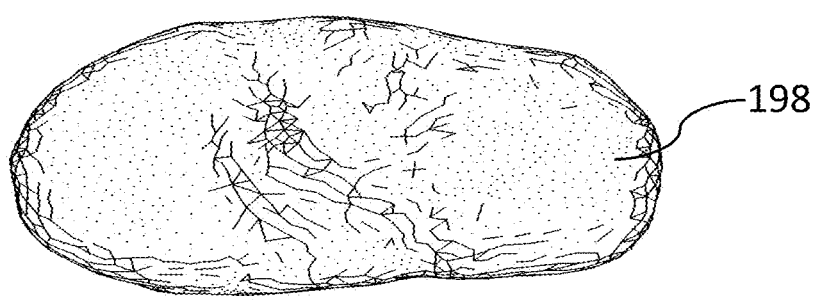
FIG. 30 is an overhead view of a proximal tibial template for an Asian male.
Figure 31:
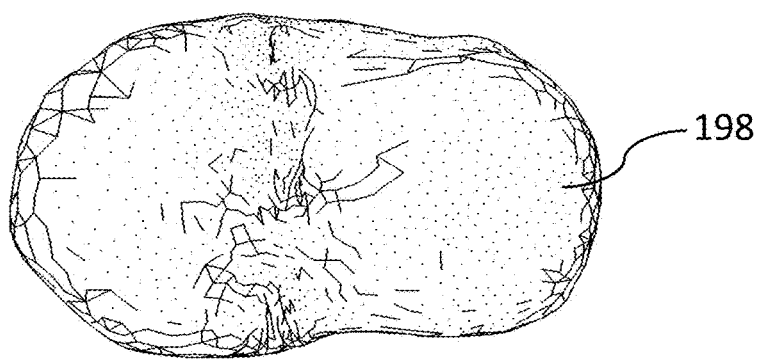
FIG. 31 is an overhead view of a proximal tibial template for an African-American female.
Figure 32:
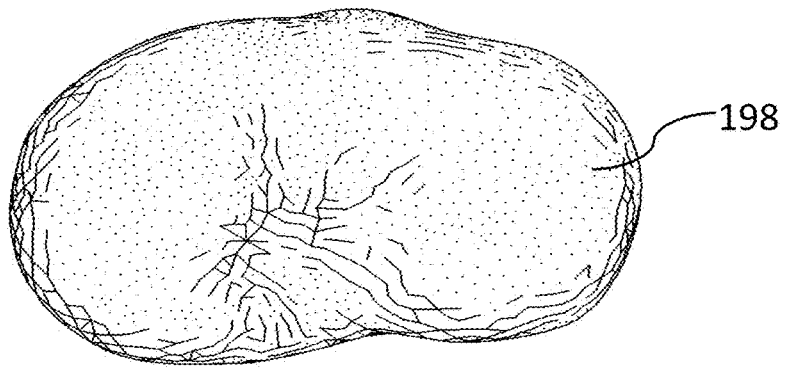
FIG. 32 is an overhead view of a proximal tibial template for a Caucasian male.

Referring to FIGS. 19-29, after the medial profile 164, lateral profile 166, and contours are extracted from the femur template 160, the contours generated by the rotating choppers 168 are parameterized with the medial and lateral profiles to create the articulating surface of the template implant. As shown in FIG. 19, to parameterize the contours, arcs 180 are fit to the points comprising each contour. After each contour is parameterized, the articulating surface 182 of the implant is generated by using the medial and lateral profiles 164, 166 to fill in the gaps between the contours, thereby resulting in a final implant 184. The same process is used to create all of the implants for each ethnicity (Caucasian, Asian, African American) and gender. Each femur template 160 may be used to create a total 184, partial 188, and/or unilateral implant 190 such as those shown in FIGS. 25-27. Moreover, the femoral implant may be created in as a cruciate retaining or a posterior stabilized version 186. And the inner surface of the mass customized femoral implant, which contacts the distal femur, may be either rectangular 192 or trapezoidal 194 (that is bone sparing).

Figure 33:
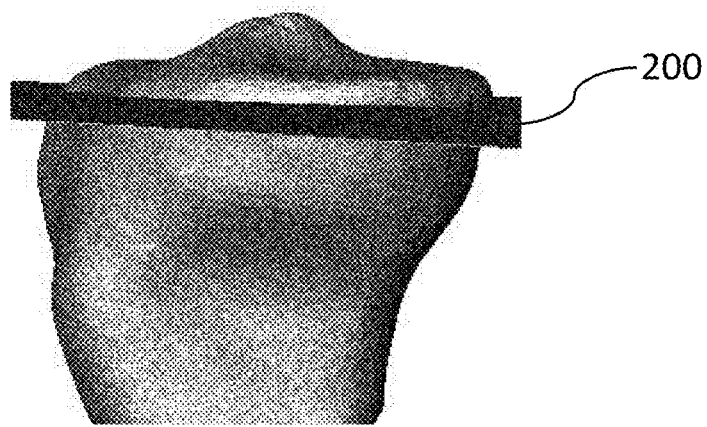
FIG. 33 is a profile view of a proximal tibial template for an African-American female, shown with the resection plane.
Figure 34:
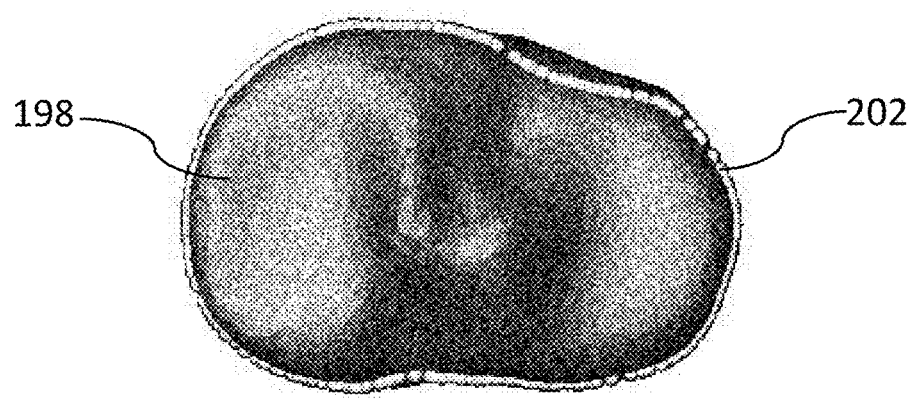
FIG. 34 is an overhead view of the proximal tibial template for an African-American female, with data points corresponding to the peripheral areas of the tibial template contacted by the resection plane.

Referencing FIGS. 30-34, the tibial implant (whether mass customized or patient specific) is divided into the tibial tray and the tray insert. The tray insert is generated from a tibia template 206. To generate the tibia template 206, representative of the condyle bearing surface shapes of the patient's tibia, the tibial surface 198 of the patient is analyzed by the software package's atlas 130 to create a plane 200 at the level of a tibial resection as shown in FIG. 33. The software package then samples points on the surface of the tibia where this plane intersects the tibial surface as shown in FIG. 34, resulting in the data points 202 outlining the periphery of the tibia at the location of the plane. The group of points 202 created from the resection plane is called the resection profile.

Figure 35:
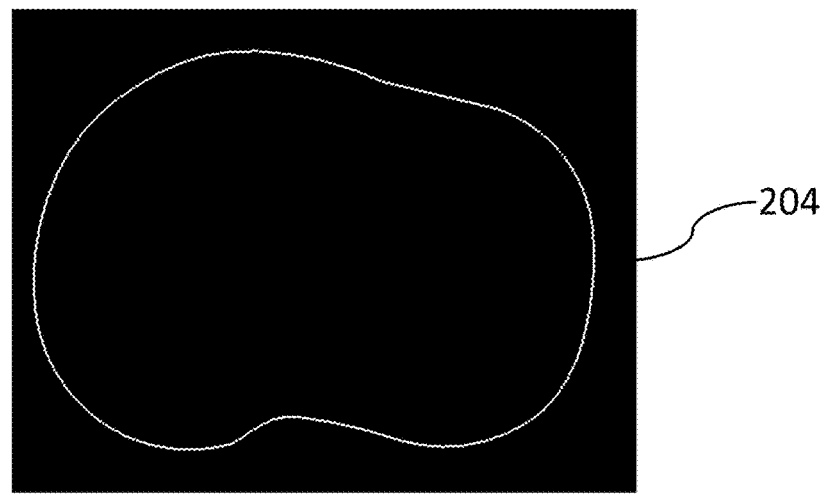
FIG. 35 is a parameterized resection profile of a tibial template.
Figure 36:
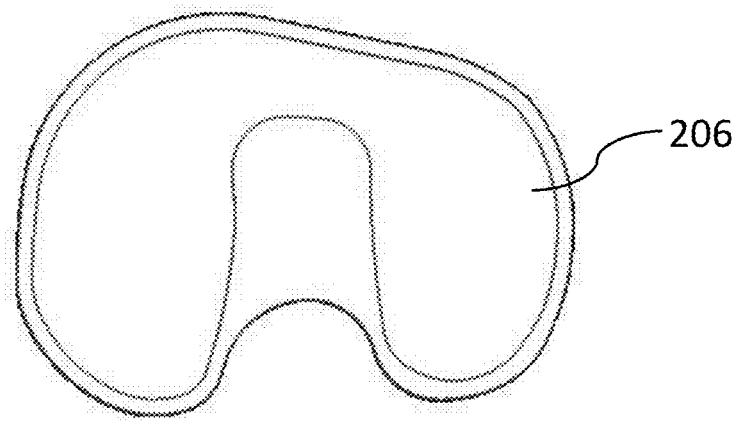
FIG. 36 is an overhead view of a Caucasian male tibial implant.
Figure 37:
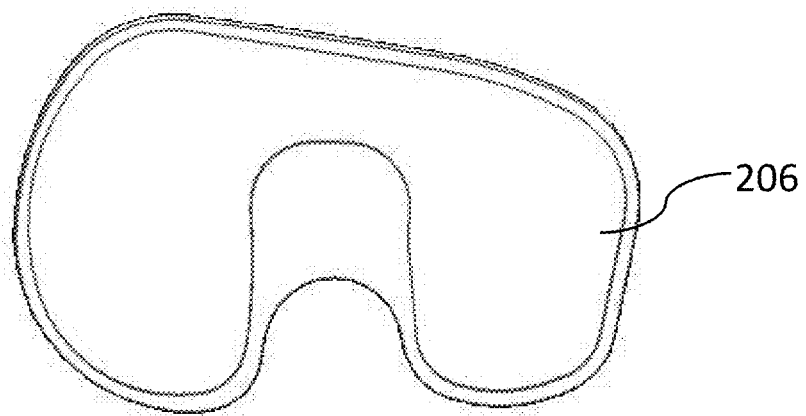
FIG. 37 is an overhead view of an African-American female tibial implant.
Figure 38:
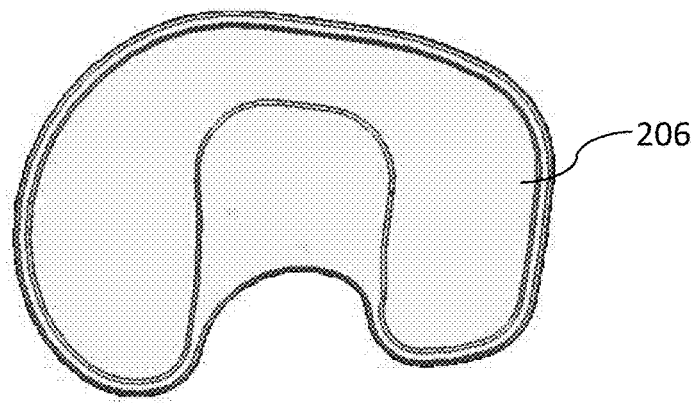
FIG. 38 is an overhead view of an Asian male tibial implant.

Referring to FIGS. 35-38, the resection profile 202 is then fit with curves to create a parameterized profile 204, such as shown in FIG. 35. The tibia template 206 is then generated from the parameterized profile 204 as shown in FIGS. 36-38 for three ethnicities. The inside edge and depression of the tibial template 206 are made to match a tibial tray (not shown). The tibial template is available as a unilateral component or as a total component.

Figure 39:
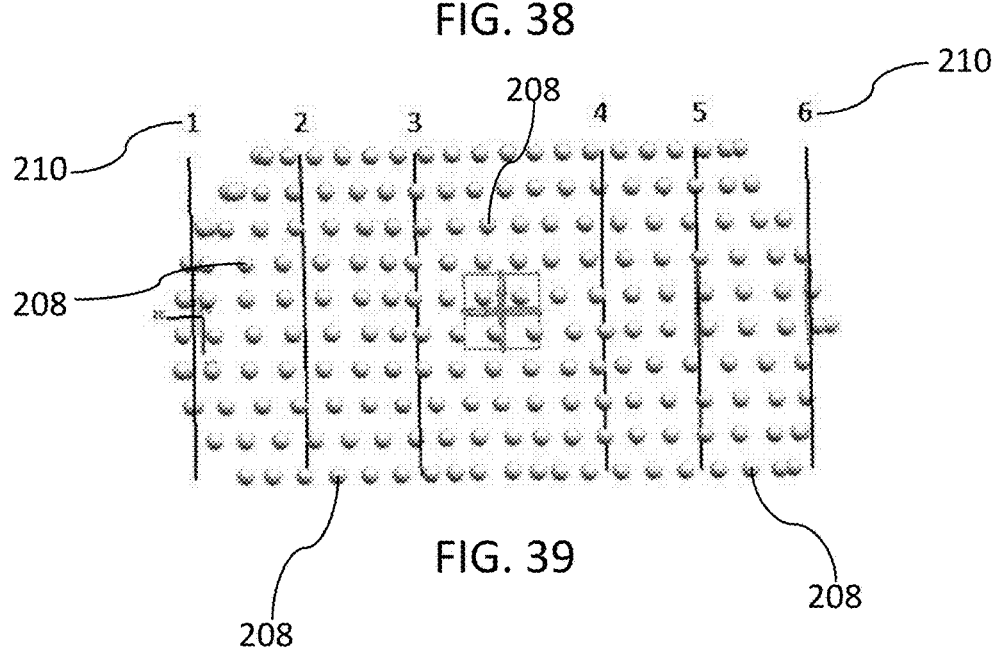
FIG. 39 is an overhead view of a articulating surface point cloud for a proximal tibia divided into six regions.
Figure 40:
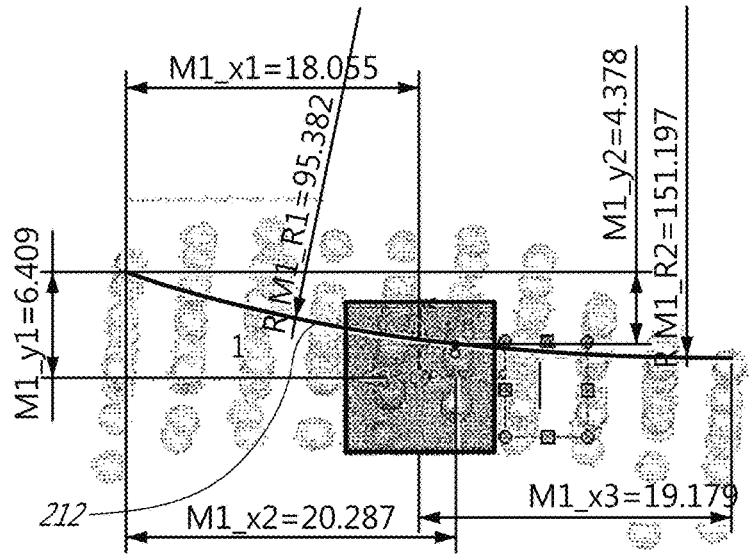
FIG. 40 is shows a curve parameterizing the contour of tibia surface region 1 of FIG. 39.
Figure 41:
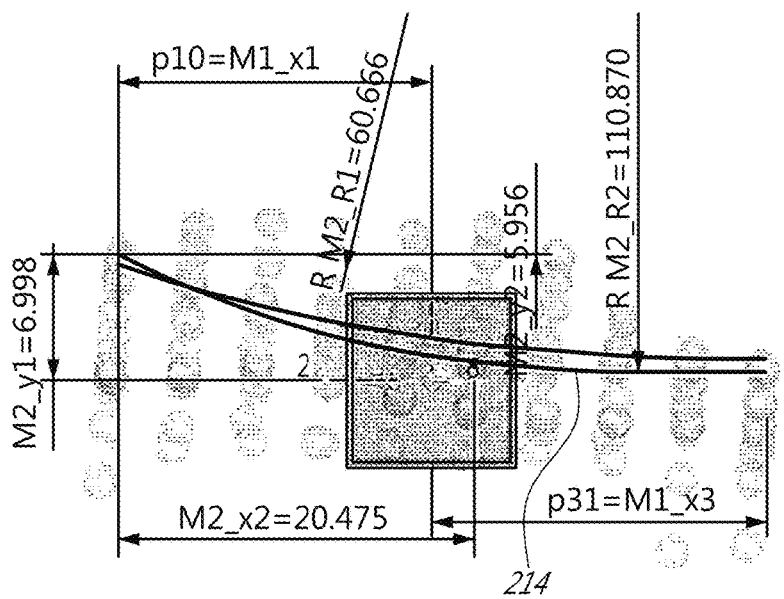
FIG. 41 is shows a curve parameterizing the contour of tibia surface region 2 of FIG. 39.
Figure 42:
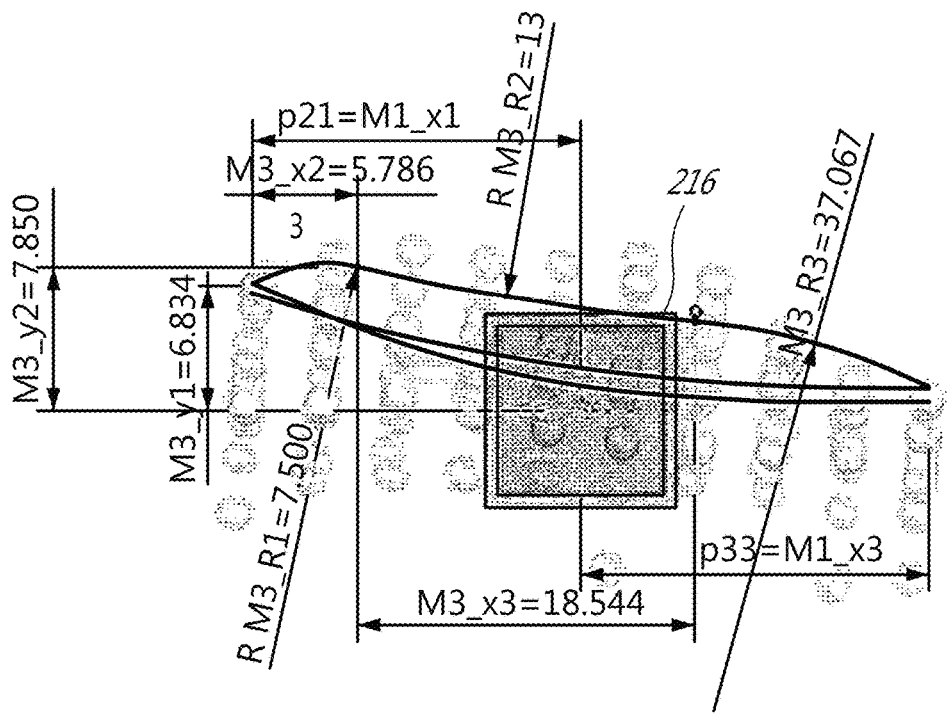
FIG. 42 is shows a curve parameterizing the contour of tibia surface region 3 of FIG. 39.
Figure 43:
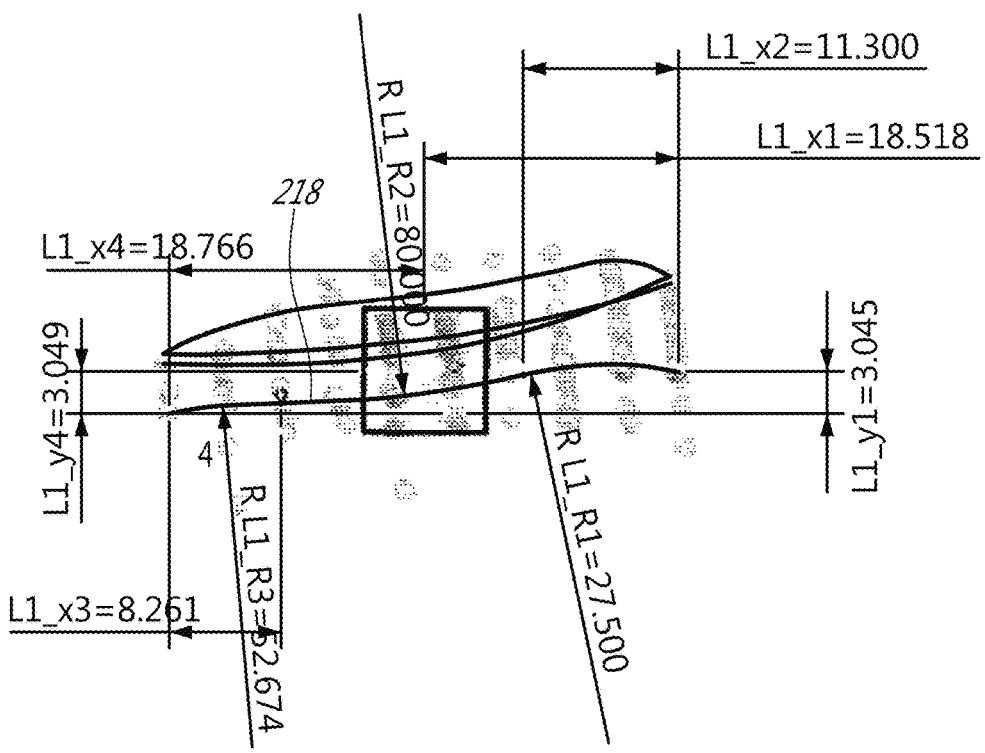
FIG. 43 is shows a curve parameterizing the contour of tibia surface region 4 of FIG. 39.
Figure 44:
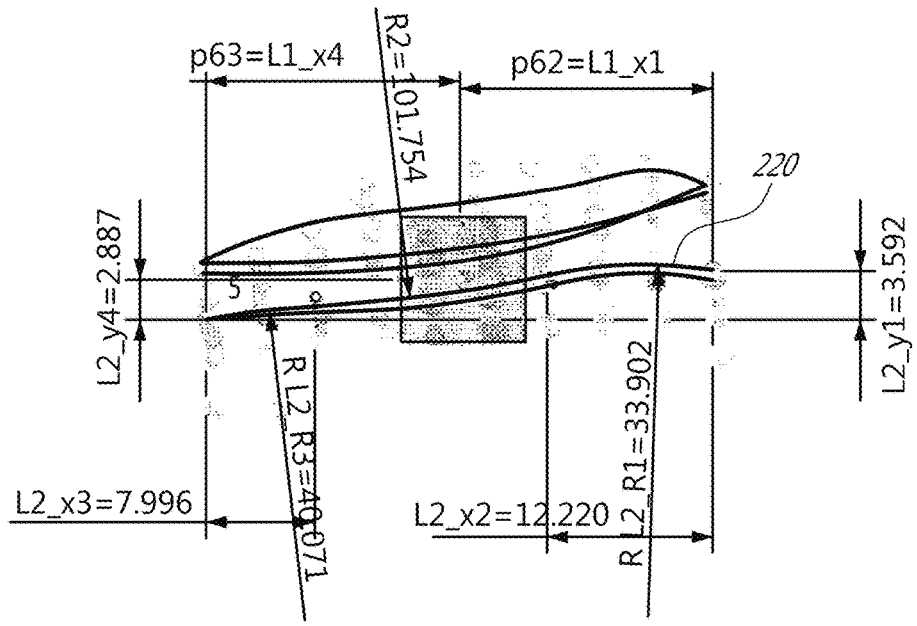
FIG. 44 is shows a curve parameterizing the contour of tibia surface region 5 of FIG. 39.
Figure 45:
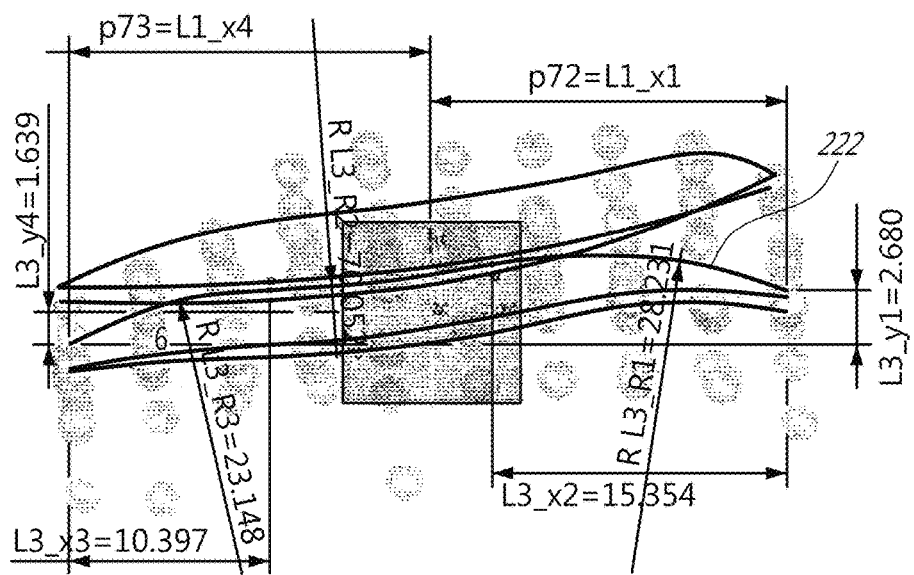
FIG. 45 is shows a curve parameterizing the contour of tibia surface region 6 of FIG. 39.
Figure 46:
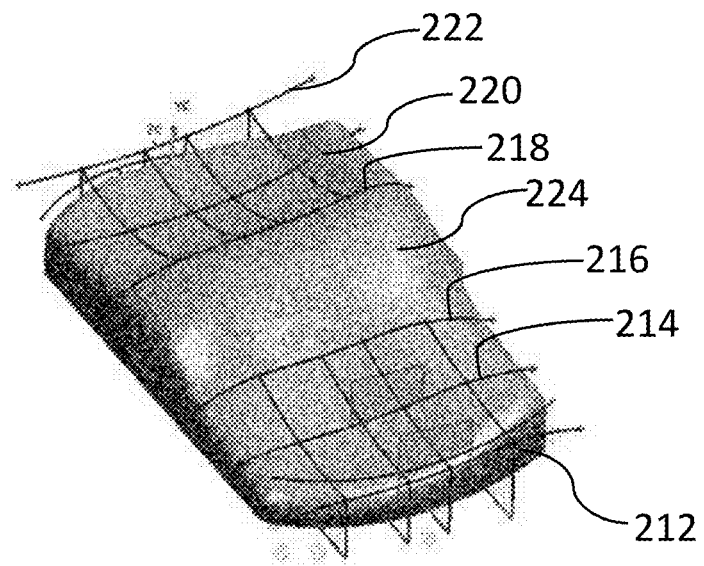
FIG. 46 is an elevated perspective view of a tibial tray insert generated from the parameterized curves of FIGS. 40-45.
Figure 47:
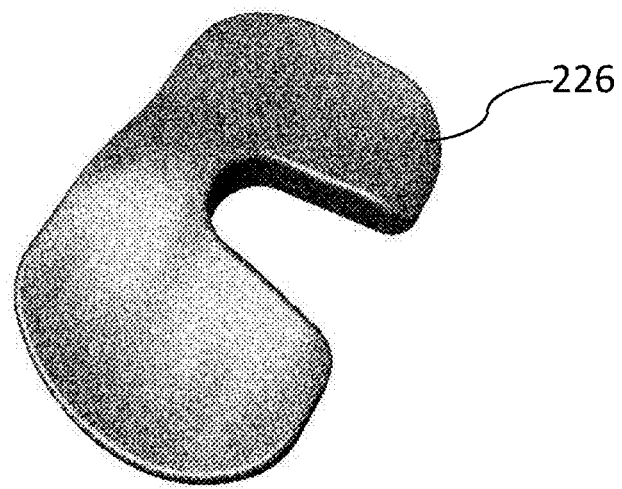
FIG. 47 is an elevated perspective view of a tibial tray insert for a cruciate retaining knee system generated from the parameterized curves of FIGS. 40-45.
Figure 48:
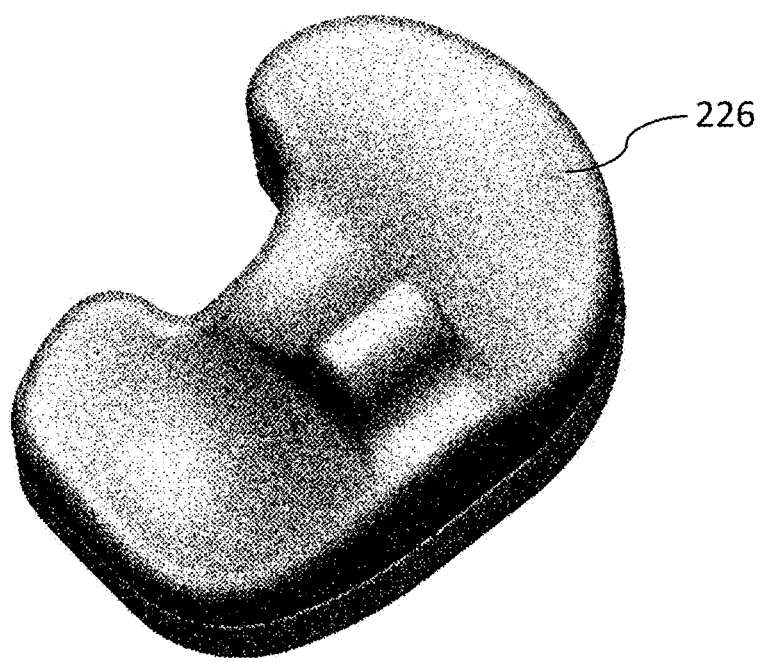
FIG. 48 is an elevated perspective view of a tibial tray insert for a posterior stabilized knee system generated from the parameterized curves of FIGS. 40-45.
Figure 49:
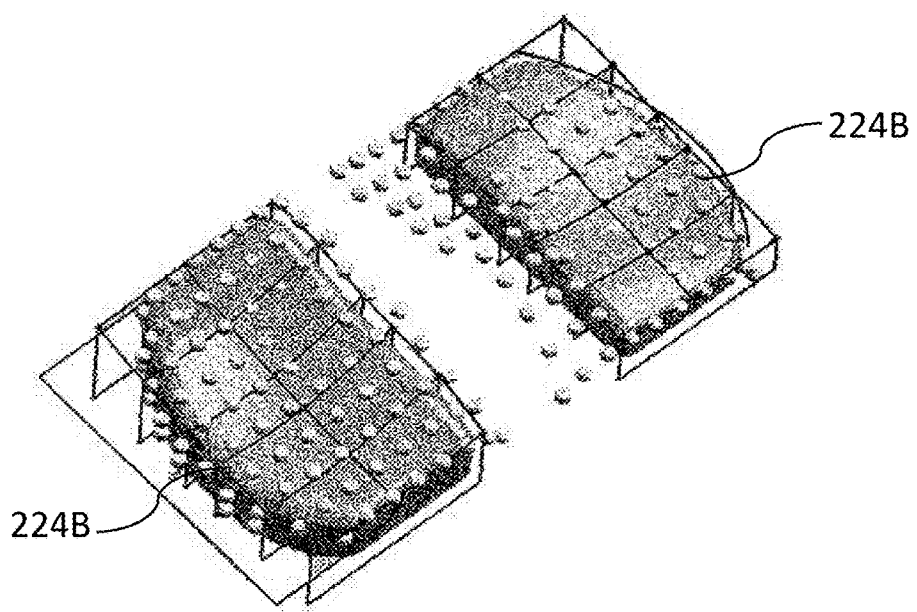
FIG. 49 is an elevated perspective view of a medial tibial bearing insert and a lateral tibial bearing insert generated from the parameterized curves of FIGS. 40-45.
Figure 50:
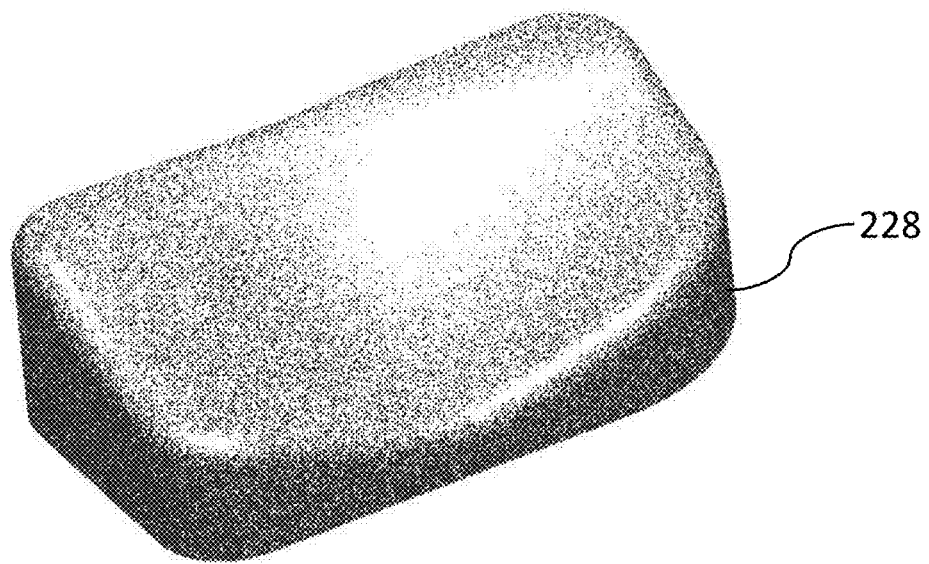
FIG. 50 is an elevated perspective view of a medial tibial bearing insert generated from the parameterized curves of FIGS. 40-45.
Figure 51:
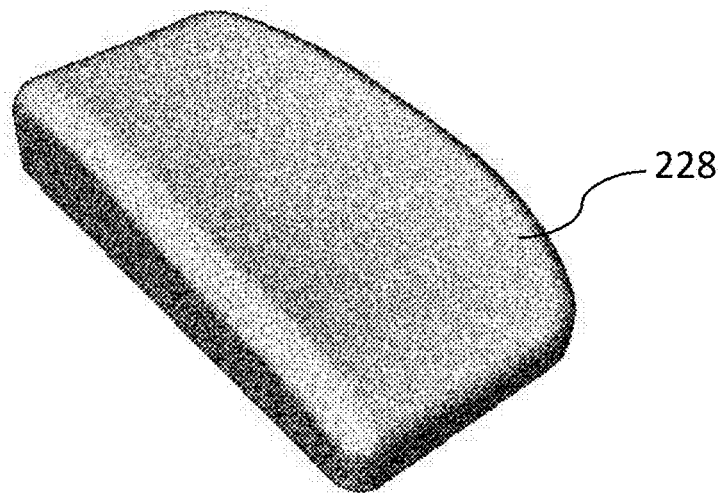
FIG. 51 is an elevated perspective view of a lateral tibial bearing insert generated from the parameterized curves of FIGS. 40-45.

Referencing FIGS. 39-51, the articulating surfaces of the tibial template 206 are analyzed by first processing them with the horizontal chopper to sample the surfaces as a set number of points, such as shown in FIG. 39, to generate a series of points 208 representative of the contours of the articulating surfaces. The articulating surfaces of the tibial template 206 are then each divided into six regions 210 fit by respective curves 212-222, as shown in FIGS. 39-45. The curves parameterize the tibial template 206 articulating surfaces so that the tibial tray insert 224 may be generated, as shown in FIG. 46. The tray insert 224 may be created for total 226 (see FIGS. 47 and 48) or for unilateral 228 (see FIGS. 49-51) tibial implants. The medial tray insert component 224A is created from curve regions 1, 2, and 3 while the lateral tray insert 224B component is created from curve regions 4, 5 and 6 (see FIG. 49). The total tray insert is generated from all six curve regions. The total tray insert 226 is also available for posterior stabilized (see FIG. 48) and cruciate retaining (see FIG. 47) knee systems.

Figure 52:
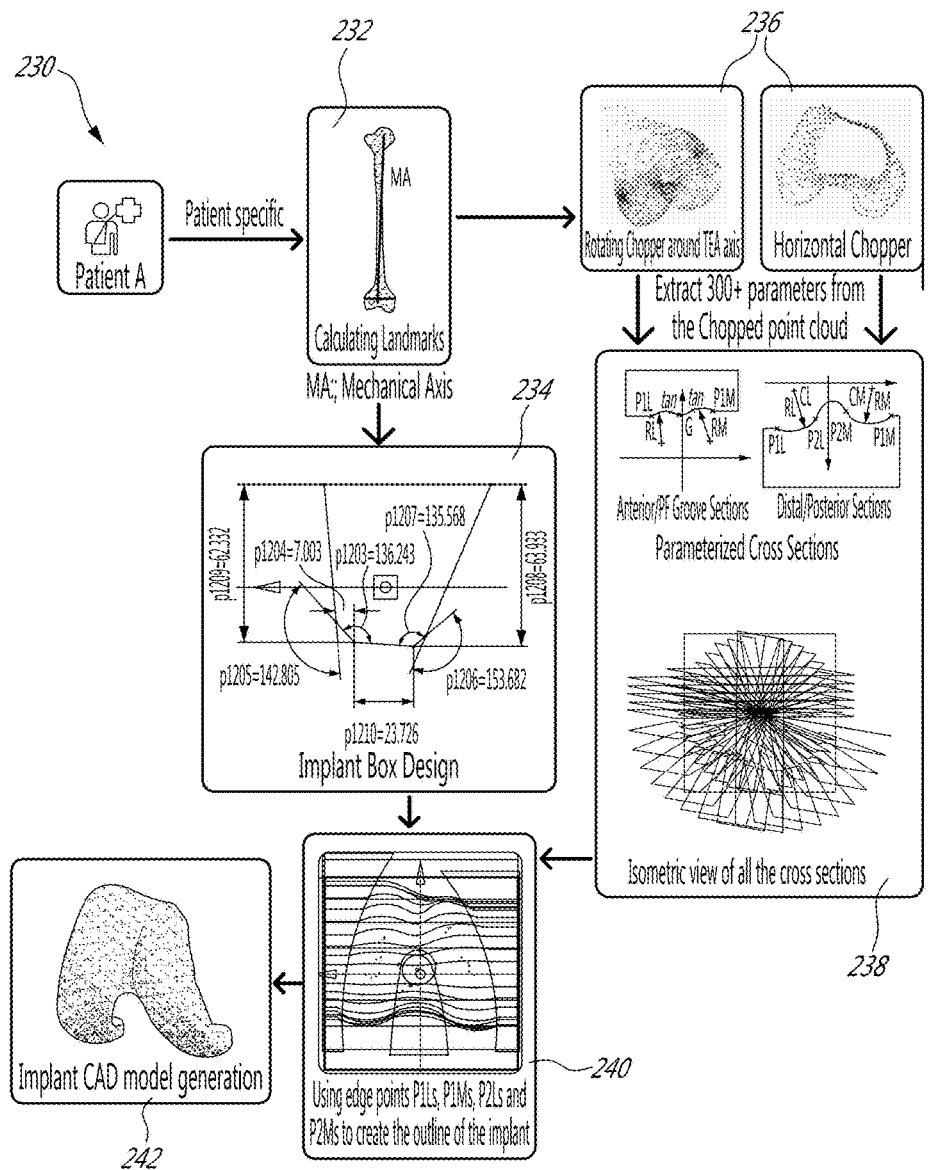
FIG. 52 a schematic diagram of a patient specific implant generation sequence in accordance with the instant disclosure.
Figure 53:
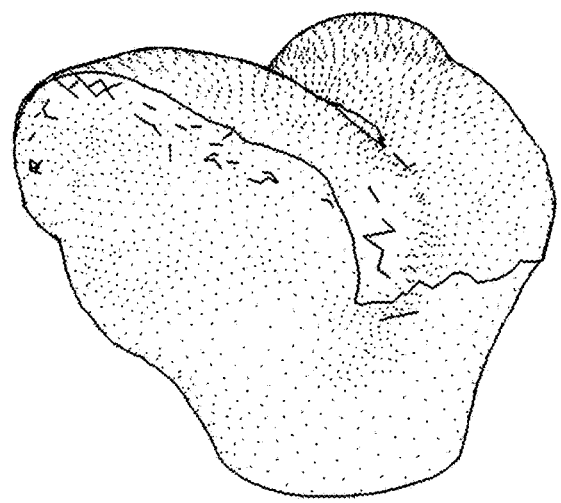
FIG. 53 is an elevated perspective view of a distal femur shown with cartilage prior to contoured resection.

Referring to FIG. 52, a similar process 230 to the one described previously for creation of mass customized implants is used to create patient specific implants. While the mass customized implant process uses the patient's bones to determine the size of the implant to be assigned, the patient specific process 230 generates the implant directly from the patient's bone (i.e., bone model). As shown in FIG. 52, the patient's bones are added to the software package's atlas 232, where the atlas calculates the measurement landmarks for each bone. The calculated landmarks are used to create the implant box 234, which is the inner surface of the implant that contacts the patient's resected bone. The articulating surface of the patient's bone is analyzed 236 to extract the patient's bone curvature and profile information. The method of curvature analysis is the same as that used to create the mass customized implants and will not be repeated for purposes of furthering brevity. The patient's bone curves and profiles are then parameterized 238 to generate the implant's articulating surfaces for both the femoral and tibial components. The calculated patient specific implant box 234 and articulating surfaces are combined 240 with the articulating surfaces to create the final patient specific implant 242.

Figure 54:
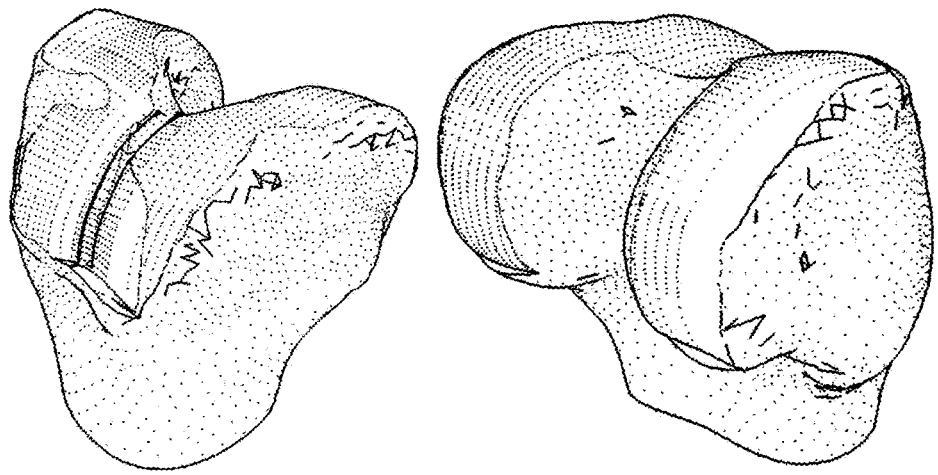
FIG. 54 is an elevated perspective view of an anterior and a posterior distal femur shown without cartilage subsequent to contoured resection.

Referring to FIGS. 28, 29, 53, and 54, by way of explanation, the femoral component inner box of the patient specific implant may be rectangular, trapezoidal, or contoured to match the patient's resected distal femur, as shown in FIG. 54. As discussed in more detail hereafter, novel instrumentation and techniques were developed to provide the contoured distal femur resection (that includes cartilage removal) to accept the inner surface of the contoured patient specific implant.

Figure 55:
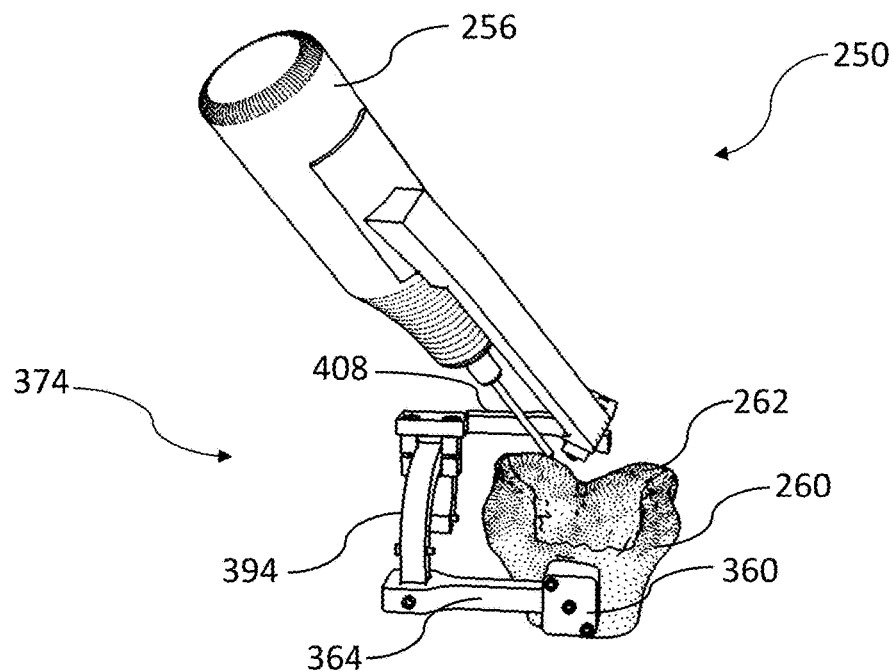
FIG. 55 is an elevated perspective view of an exemplary resection guide in accordance with the instant disclosure.
Figure 56:
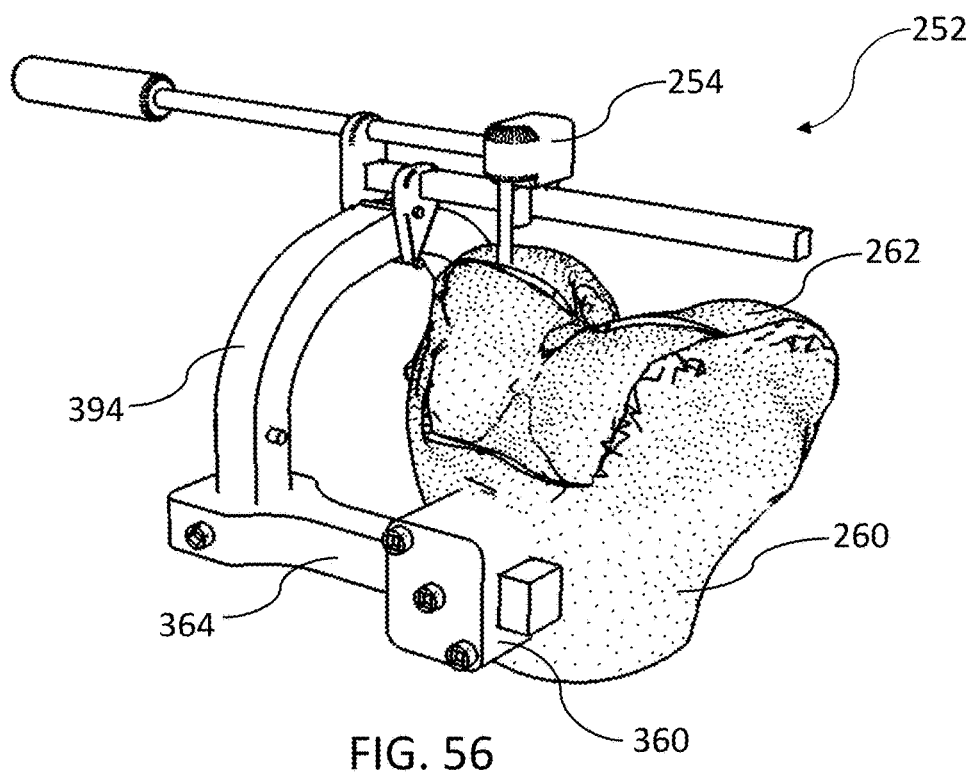
FIG. 56 is an elevated perspective view of a second exemplary resection guide and microsurgical robot in accordance with the instant disclosure.

Referencing FIGS. 55 and 56, the patient specific instrumentation comes in two varieties. The first variety, a free form femoral cutting guide 250 (see FIG. 55), controls the motion of a standard surgical drill along a pair of tracks. The shape of the tracks is derived from the profiles and contours of the patient's femoral anatomy. The second variety, a microsurgical robot guide 252 (see FIG. 56), is a more advanced instrument that makes use of a microsurgical robot 254 that is aware of its position with respect to the femur. The microsurgical robot guide 252 makes use of a physical track to guide motion of the microsurgical robot 254 from the anterior to posterior of the femur. Like the free form femoral cutting guide 250, the track of the microsurgical robot guide 252 is generated from the profiles of the patient's femur. As the microsurgical robot 254 travels over the surface of the femur, it adjusts its cutting depth to follow the contour of the femur, allowing the cartilage and some bone to be removed.

Referring to FIGS. 55 and 57-63, the free form femoral cutting guide 250 serves as a non-powered framework to guide a standard surgical drill 256 along an anatomically defined pathway that results in removal of cartilage 258 from the distal femur 260 thereby leaving a resurfaced portion 262 suitable for a conformal femoral implant. After the patient's femoral bone model has been generated, the software package uses this femoral bone model to generate the free form femoral cutting guide 250. The free form femoral cutting guide 250 is mounted to a bone-mounted base component 264, which is positioned with respect to the patient's femur 260 using a patient specific jig. To prepare the patient's distal femur 260 to accept the orthopaedic implant, the surgeon slides the surgical drill 256 along a pair of interlocked tracks. A first track 266 controls motion in the anteroposterior (AP) direction (see FIG. 59) and a second track 268 controls motion in the mediolateral (ML) direction (see FIG. 60). Combining both motions results in the removal of cartilage from the area of the distal femur 260 for unilateral (see FIGS. 61 and 62) or total (see FIG. 63) knee arthoplasty.

The free form femoral cutting guide 250 includes several components. Among these components are: (1) a segmented femur with cartilage model 270; (2) a medial AP track; (3) a medial ML track; (4) a lateral AP track; (5) a lateral ML track; (6) a sulcus AP track; (7) a sulcus ML track; (8) a track slider; (9) a fixation arm; (10) a base component; and, (11) a patient specific jig.

Figure 57:
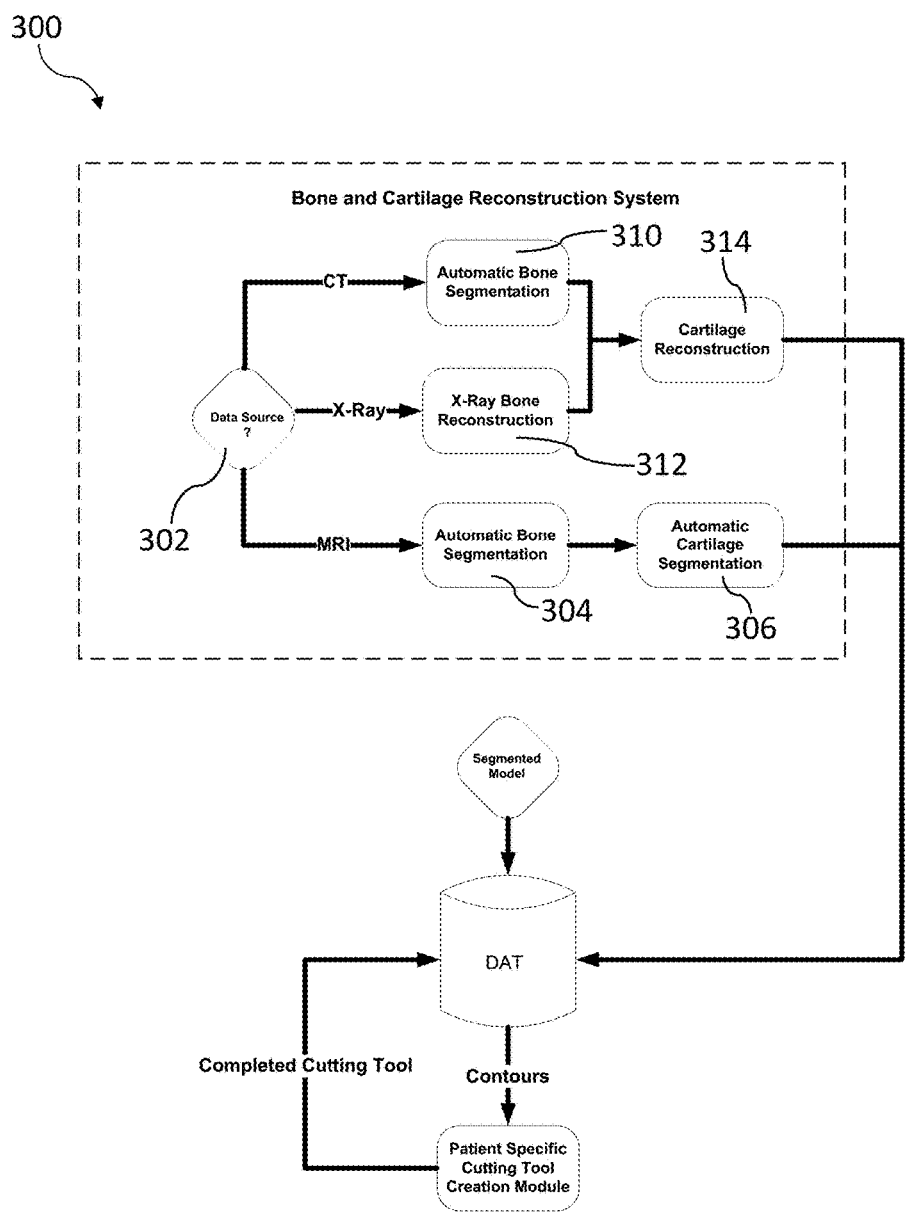
FIG. 57 is a schematic diagram of a system overview for constructing a patient specific cutting jig.
Figure 58:
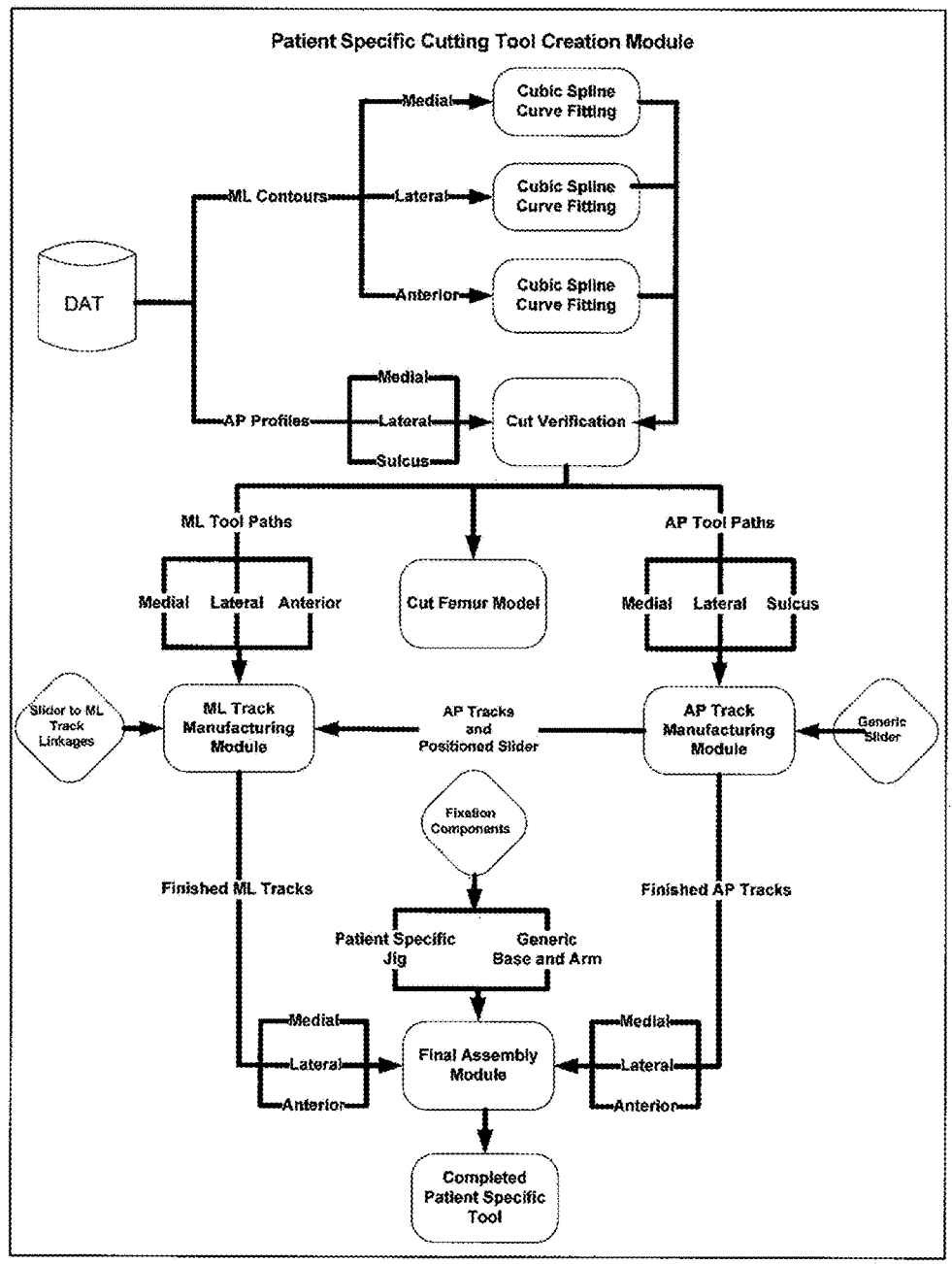
FIG. 58 is a schematic diagram of the patient specific cutting tool creation module of FIG. 57.
Figure 59:
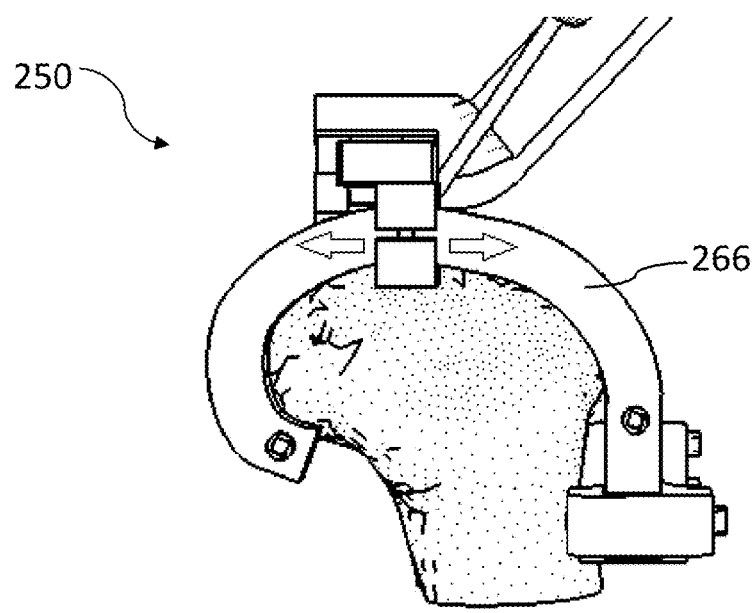
FIG. 59 is a profile view of an exemplary anterior-posterior cutting guide showing traversal of a medial-lateral cutting guide along the anterior-posterior cutting guide in the anterior-posterior direction.
Figure 60:
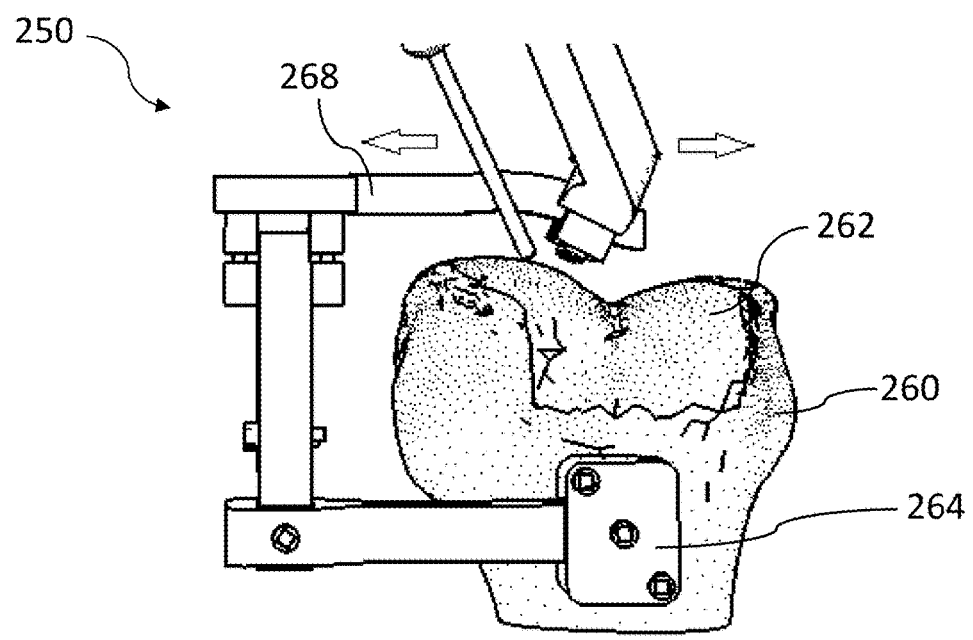
FIG. 60 is a rear view of the exemplary anterior-posterior cutting guide and medial-lateral cutting guide, showing traversal of a cutting device in the medial-lateral direction along the medial cutting guide.
Figure 61:
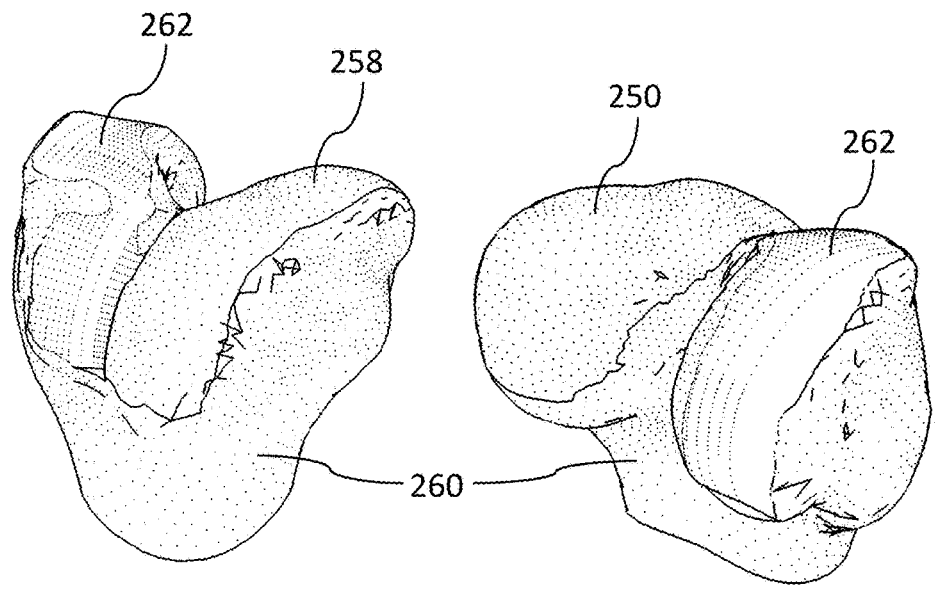
FIG. 61 is an anterior and a posterior view of a distal femur after medial cartilage removal.
Figure 62:
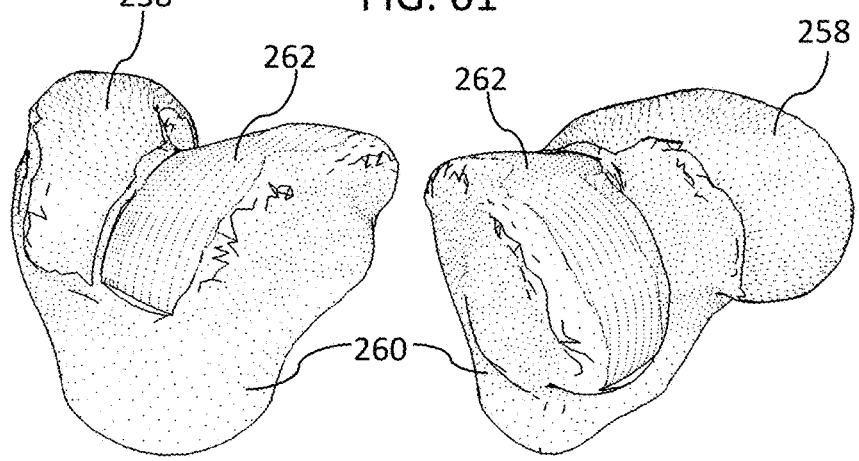
FIG. 62 is an anterior and a posterior view of a distal femur after lateral cartilage removal.
Figure 63:
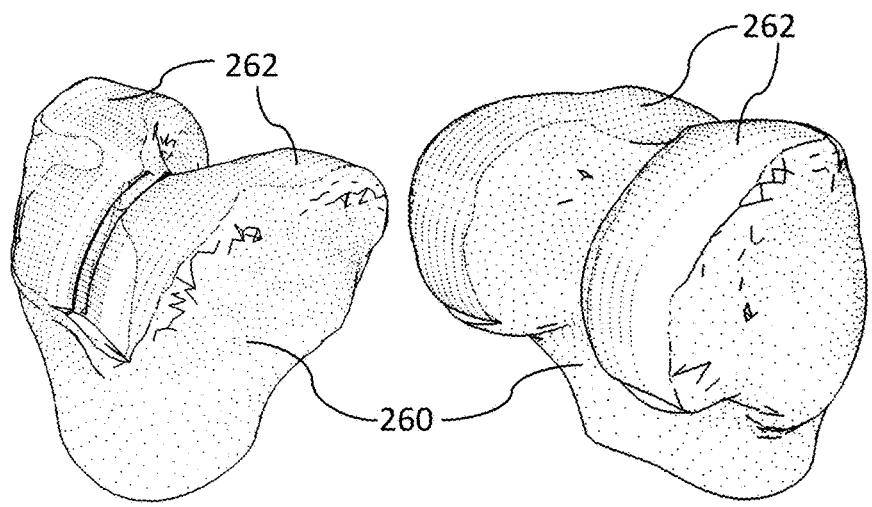
FIG. 63 is an anterior and a posterior view of a distal femur after medial and lateral cartilage removal.

Referring to FIGS. 57 and 58, an exemplary process 300 for constructing the femur with cartilage model 270 starts with using any number of imaging modalities as a data source 302 including, without limitation, CT, X-rays, and MRI. To create the femur with cartilage model 270 using MRI, a scan of the patient's knee is acquired from which DICOM files are obtained. These DICOM files (that include bone and cartilage) are then automatically segmented 304, 306 (i.e., sliced) by the software package to create surface models of the patient's femur. The surface models are then added to a principal component-based statistical bone atlas to generate the femur with bone cartilage model. This femur with cartilage bone model may be added to the atlas and used to generate the necessary profiles without further processing.

To create the femur with cartilage model using CT images, the patient's knee is scanned and the resulting DICOM files are obtained. These DICOM files are automatically segmented 310 by the software package. But because cartilage information is not captured in CT images, additional processing is required to estimate this tissue, which will be discussed hereafter.

To generate a femur with cartilage model using X-rays, the patient is fitted with a registration brace and then bi-planar X-rays are taken of the patient's knee. Thereafter, an X-ray bone reconstruction task 312 is carried out that includes creation of the surface model of the patient's bone from bi-planar X-rays. This task includes taking the X-ray images and an average bone from a principal component based statistical bone atlas and placing them in a three dimensional (3D) scene. An initial pose is then defined by a user of the software package and the average bone shape, translation, and rotation are optimized through a genetic algorithm and 2D-to-3D scoring metric. After convergence is reached, the resultant surface model generated from the atlas model is representative of the patient's femoral geometry. As with CT, additional processing is required to estimate the patient cartilage.

X-ray and CT modalities require a cartilage reconstruction process 314 to generate an estimated cartilage model to be applied to the distal femur surface model. This cartilage model is derived from cartilage tissue segmented from MRI data. After the femoral surface model of the patient has been created, the cartilage model is scaled by the software package to fit the patient's femoral surface model and then applied to the femoral surface model. After cartilage is added to the femoral surface model, AP profiles and ML contours may then be generated by the software package.

A more detailed discussion of some of the features shown in FIGS. 57 and 58 may be found in U.S. patent application Ser. No. 13/203,010, entitled, "INTELLIGENT CARTILAGE SYSTEM," the disclosure of which is incorporated herein by reference.

Figure 64:
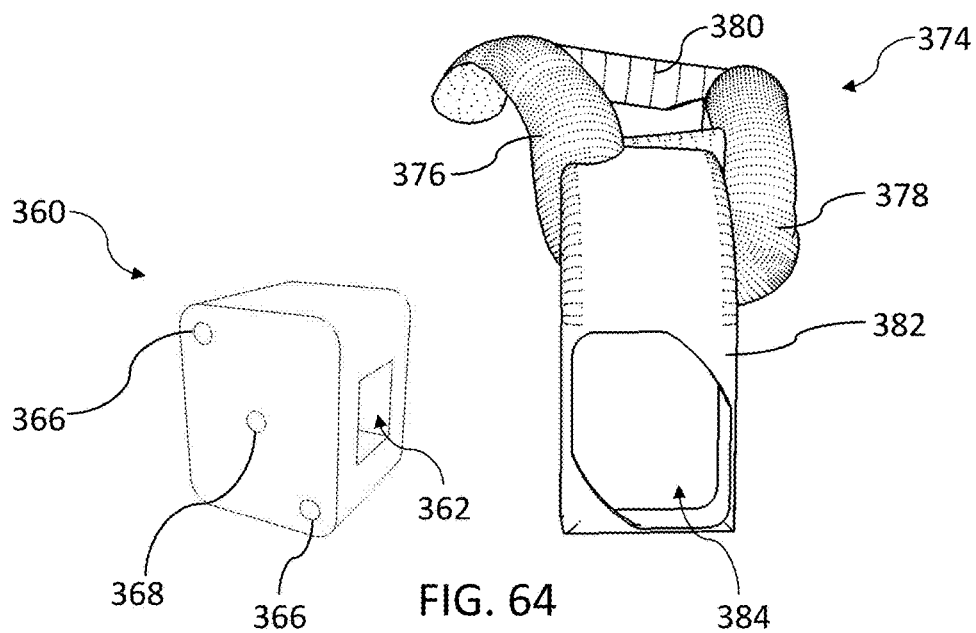
FIG. 64 is an elevated perspective view of an exemplary base and an exemplary position jig for the base.

Referring to FIG. 64, in order to prepare the patient's distal femur 260 to receive the orthopaedic implant, the distal end of the femur must be processed. Processing of the distal femur includes recontouring the distal end of the femur 260 to remove certain cartilage, thus allowing the orthopaedic implant to directly contact bone. In order to begin this process, a base 360 is mounted to the anterior femur 260, proximate the distal end. This base 360 provides a foundation to which the guides of the cutting tool are mounted. In exemplary form, the base 360 comprises a rectangular block (six sided) having a through cavity 362 with a rectangular cross-section that extends from the medial side to the lateral side. As will be discussed in more detail hereafter, the through cavity 362 is adapted to accommodate insertion of at least a portion of a horizontal arm 364. The base 360 also includes three through cavities 366, 368, each having the same circular cross-section and oriented normal to the rectangular through cavity. The three through cavities 366, 368 are oriented along a diagonal line that extends across opposing top and bottom surfaces of the base. The through cavities 366 at the end of the diagonal line are adapted to accept bone screws 370 that operate to couple the base 360 to the anterior femur 260. The middle through cavity 368 is adapted to receive a set screw 372 used to lock the horizontal arm 364 within the rectangular through cavity 362.

In this exemplary embodiment, the base 360 is fabricated from high density polyethylene. But those skilled in the art will realize the other materials may be used to fabricate the base including, without limitation, titanium, stainless steel, ceramics, and other biologically inert materials.

In order for the base 360 to be useful during the cutting process, the base must be mounted to the anterior femur 260. In order to accurately position the base 360 with respect to the femur 260, a patient-specific placement guide 374 is created by the software package that includes a pair of arcs 376, 378 that are shaped to overly and match the patient's native distal femur (i.e., matches the distal articulating surfaces of the condyles and cartilage) with the native cartilage in place. Both arcs 376, 378 are tied together via a cross-brace 380, as well as the fact that the arcs converge proximate the anterior femur. Where the arcs 376, 378 converge, the patient-specific placement guide 374 includes a boxed-in frame 382 that faces toward the anterior femur 360 and includes a through opening 384. More specifically, this boxed-in frame 382 is sized to accommodate partial insertion of the base 360 and retain the base in position against the anterior femur 260.

Figure 65:
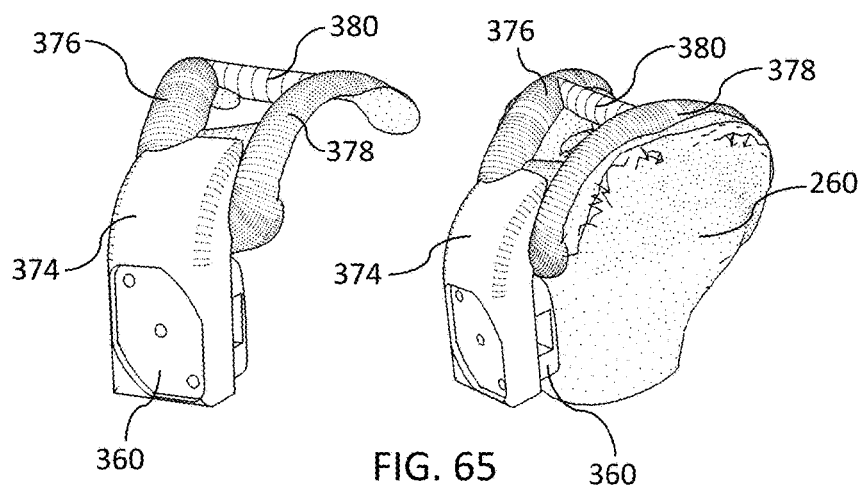
FIG. 65 is an elevated perspective view of the base and position jig of FIG. 64 mounted together, and an elevated perspective view of the base and position jig of FIG. 64 contacting a distal femur.
Figure 66:
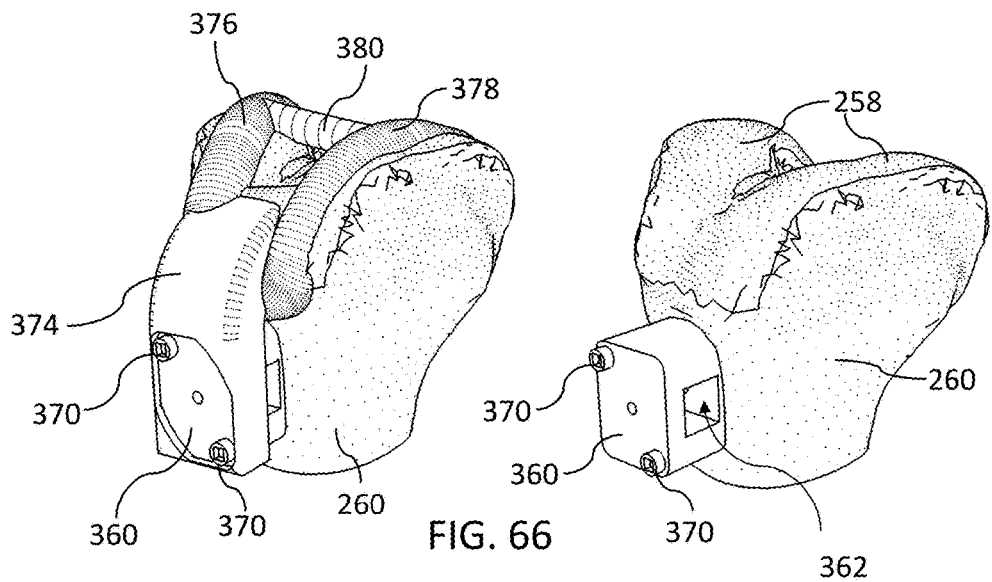
FIG. 66 is an elevated perspective view of the base and position jig of FIG. 64 contacting a distal femur, and two screws operative to mount the base to the distal femur without reliance upon the position jig for attachment.
Figure 67:
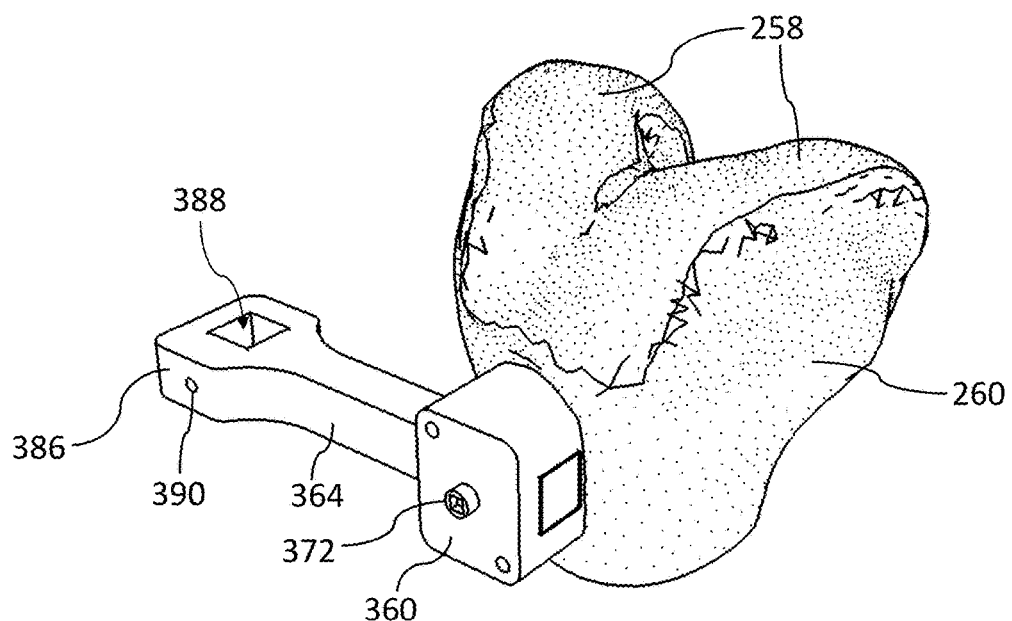
FIG. 67 is an elevated perspective view of the base mounted to the distal femur, where the base is mounted to an arm using a set screw.

Referencing FIGS. 65 and 66, in exemplary form, the patient-specific placement guide 374 is positioned to contact the distal femur 260 so that each arc 376, 378 contacts a respective condyle (and its cartilage). The rotational and lateral position of the patient-specific placement guide 374 is fixed because only one position is operative to align both arcs 376, 378 with their respective condyles so that the internal circumferential surface of each arc is in continuous contact with a respective condyle. Prior to reaching this position, the base 360 is loaded into the boxed-in frame 382 so the three through cavities 366, 368 are accessible via the through opening 384 of the boxed-in frame. In this manner, when the arcs 376, 378 are positioned onto the condyles and aligned, the anterior femur 260 and boxed-in frame 382 are operative to sandwich the base 360 therebetween. At the same time, the patient-specific placement guide 374 orients the base 360 properly with respect to the anterior femur 260 so that a surgeon may drill holes into the anterior femur using the top and bottom circular through cavities 366 at the end of the diagonal line as drill guides. Thereafter, bone screws 370 are inserted into the top and bottom circular through cavities 366 and extended to engage the anterior femur 260, thereby securing the base to the femur. Subsequently, the patient-specific placement guide 374 is removed and the base 360 remains mounted to the anterior femur 260.

As shown in FIGS. 3.4-3.7, after the base 360 is mounted to the anterior femur 260, the horizontal arm 364 is inserted into the through opening 362. In this exemplary embodiment, the horizontal arm 364 comprises a stem having a rectangular cross-section that allows the stem to be inserted into the through opening 362 of the base 360. At one end of the arm 364 is an eyelet 386 that defines a through opening 388 having a constant rectangular cross-section. In this exemplary embodiment, through opening 388 extends perpendicularly with respect to the longitudinal length of the arm 364. The eyelet 386 also includes a second opening 390 that extends through a side of the eyelet. This second opening 390 is concurrently perpendicular to the longitudinal length of the arm 364 and to the axial direction of the rectangular through opening 388. More specifically, the second opening 390 is cylindrical in shape, defined by a constant circular cross-section, that extents through a side of the eyelet 386 and into the rectangular through opening 388. In exemplary form, the second opening 390 is adapted to receive a set screw 392 that concurrently contacts a side rail/track 394 in order to mount the side track to the horizontal arm 364.

The side track 394 comprises a medial AP track, a lateral AP track, and an anterior AP track that has a profile that matches the intended profile of the distal femur 260 post resurfacing. As will be discussed in more detail hereafter, the intended profile is generated automatically by the software package after creation of the patient's femoral bone using images from one or more modalities. In this exemplary embodiment, each side track 394 comprises solid rectangular bar stock having a rectangular cross-section between a first end and a second end. In other words, the side track 394 includes a top surface 396 and a bottom surface that are parallel to one another and separated from one another by a pair of side surfaces 398. In this exemplary embodiment, it is the top surface 396 that embodies the intended profile of the condyle or anterior femur 260 after resurfacing. Each side track 394 also include a pair of cylindrical cavities formed into one or both side surfaces to accept a stop 400, such as a screw, to limit travel of a carriage assembly 402.

Figure 69:
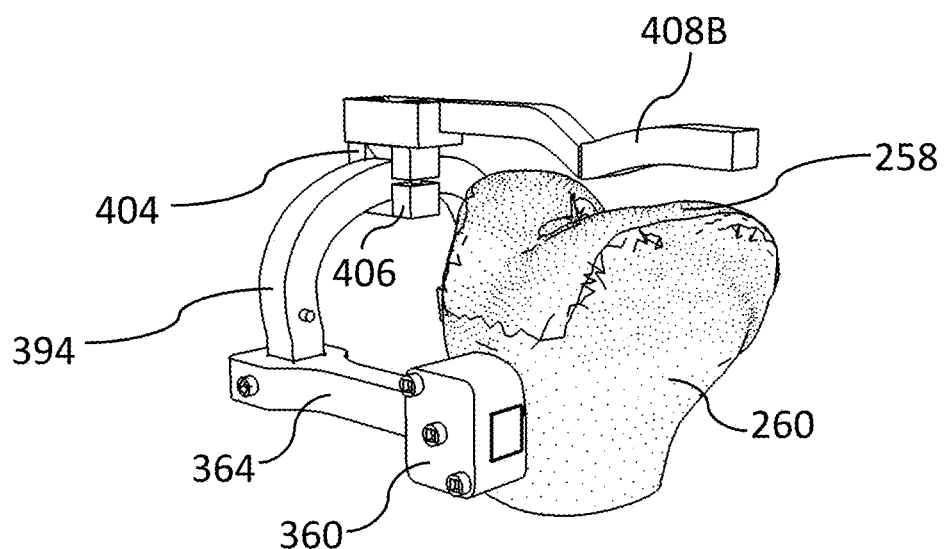
FIG. 69 is an elevated perspective view of the base mounted to the distal femur, where the base is mounted to the arm, which is mounted to the anterior-posterior cutting guide, which is mounted to the lateral cutting guide.
Figure 70:
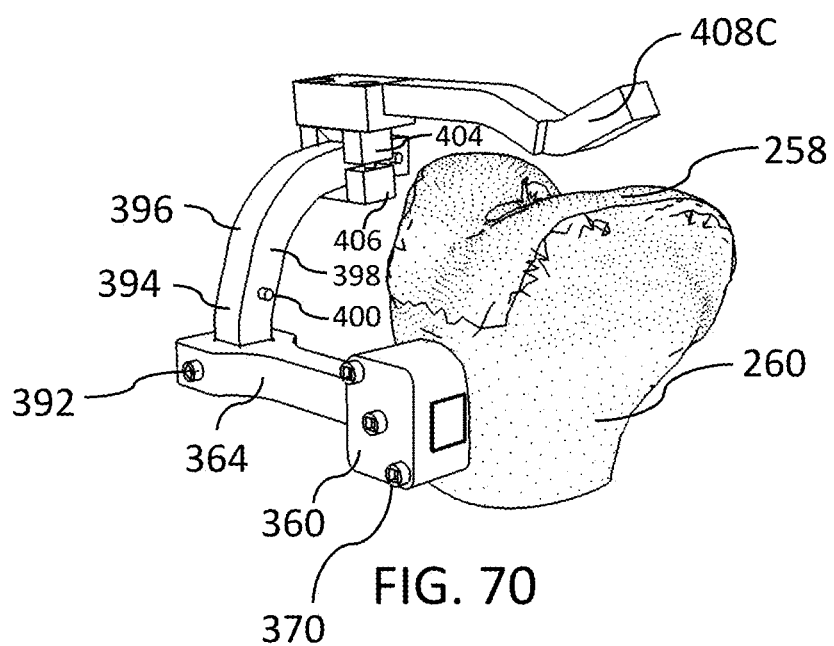
FIG. 70 is an elevated perspective view of the base mounted to the distal femur, where the base is mounted to the arm, which is mounted to the anterior-posterior cutting guide, which is mounted to the anterior cutting guide.
Figure 101:
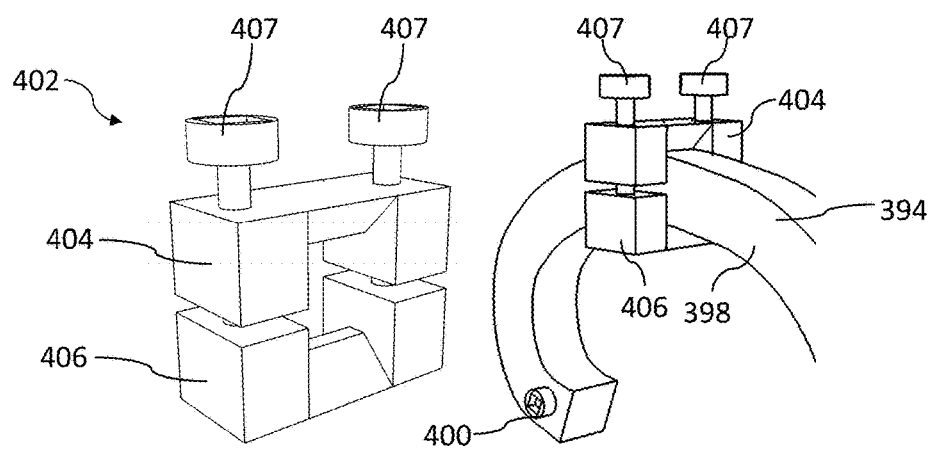
FIG. 101 is an elevated perspective view of a carriage assembly, shown by itself and mounted to a AP cutting guide.
Figure 102:
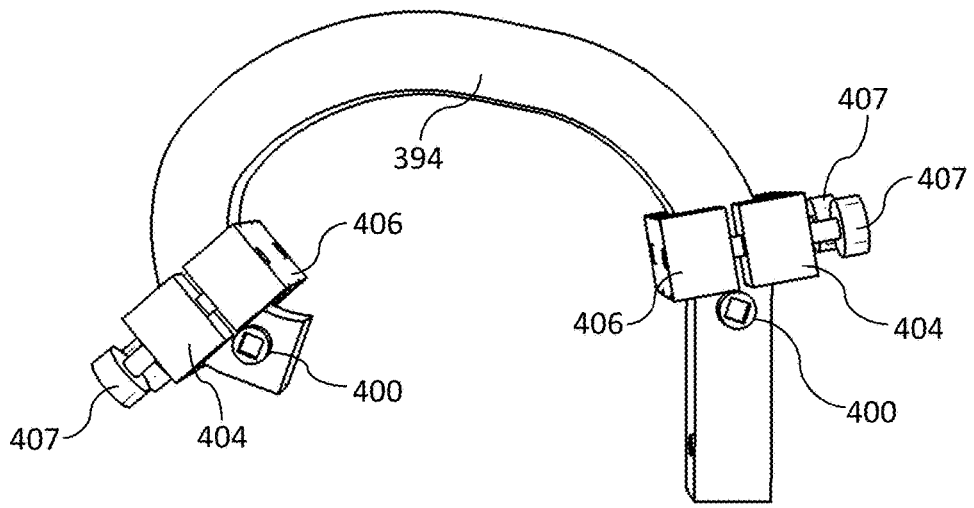
FIG. 102 is a profile view of the carriage assembly of FIG. 101, shown at the ends of the range of motion available for a particular AP cutting guide.
Figure 103:
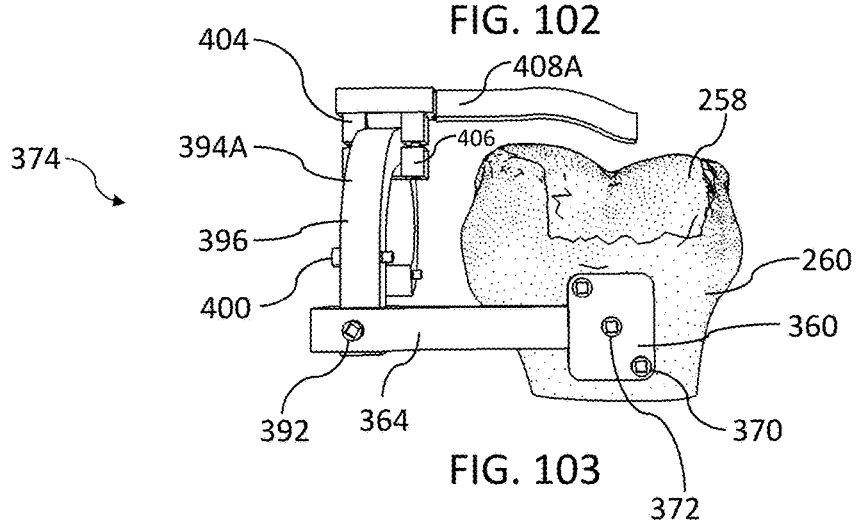
FIG. 103 is an anterior view of a distal femur having mounted to it a base, an arm, an AP cutting guide, and a medial ML cutting guide.
Figure 104:
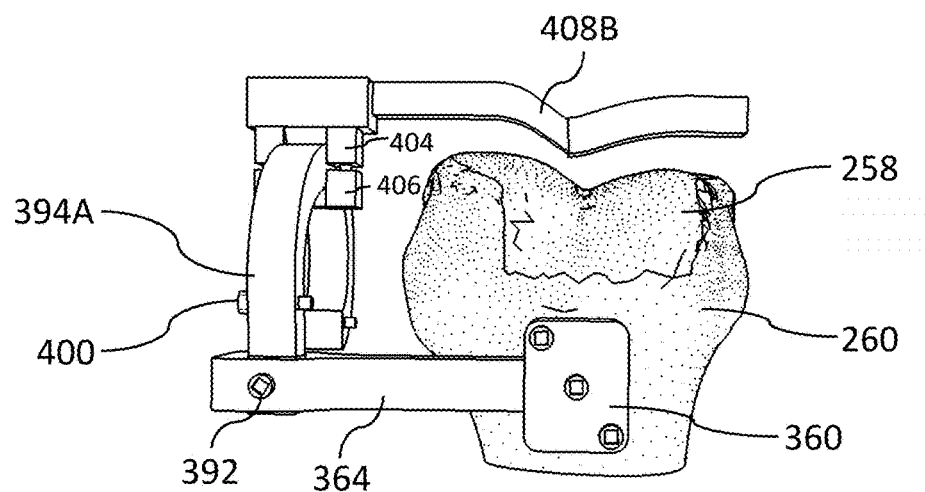
FIG. 104 is an anterior view of a distal femur having mounted to it a base, an arm, an AP cutting guide, and a lateral ML cutting guide.
Figure 105:
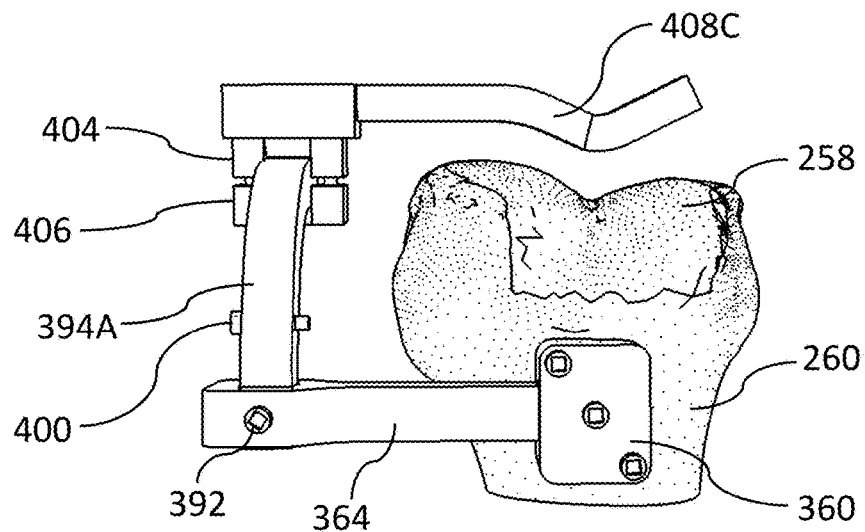
FIG. 105 is an anterior view of a distal femur having mounted to it a base, an arm, an AP cutting guide, and an anterior ML cutting guide.

Referring to FIGS. 69, 70, and 101, the carriage assembly 402 comprises a top follower 404 and a bottom follower 406 that are coupled to one another by a pair of screws 407 that extend vertically and outset from the side surfaces 398 of the side track 394. The bottom follower 406 is generally rectangular in cross-section and includes a flat bottom surface and a contoured top surface. This top surface is notched out to accommodate partial insertion of the side track 394 so that the top surface defining the notch is adjacent the bottom surface of the side track. More specifically, the rectangular notch is slightly larger than the width of the side track 394 to ensure that the bottom follower 406 can move along the side track 394, but the notch is not so wide as to provide significant play that would change the angular pitch of the bottom follower as it is repositioned along the track. Outset from the notch, on both sides, is a pair of cavities sized to receive screws 407 that operate to couple the top follower 404 to the bottom follower 406. The top follower 404 is likewise notched to accommodate partial insertion of the side track 394. More specifically, the top follower 404 includes a rectangular notch on its bottom side that includes a width that is slightly larger than the width of the side track 394 to ensure that the top follower can move along the side track, but the notch is not so wide as to provide significant play that would change the angular pitch of the top follower as it is repositioned along the track. Outset from the notch in the top follower 404, on both sides, is a pair of cavities sized to receive screws 407 that concurrently are received within the cavities of the bottom follower 406 in order to mount the followers to one another. In exemplary form, the screws 407 are tightened so that the vertical distance between the bottom of the notch for the bottom follower 406 and the top of the notch for the top follower 404 is larger than the distance between the top 396 and bottom surfaces of the side track 394. In this manner, there is play in between the followers 404, 406 and side track 394 in the vertical direction, which allows the followers to be repositioned along the length of the side track.

A contour track 408 is mounted to the top follower 404. In exemplary form, contour track 408 includes a mounting platform having a pair of through openings aligned with the through openings of the top follower 404. In this manner, screws 407 inserted through the openings of the mounting platform and the top follower 404 are operative to extend into communication with the bottom follower 406 and mount the followers and the contour track 408 to one another. In this exemplary embodiment, the mounting platform comprises a rectangular housing that is generally constant along the length and width of the housing. The top of the mounting platform includes the pair of through openings extending into communication with the openings of the top follower 404.

Figure 68:
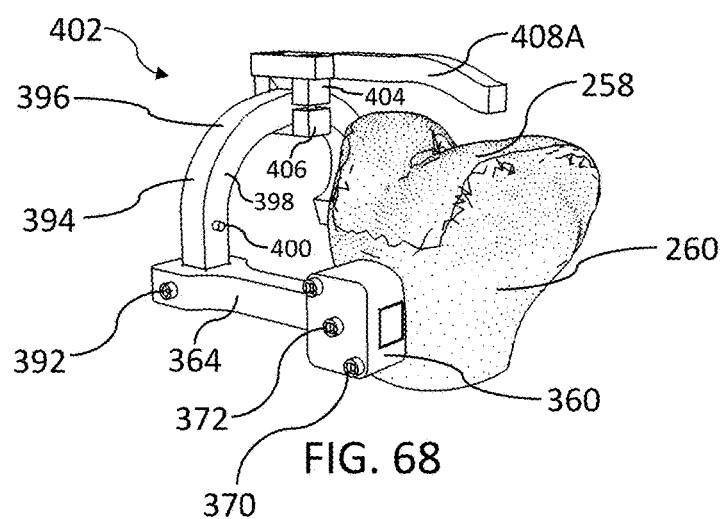
FIG. 68 is an elevated perspective view of the base mounted to the distal femur, where the base is mounted to the arm, which is mounted to the anterior-posterior cutting guide, which is mounted to the medial cutting guide.

In exemplary form, the contour track 408 comprises three segments that are individually, but not concurrently, mounted to the top follower 404 to define the medial to lateral path of the cutter. These three segments comprise a medial ML track 408A, a lateral ML track 408B, and an anterior ML track 408C. As will be discussed in more detail hereafter, each segment of the contour track 408 is utilized by the cutting tool to resurface a portion of the distal femur 260. For example, the medial ML track 408A acts as a medial-to-lateral guide for the cutting tool when cutting the medial condyle (see FIG. 68), until reaching the point where the condyles converge interiorly, where the anterior ML track 408C is utilized as a medial-to-lateral guide for resurfacing the anterior portion of the distal femur (see FIG. 70). Similarly, the lateral ML track 408B is utilized by the cutting tool as a medial-to-lateral guide for resurfacing the lateral condyle (see FIG. 69).

Figure 71:
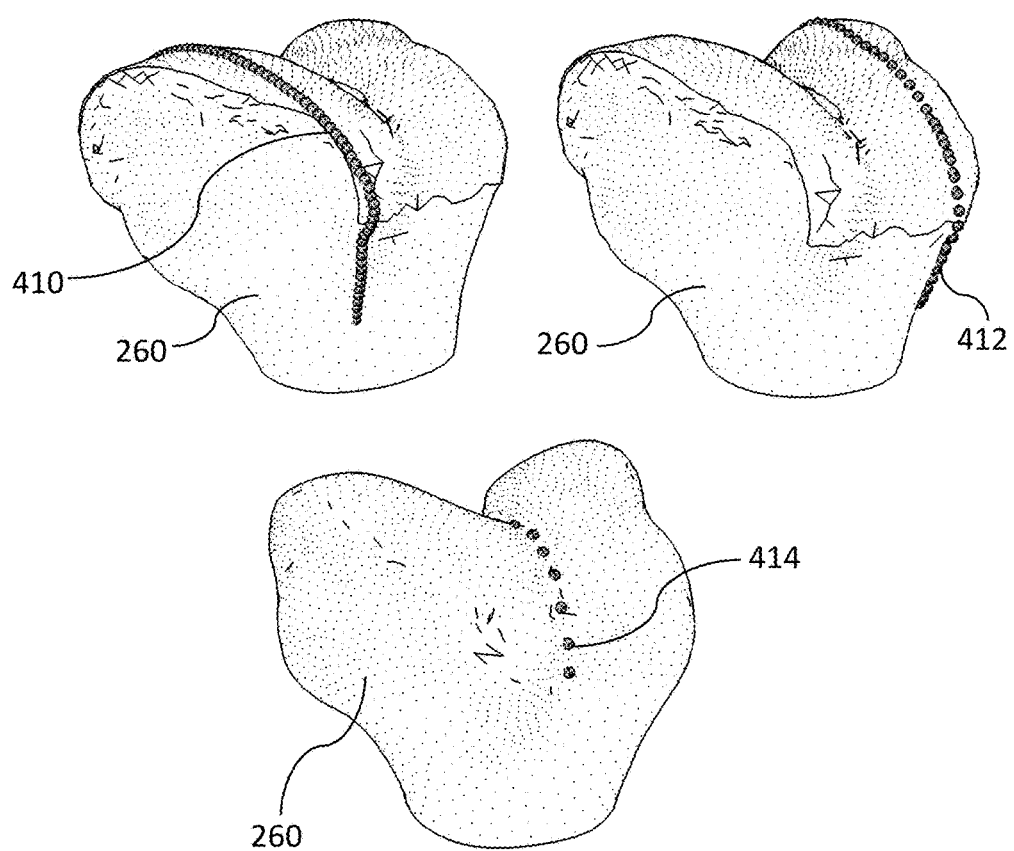
FIG. 71 is an anterior view showing the profile of the medial condyle, the lateral condyle, and the sulcus for the same distal femur.
Figure 72:
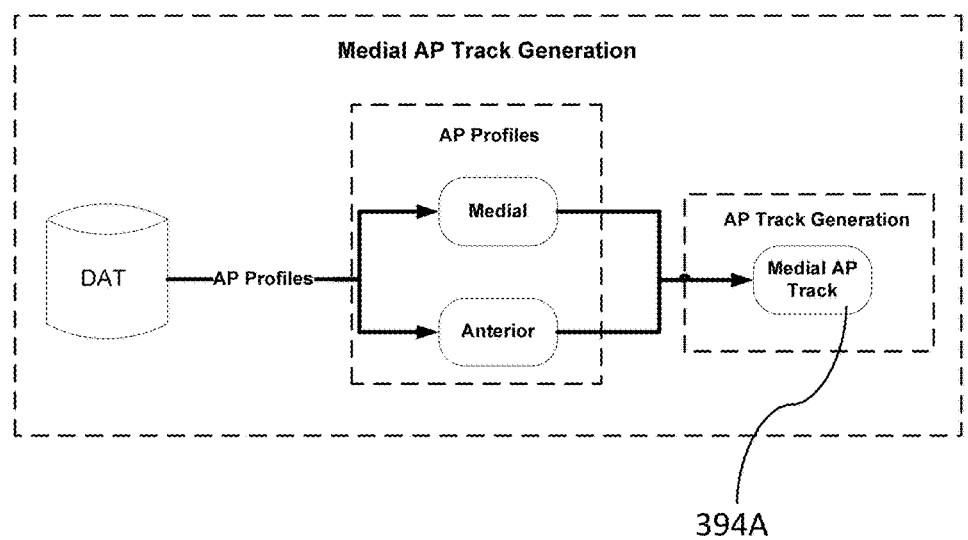
FIG. 72 is a schematic diagram for generation of the medial AP cutting guide.
Figure 73:
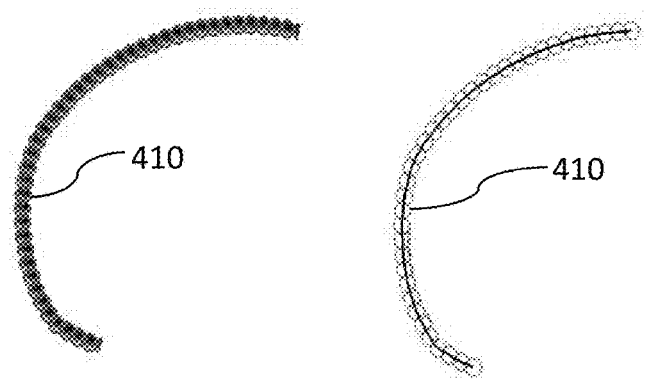
FIG. 73 is a profile view of a set of points representative of the curvature of a medial condyle for a distal femur and the profile contour curve that results from fitting a line to the set of points.
Figure 74:
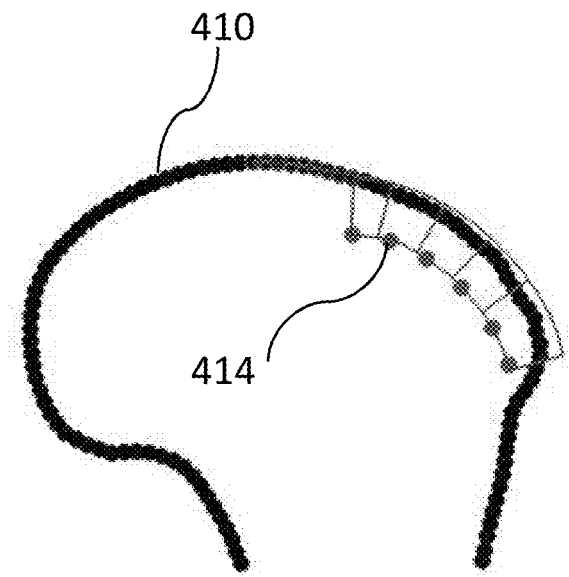
FIG. 74 is a profile of a medial condyle of a distal femur along with anterior sulcus profile lines used to fabricate the medial AP cutting guide.
Figure 75:
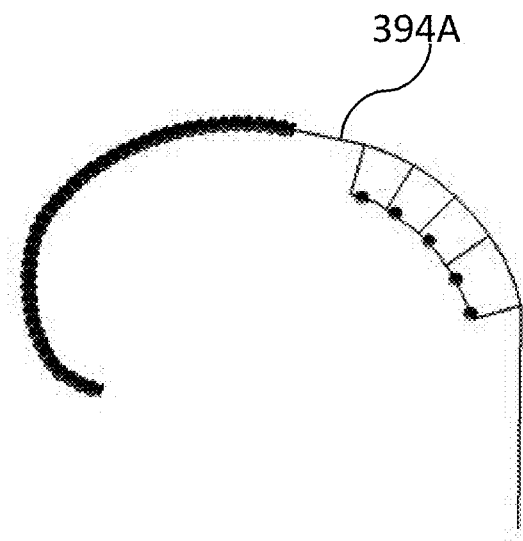
FIG. 75 is a profile of a medial condyle of a distal femur that includes the posterior section defined by the condyle profile and the anterior section defined by the sulcus profile, both of which are used to fabricate the medial AP cutting guide.
Figure 76:
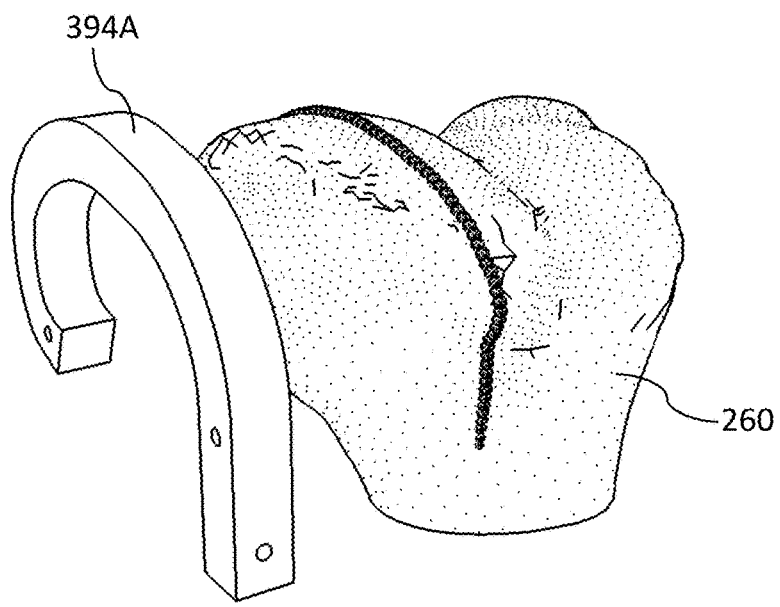
FIG. 76 is an elevated perspective view of the medial AP cutting guide positioned to the side of a distal femur from which the profile for the medial AP cutting guide was generated.
Figure 77:
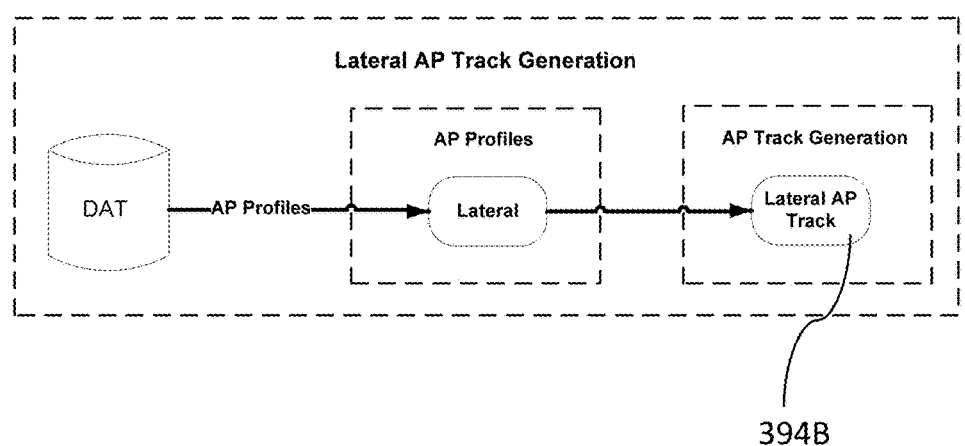
FIG. 77 is a schematic diagram for generation of the lateral AP cutting guide.
Figure 78:
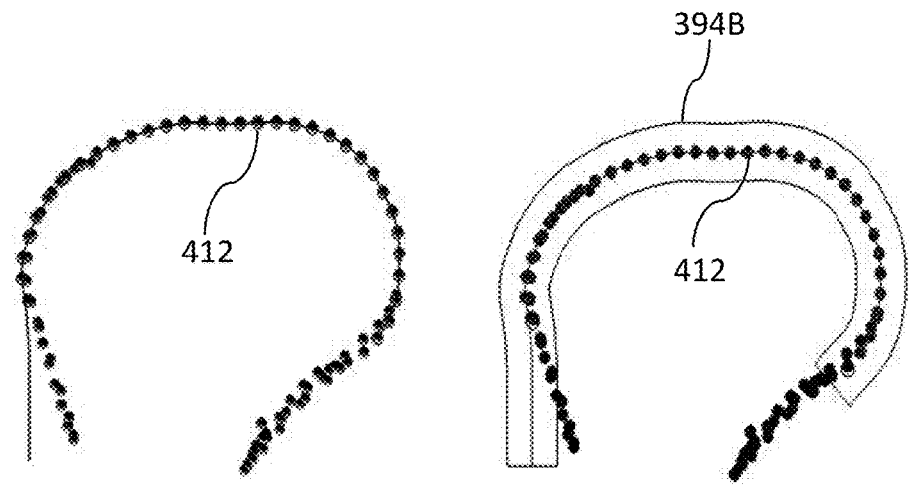
FIG. 78 is a profile view of a set of points representative of the curvature of a lateral condyle for a distal femur and the lateral AP cutting guide that results from matching the curvature of the lateral condyle.
Figure 79:
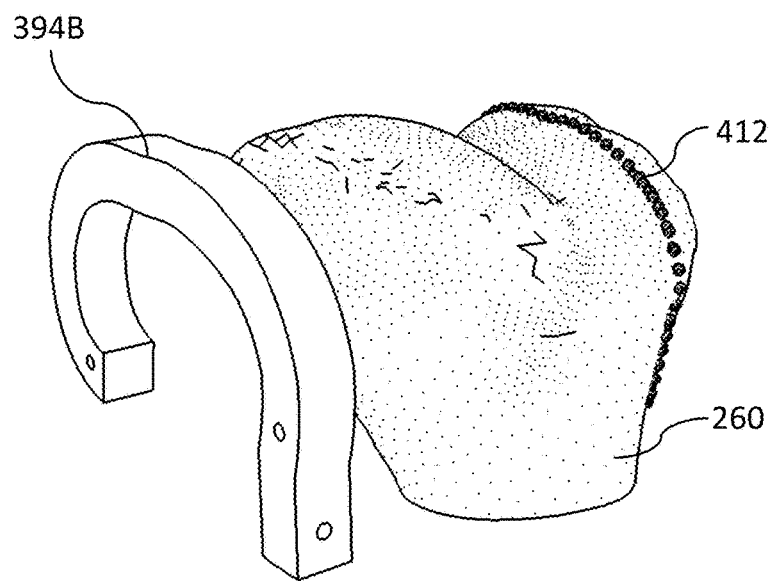
FIG. 79 is an elevated perspective view of the lateral AP cutting guide positioned to the side of a distal femur from which the profile for the lateral AP cutting guide was generated.
Figure 80:
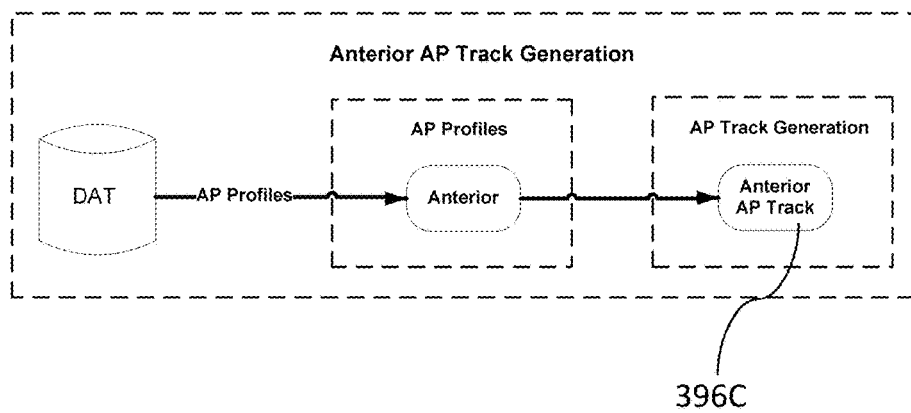
FIG. 80 is a schematic diagram for generation of the anterior AP cutting guide.
Figure 81:
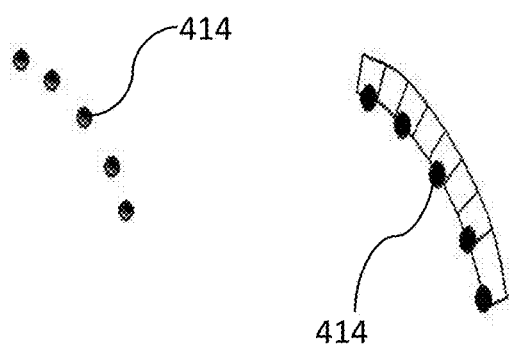
FIG. 81 is a profile view of a set of points representative of the curvature of an anterior portion of a distal femur and the resulting contour of the anterior AP cutting guide.

Referring to FIG. 71, the profile of each side track 394 is generated by the software package using the using the medial 410, lateral 412, and sulcus 414 profiles of the patient's distal femur 260. As discussed previously, the medial and lateral profiles 410, 412 are generated with respect to a plane having within it three points: the most anterior point, the most distal point, and the most posterior point of each condyle with cartilage in place. The outermost points on the bone 260 (exterior surface) that fall within a respective plane are resampled to create a 2D profile consisting of fifty equidistant points, thereby creating a medial profile 410 for the medial condyle and a lateral profile 412 for the lateral condyle. The sulcus profile 414 is calculated by rotating a plane about the TEA in ten degree increments with respect to the distal femur 260 (with cartilage in place). The points where the plane intersects the bone surface are captured, creating a series of contours in the mediolateral (ML) direction that are offset by ten degrees. For each contour, the lowest point of the ML contour defines the sulcus location. The sulcus locations/points are compiled in 2D to create a sulcus profile 414.

Referencing FIGS. 71-76, a process for constructing the medial side track 394A includes taking the 2D profiles 410, 414 of the medial condyle and sulcus so that the medial side track has a posterior profile that matches precisely the 2D profile of the medial condyle and an anterior profile that matches precisely the sulcus profile. In other words, the medial side track 394A is defined posteriorly by the medial profile 410 and anteriorly by the sulcus profile 414. The medial side track 394A provides a guide in an X-Y plane, while the contour track 408 provides a guide in a Y-Z plane with respect to the medial condyle. The curvature of the sulcus is used to create the anterior portion of the medial side track 394A because using only the medial profile of the distal femur results in unsatisfactory resurfacing of the anterior distal femur 260. The software program is operative to combine the curvatures of the posterior medial profile 410 (see FIG. 73) and the sulcus profile 414 (see FIG. 74) to create a single curve (see FIG. 75) that embodies the intended final curvature of the medial side track 394A (see FIG. 76).

Referring to FIGS. 71, 77-79, a process for constructing the lateral side track 394B includes taking the 2D profile for the lateral condyle 412 so that the lateral side track has a profile that matches precisely the 2D profile of the lateral condyle. The lateral side track 394B provides a guide in an X-Y plane, while the contour track 408 provides a guide in a Y-Z plane with respect to the lateral condyle.

Figure 82:
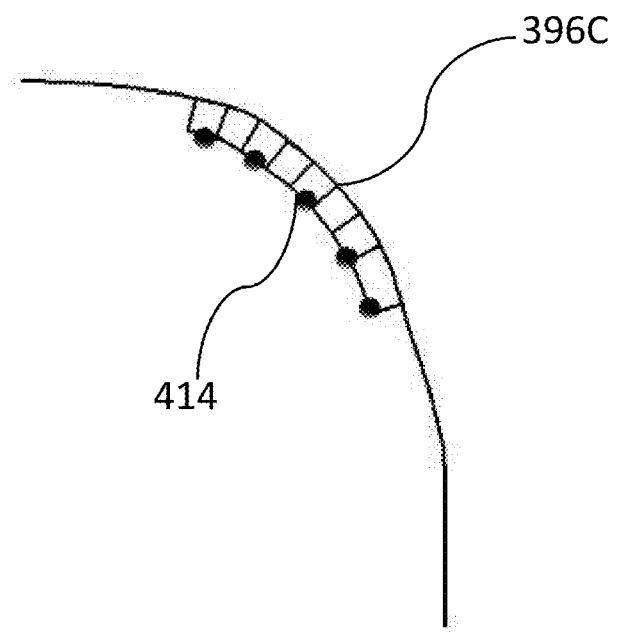
FIG. 82 is a profile view of the curvature defining the anterior AP cutting guide shown with the points representative of the sulcus curvature.
Figure 83:
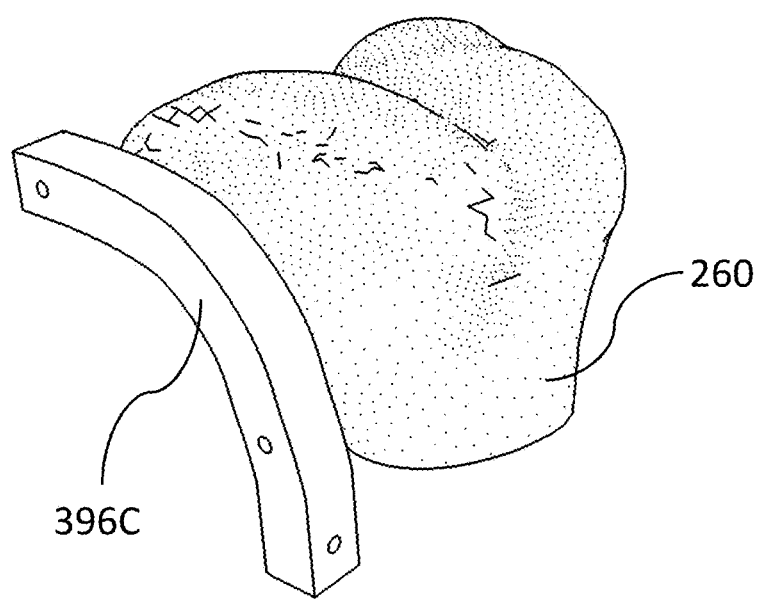
FIG. 83 is an elevated perspective view of the anterior AP cutting guide positioned to the side of a distal femur from which the profile for the anterior AP cutting guide was generated.
Figure 84:
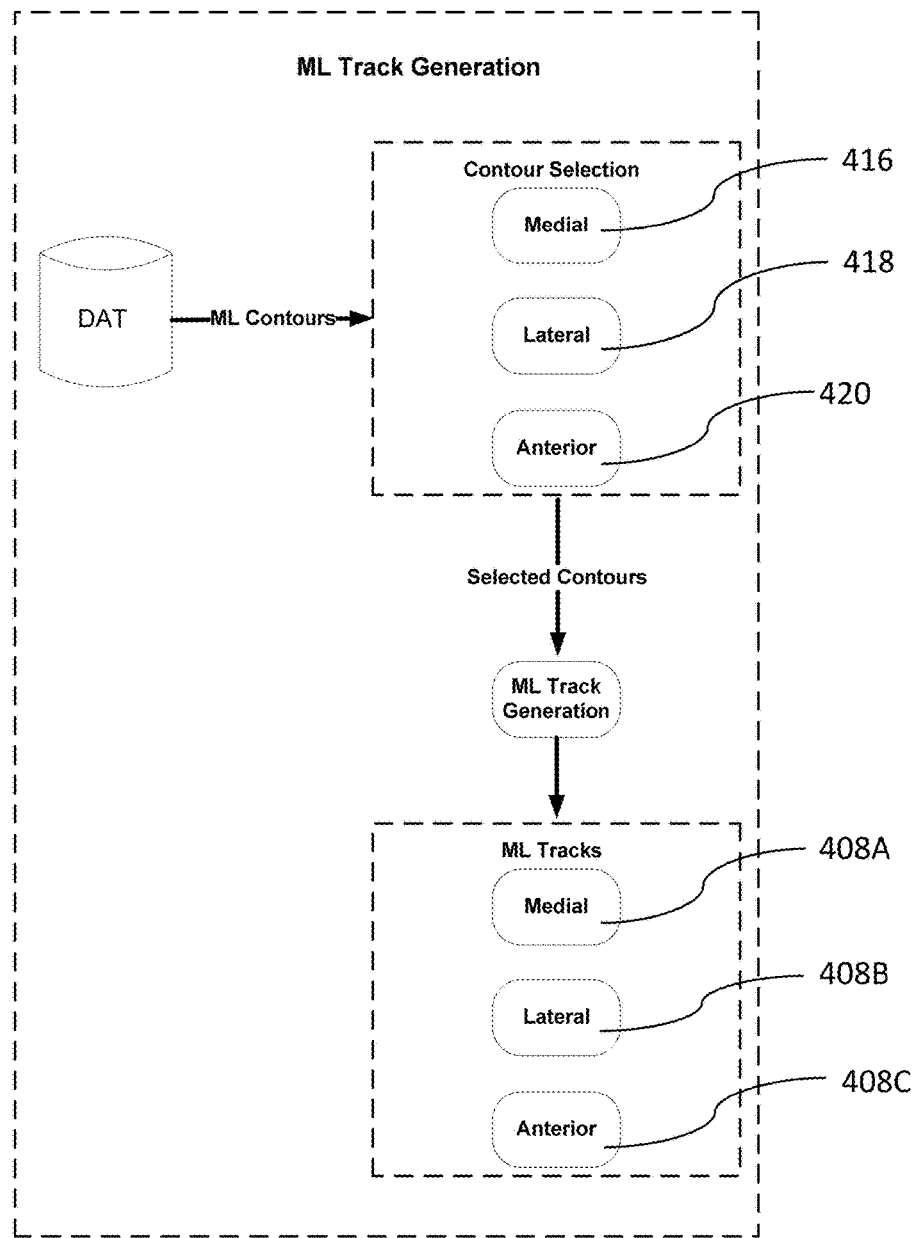
FIG. 84 is a schematic diagram for generation of the ML cutting guides.
Figure 85:
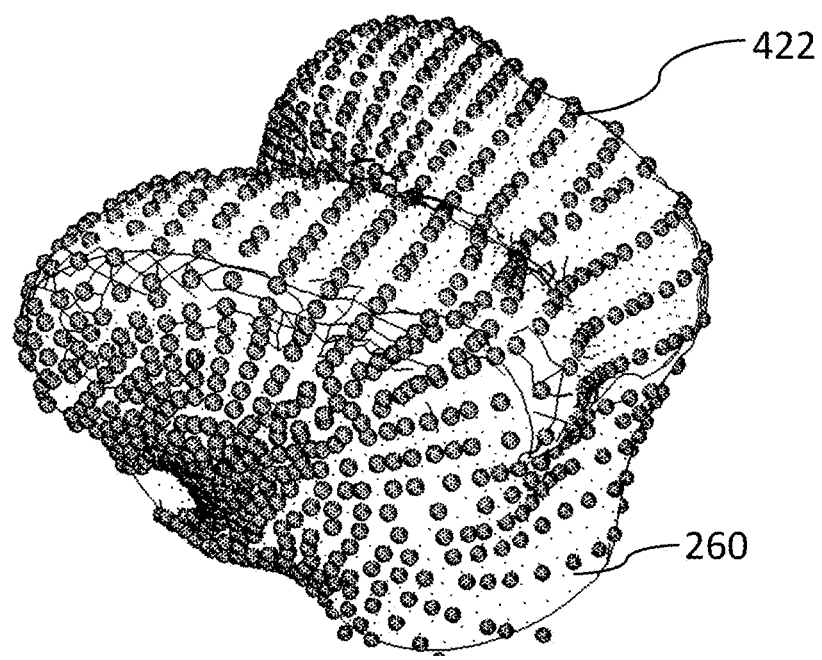
FIG. 85 is an elevated perspective view of a distal femur after a chopper has been rotated about the TEA, where the points represent surface points that collectively provide a contour profile for the exterior of the distal femur.
Figure 86:
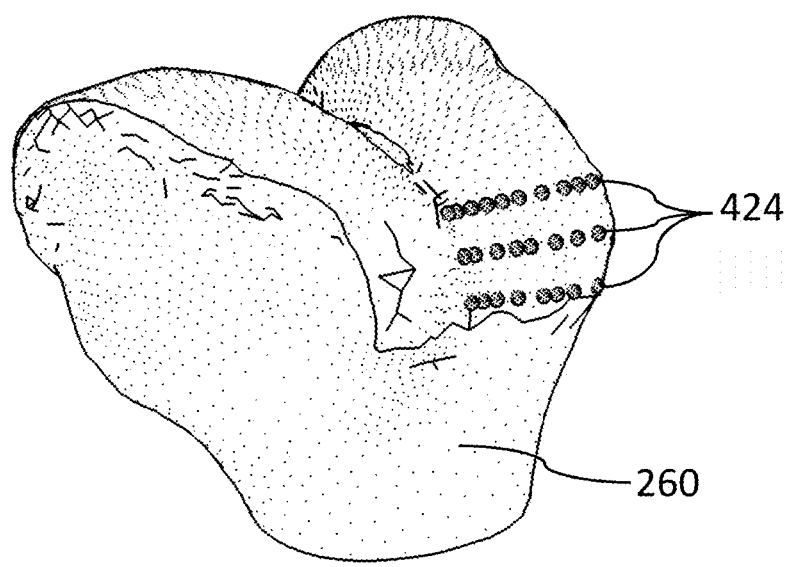
FIG. 86 is an elevated perspective view of a distal femur after a chopper has been rotated about the TEA, where the points represent surface points that collectively provide a contour profile for fabrication of the anterior ML cutting guide.
Figure 87:
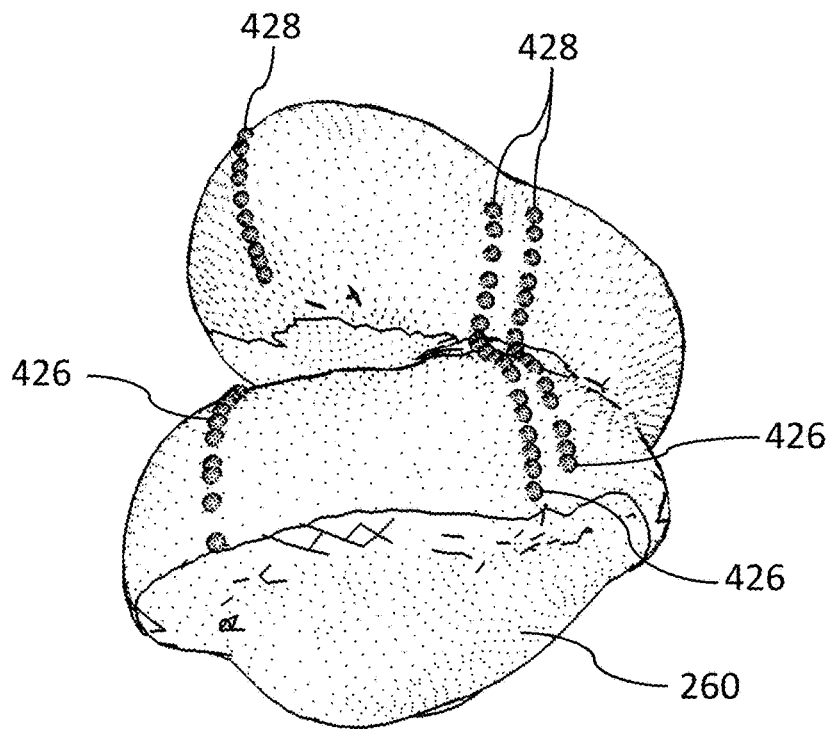
FIG. 87 is an elevated perspective view of a distal femur after a chopper has been rotated about the TEA, where the points represent surface points that collectively provide a contour profile for fabrication of the medial ML cutting guide and the lateral ML cutting guide.
Figure 88:
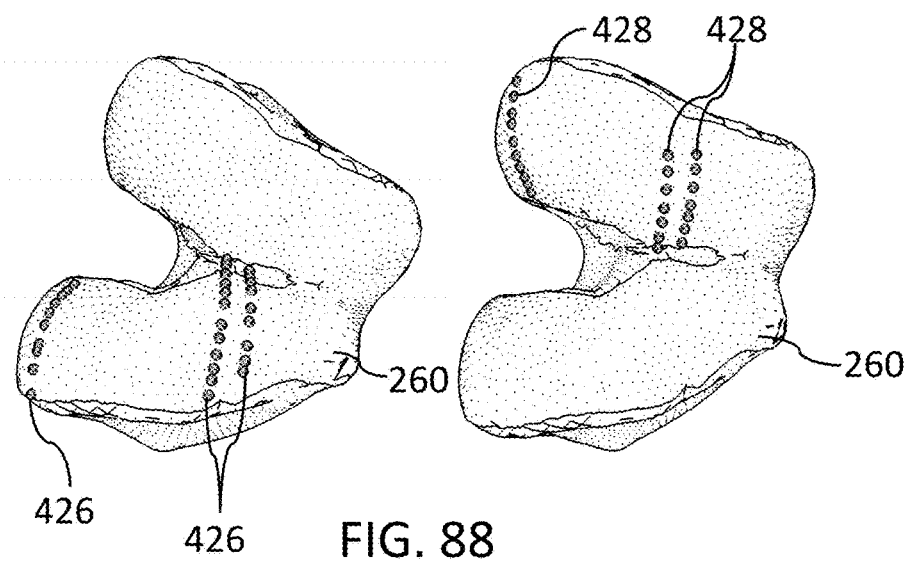
FIG. 88 are elevated perspective views of the same distal femur, shown with data points on the left corresponding to the contour of the lateral ML cutting guide and data points on the right corresponding to the count our of the medial ML cutting guide.
Figure 89:
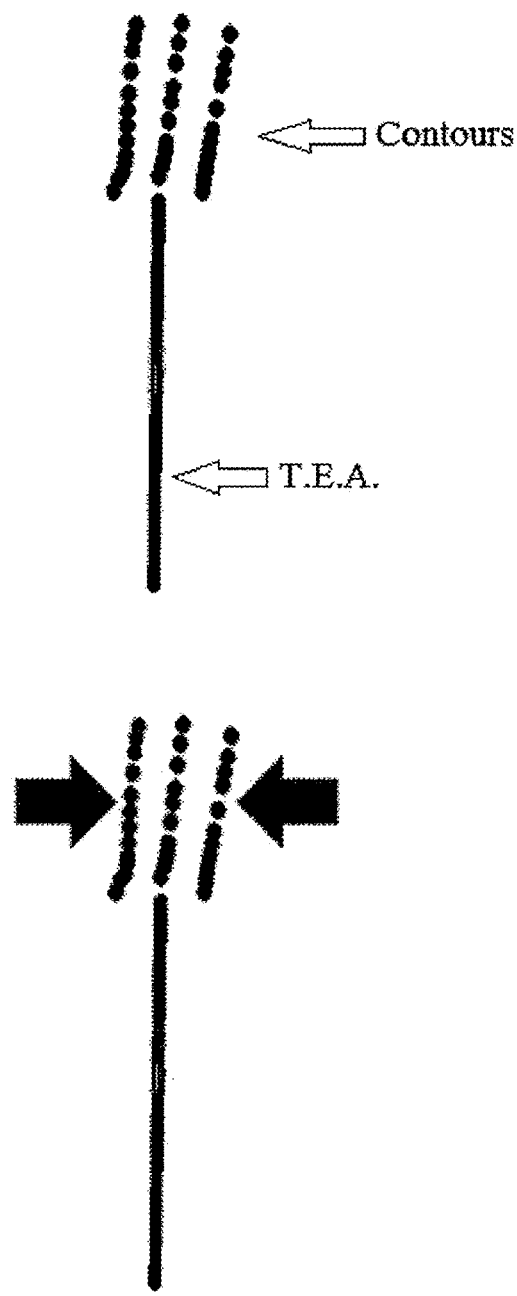
FIG. 89 is a view of the data points of FIG. 88 being rotated about the TEA to create a series of flat planes.
Figure 90:
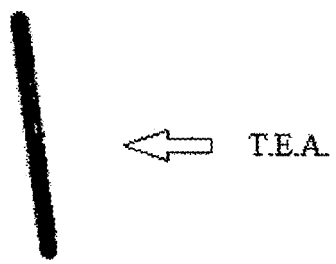
FIG. 90 shows the planes of FIG. 89 after the planes are stacked in the medial-to-lateral direction.
Figure 91:
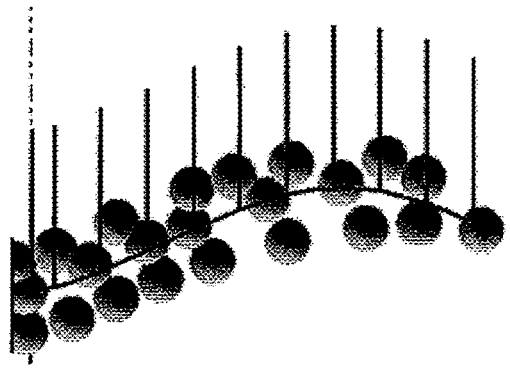
FIG. 91 is a resultant line representing the anterior contour of the stacked planes of FIG. 93, which comprises part of the resultant contour of the ML cutting guides.
Figure 92:
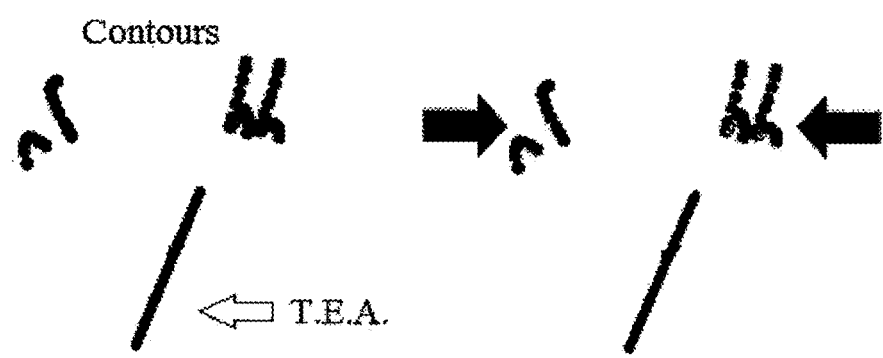
FIG. 92 is a view of the data points of FIG. 91 being rotated about the TEA to create a series of flat planes.
Figure 93:
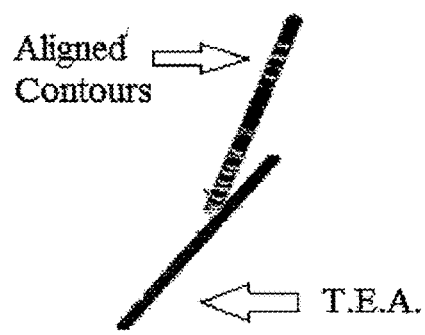
FIG. 93 shows the planes of FIG. 92 after the planes are stacked in the medial-to-lateral direction.
Figure 94:
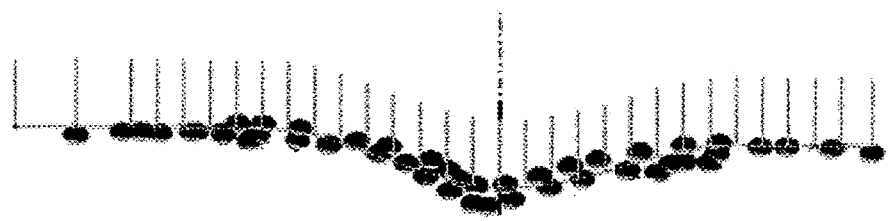
FIG. 94 is a resultant line representing the medial and lateral contours of the stacked planes of FIG. 93, which comprises part of the resultant contour of the ML cutting guides.
Figure 95:
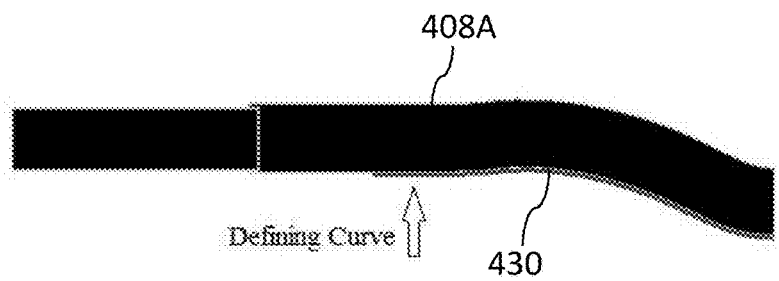
FIG. 95 is a profile view of a medial ML cutting guide shown with the medial contour curve used to fabricate the medial ML cutting guide.
Figure 96:
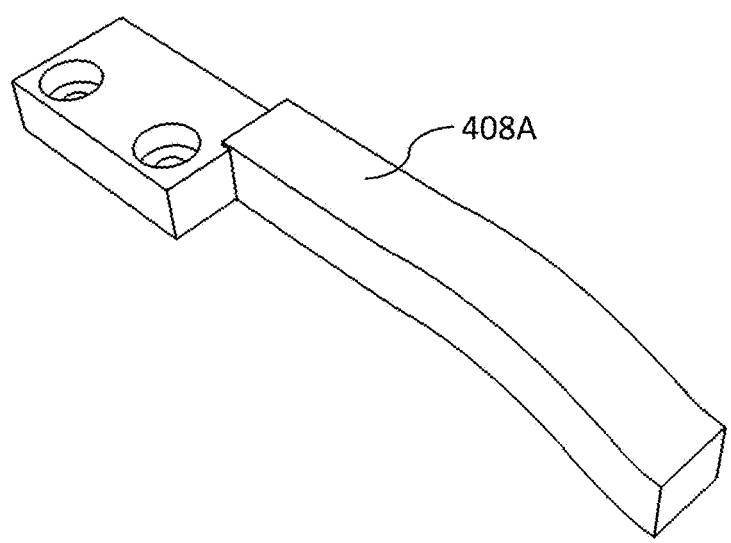
FIG. 96 is an elevated perspective view of a medial ML cutting guide.
Figure 97:
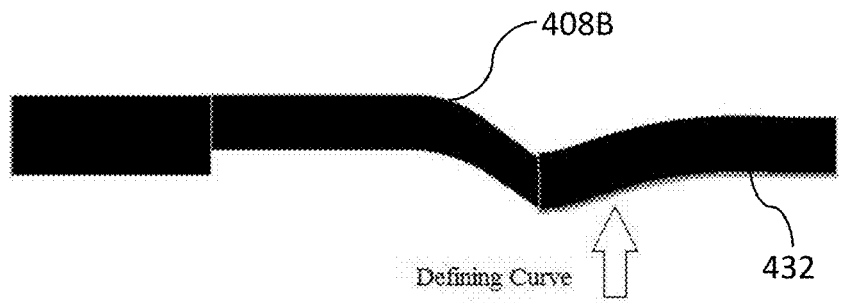
FIG. 97 is a profile view of a lateral ML cutting guide shown with the lateral contour curve used to fabricate the lateral ML cutting guide.
Figure 98:
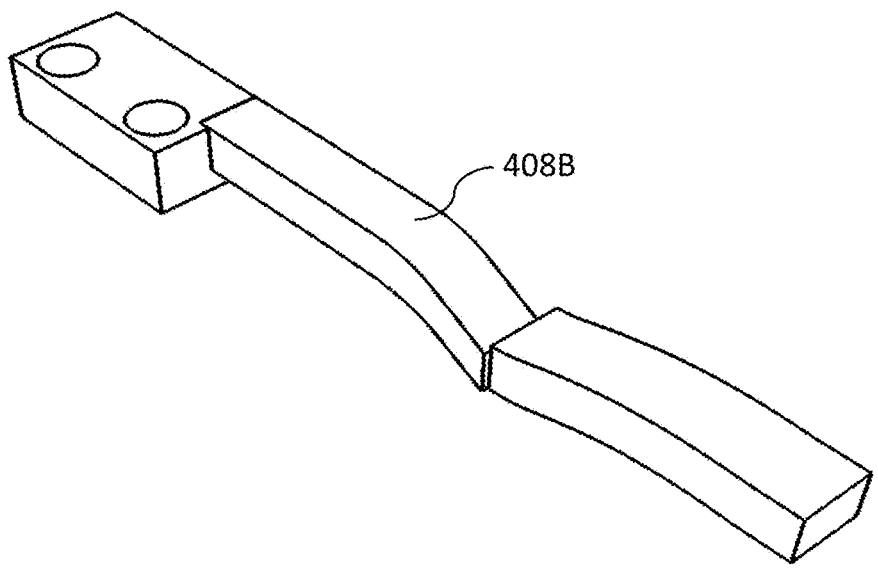
FIG. 98 is an elevated perspective view of a lateral ML cutting guide.
Figure 99:
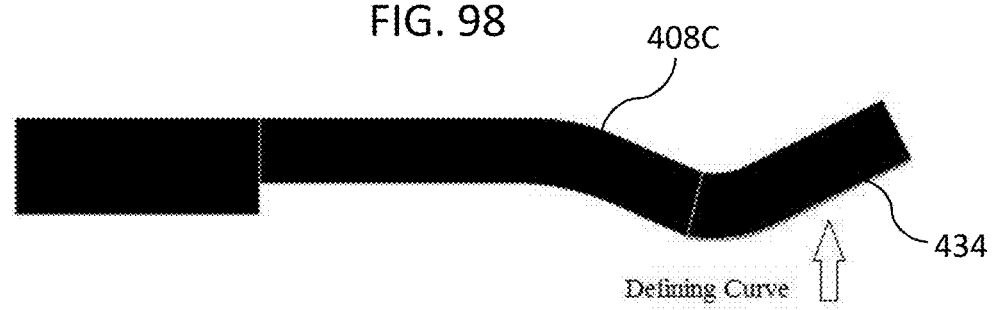
FIG. 99 is a profile view of an anterior ML cutting guide shown with the anterior contour curve used to fabricate the anterior ML cutting guide.
Figure 100:
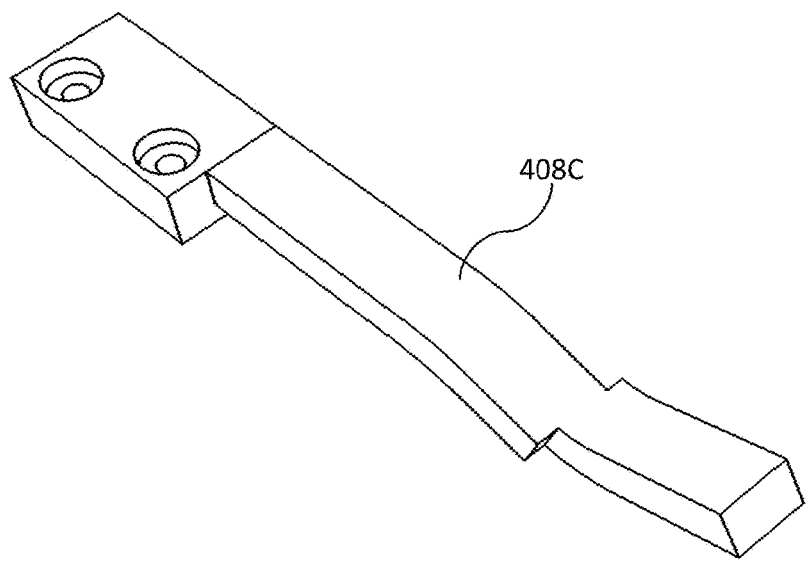
FIG. 100 is an elevated perspective view of an anterior ML cutting guide.

Referring to FIGS. 71 and 80-83, a process for constructing the anterior side track 394C includes taking the 2D profile for the sulcus and using the software package to extrapolate the profile 414 outward (see FIG. 81) to increase the size of the curve so that the anterior AP side track created from the sulcus curvature is similar in size to the medial and lateral AP side tracks (see FIG. 82). The anterior AP side track 394C provides a guide in an X-Y plane allowing the cutting instrument to remove the cartilage remaining after application of the lateral AP side track 394B and the medial AP side track 394A.

Referencing FIGS. 84-88, the medial ML track 408A guides the cutting instrument in the Y-Z plane (i.e., in the medial-to-lateral direction) across the surface of the distal femur 260. As mentioned previously, the patient's femur 260 is modeled to create a virtual, 3D bone that the software package uses to extract the contour of the patient's distal femur and construct a virtual jig (in this case the medial ML track) that is output to a CNC machine for fabrication of the actual medial ML track 408A. The software package initially takes the patient's virtual, 3D bone and generates the medial 416, lateral 418, and sulcus 420 contours by rotating a plane about the TEA in ten degree increments to create a point cluster 422 of the external surface of the distal femur (see FIG. 85). The surface points 422 corresponding to cartilage are sampled and the regions of interest are split between the anterior femur (FIG. 86) and posterior femur (FIGS. 87 and 88) due to variability between the two regions. In this exemplary discussion, the anterior area of interest is limited to the three contours 424 and the posterior area is also limited to three medial-to-lateral contours 426, 428.

Referring to FIGS. 89-94, the acceptable points 422 of the contours 424-428 are collapsed towards a single plane (see FIGS. 89, 90, 92, and 93). It is achieved by rotating them towards an arbitrary common plane about the TEA. This process produces a parametric curve by calculating the best fit of the anterior and posterior contour sets (see FIGS. 91 and 94).

Referring to FIGS. 95-100, the curve fit 430 to the medial contour points 424 is used to define the medial ML track 408A, the curve 432 fit to the lateral contour points 426 is used to define the lateral ML track 408B, and the curve 434 fit to the anterior contour points 428 is used to define the anterior ML track 408C.

Figure 106:
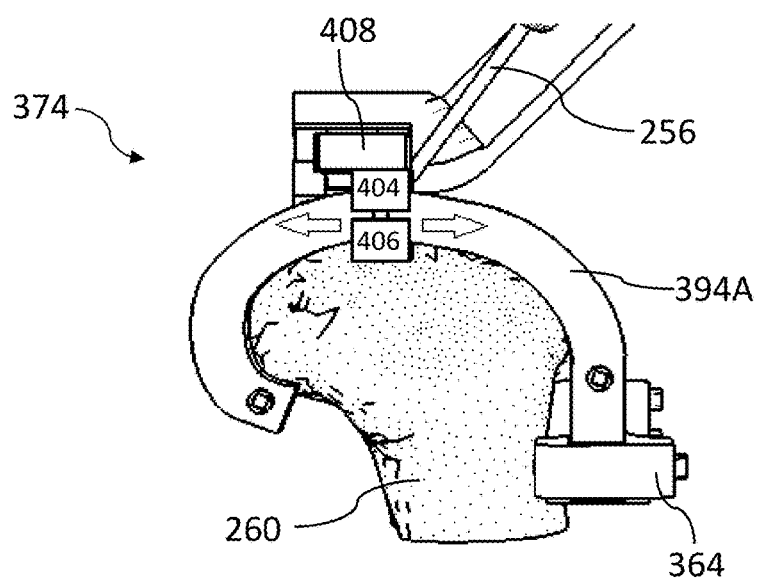
FIG. 106 is a profile view of a distal femur having mounted to it a base, an arm, an AP cutting guide, a ML guide, and a microsurgical robot, and a repositioning device for removing cartilage from the distal femur, where the ML guide, the microsurgical robot, and the repositioning device are repositionable along the AP cutting guide.
Figure 107:
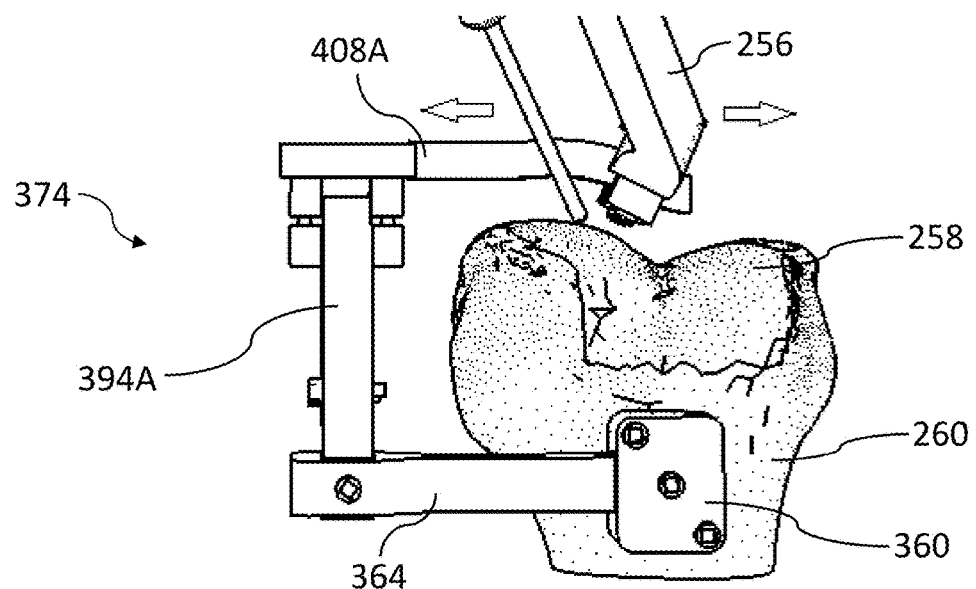
FIG. 107 is an anterior view of the structure of FIG. 106, where the microsurgical robot and the repositioning device are repositionable along the ML guide.

Referencing FIGS. 55, 106, and 107, the patient-specific placement guide 374 is shown mounted to the patient's distal femur 260 with the medial AP side track 394A mounted to the base 360 via the arm 364. In succession, the medial ML track 408A, lateral ML track 408B, and anterior ML track 408C are mounted to the medial AP side track 394A to guide the cutting instrument to resurface the medial and lateral condyles, as well as the anterior portion of the distal femur 260.

Referring to FIGS. 101-105, in operation, the cutting tool 256 is coupled to the patient-specific placement guide 374 in order to facilitate relatively small incremental movements in the anterior-posterior direction and larger movements in the medial-lateral direction. More specifically, as discussed above, one of the medial, lateral, or anterior ML track 408 is repositionably mounted to a side AP track 394 to facilitate guided movement in the anterior-posterior direction. The cutting tool 256 is repositionably mounted to the respective ML track 408 that is mounted to the side AP track 394. In this manner, the cutting tool 256 can be repositioned in the medial-lateral direction to remove cartilage 258 (and possibly some bone) to create a cutting profile having a constant depth that matches the associated medial, lateral, or anterior ML track 408 mounted to the cutting tool. After the cutting tool 256 has completed a medial-lateral swath, the cutting tool is repositioned in the anterior-posterior direction to cut another swath that slightly overlaps the previous swath to ensure complete coverage between sequential swaths. This process is repeated until the entire area of the distal femur is cut that is intended to be cut with the respective ML track 408. Thereafter, a different ML track 408 is installed and the process repeated for this ML track. Thereafter, the process is repeated for the final ML track 408.

The goal of the cutting process is to remove cartilage 258 from the distal femur 260. Of concern is the possibility of excessive gouging into the bone during cartilage removal. Slight grazing of the bone 260 is almost unavoidable because the cutting depth is maintained as a constant depth. Nevertheless, gouging may be eliminated by reducing the cutting depth. But reductions in cutting depth also reduce the overall thickness of the cartilage 258 removed and may result in too much cartilage being retained. The ideal circumstance is to have minimal bone grazing and maximum cartilage removal. In order to provide the proper cutting depth for each ML track 408, a simulation is preformed by the software package to quantitatively test the amount of gouging into the bone 260 by comparing a simulated cutting pathway at a particular depth to the patient's bone model without cartilage.

The simulation is performed by sweeping each ML track 408 along its AP pathway, as defined by the relevant AP side track 394. The simulation assumed all portions of the patient-specific placement guide were rigid with rigid connections between the ML tracks 408 and AP side track 394 and the holster coupling the cutting device to a respective ML track. The angles between the AP side track 394 and ML tracks 408 were assumed to be perpendicular at all times in the coronal plane. It should be noted that vibration of the cutting device was not accounted for in the simulation.

For each ML track simulation, the ML track 408 was translated along the AP side track 394 until the ML track made contact with the bone surface. After reaching the depth where the ML track 408 contacted bone, the respective ML track was then swept along its respective AP side track 394 to generate both a sheet body and a solid cutting body. The sheet body comprises a very thin sheet (vertically thin) that conforms to the undersurface of the cartilage 258 and bone 260 post cutting. This sheet body is used to assess the amount of gouging into the bone that occurs as any bone contacting the sheet indicates a gouge. The solid body comprises a three dimensional object made up of the amount of material to be removed by the cutting tool as the cutting tool is moved in the medial-lateral direction for a respective ML track 408. The solid body was generated by Boolean subtraction method using the femur model with cartilage and the femur model post cutting. After all cuts from the ML tracks 408 were simulated, the resultant femur and separated cartilage representing the result of a TKA preparation was imported into Amira 3.0 and the cuts were assessed through a distance map between the cartilage surface and processed femur surface.

Figure 108:
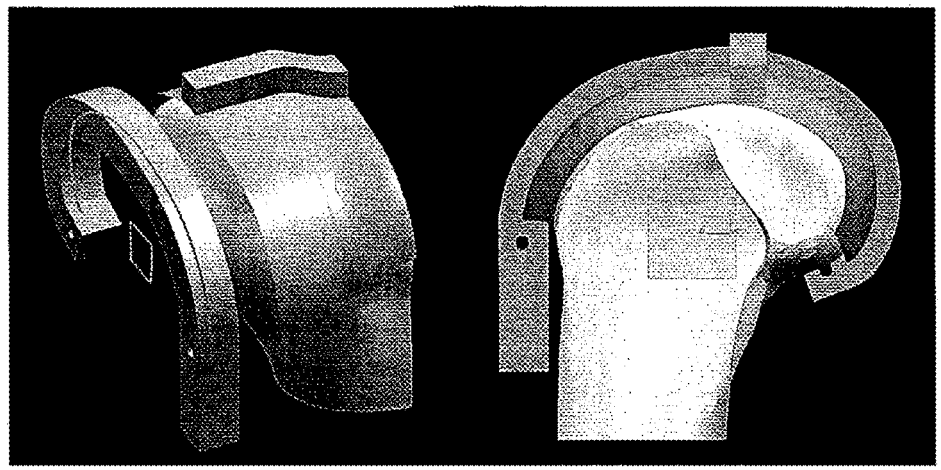
FIG. 108 is an anterior and profile view of the anterior ML track before lowering the cutting depth by 1 mm.

Referring to FIG. 108, it was observed during the simulation that while no bone is being gouged using the medial ML track at a first predetermined depth, there is a noticeable gap to the anterior surface. To address this anterior gap and possibly increase the amount of cartilage removed, the simulation was again carried out, but this time with the medial ML track being lowered by one millimeter.

Figure 109:
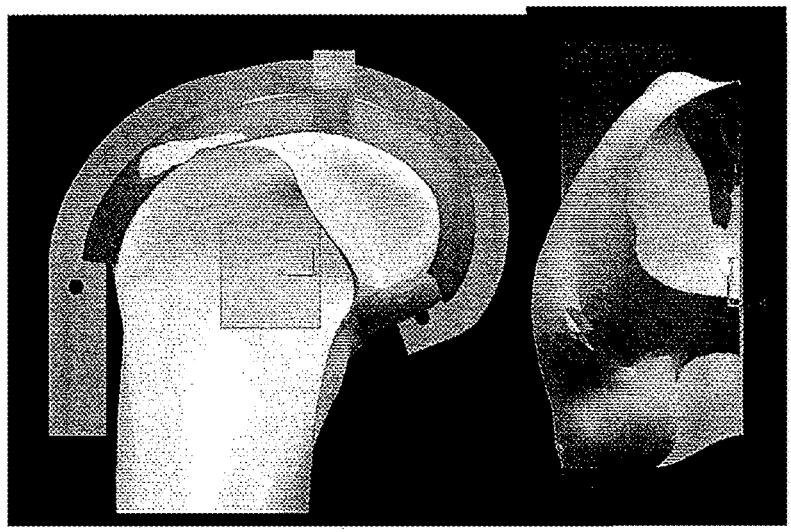
FIG. 109 is an anterior and profile view of the anterior ML track after lowering the cutting depth by 1 mm.
Figure 110:
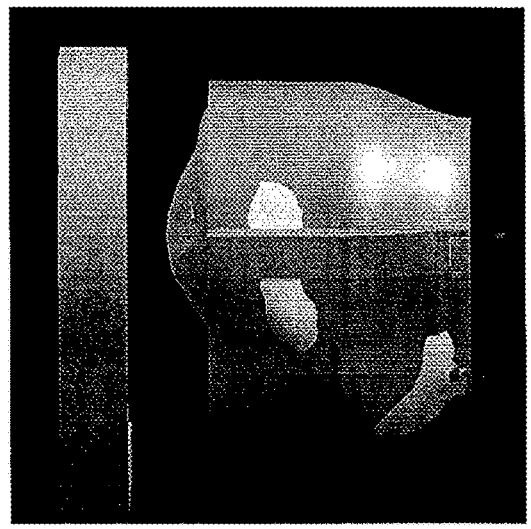
FIG. 110 is a distal view of the anterior ML track after lowering the cutting depth by 1 mm.

Referencing FIGS. 109 and 110, the anterior and distal views of the distal femur with the sheet body in place show that the anterior gap is lessened, but that some grazing of the bone occurred. Based upon the comparison between the medial ML track simulations, a surgeon may raise or lower the medial ML track with respect to the side AP track.

Figure 111:
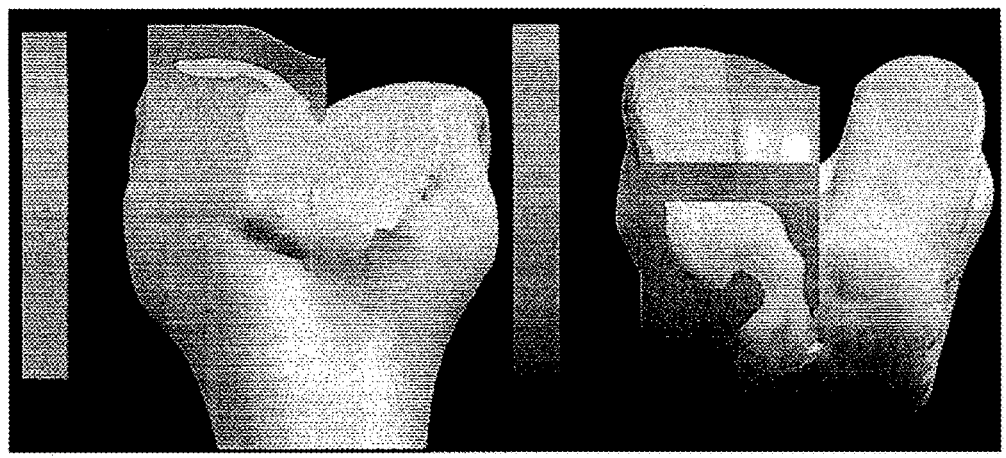
FIG. 111 is an initial anterior view and distal view of medial ML and AP tracks.
Figure 112:
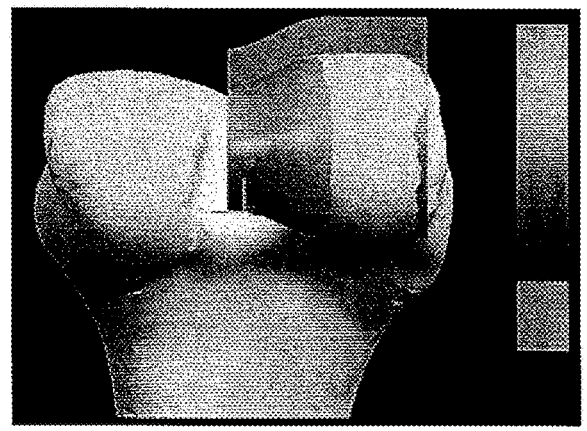
FIG. 112 is an initial posterior view of medial ML and AP tracks.
Figure 113:
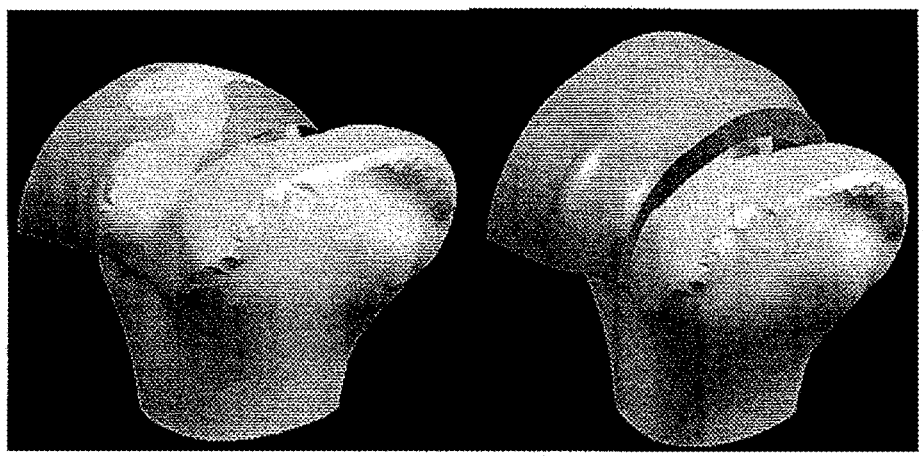
FIG. 113 is an elevated perspective view showing the sheet body and cartilage cutting body (medial).

Referring to FIGS. 111-113, the side AP track is shown positioned with respect to the medial ML track. The computer program evaluates the swath created by the cutting tool and creates the sheet body superimposed onto the distal femur with cartilage in place. In this circumstance, the sheet body provides an observer with and indication of the amount of cartilage removed as all cartilage above the sheet body would be removed. At the same time, the software program is capable of generating the solid body superimposed onto the distal femur with cartilage to show the three dimensional cutting route of the cutting tool.

Figure 114:
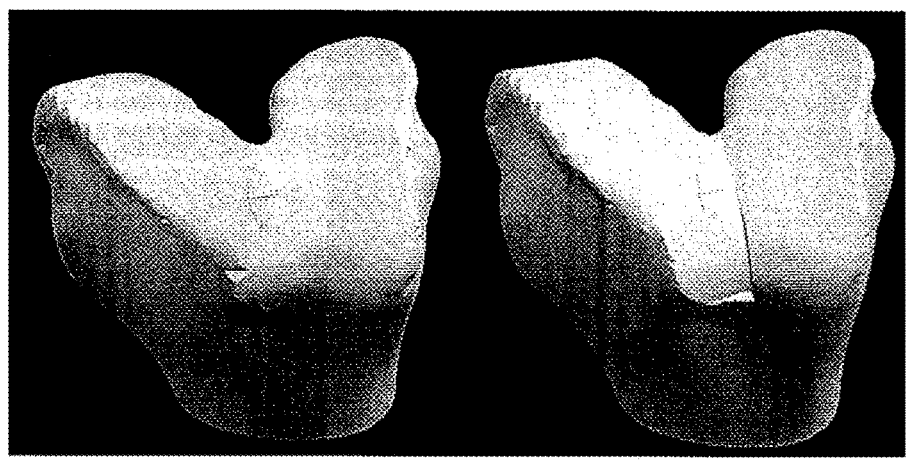
FIG. 114 is an anterior view of a distal femur before and after medial cartilage removal.
Figure 115:
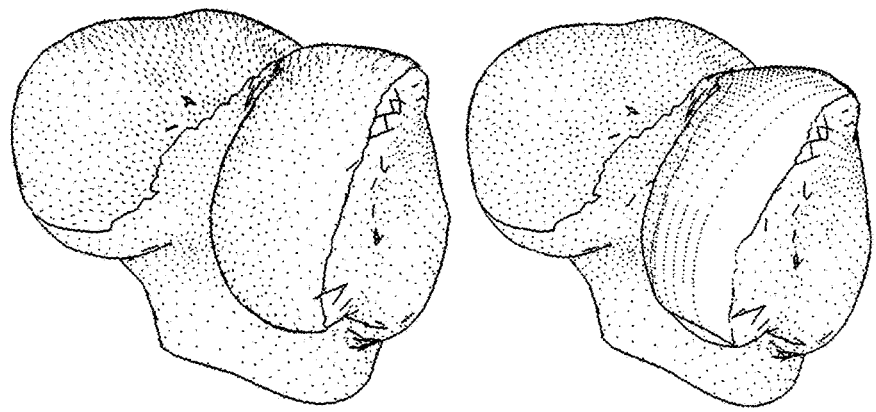
FIG. 115 is a posterior view of a distal femur before and after medial cartilage removal.

Referencing FIGS. 114 and 115, anterior and posterior views of the femur as part of the simulation carried out by the software package represent the femur with cartilage and without cartilage post cutting. As can be seen in these figures, the resulting bone is generally smooth and lacks cartilage on the bearing surfaces of the medial condyle. It was observed during the simulation that while no bone is being gouged using the lateral ML track at a first predetermined depth, there is a noticeable gap to the anterior surface. To address this anterior gap and possibly increase the amount of cartilage removed, the simulation was again carried out, but this time with the lateral ML track being lowered by two millimeters.

Figure 116:
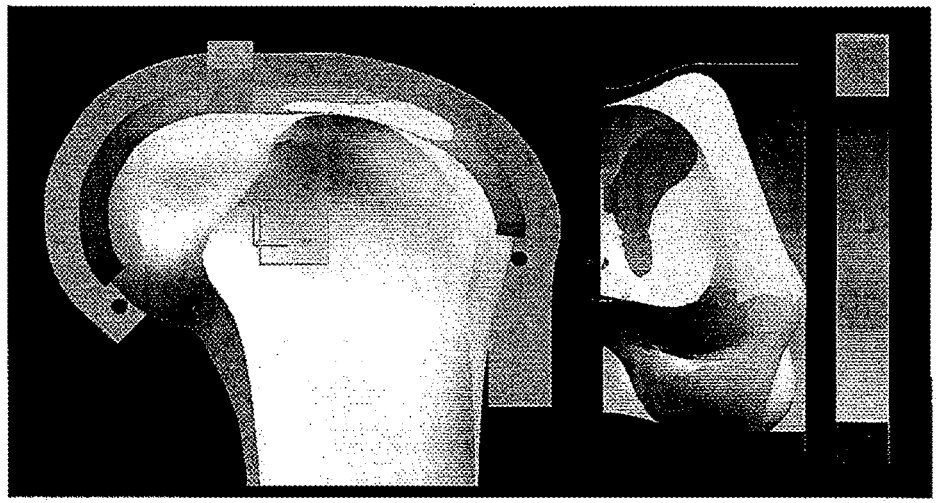
FIG. 116 is an elevated perspective view and s profile view of the lateral ML track before lowering the cutting depth by 2 mm.
Figure 117:
FIG. 117 is a distal view of the lateral ML track after lowering the cutting depth by 2 mm.

Referencing FIGS. 116 and 117, the anterior and distal views of the distal femur with the sheet body in place show that the anterior gap is lessened, but that some grazing of the bone occurred. Based upon the comparison between the lateral ML track simulations, a surgeon may raise or lower the lateral ML track with respect to the side AP track.

Figure 118:
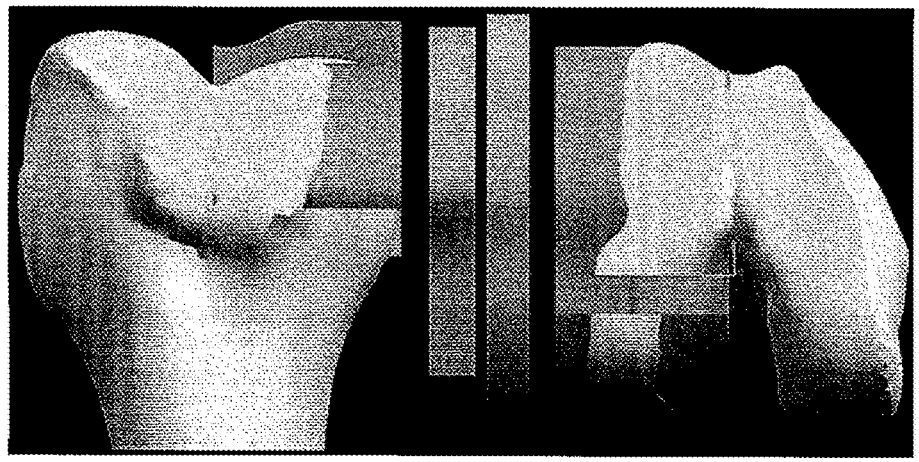
FIG. 118 is a lateral view and a distal view of the lateral ML track after lowering the cutting depth by 2 mm.
Figure 119:
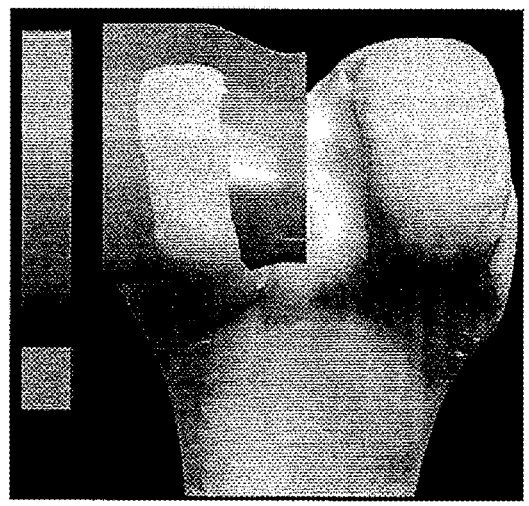
Figure 120:
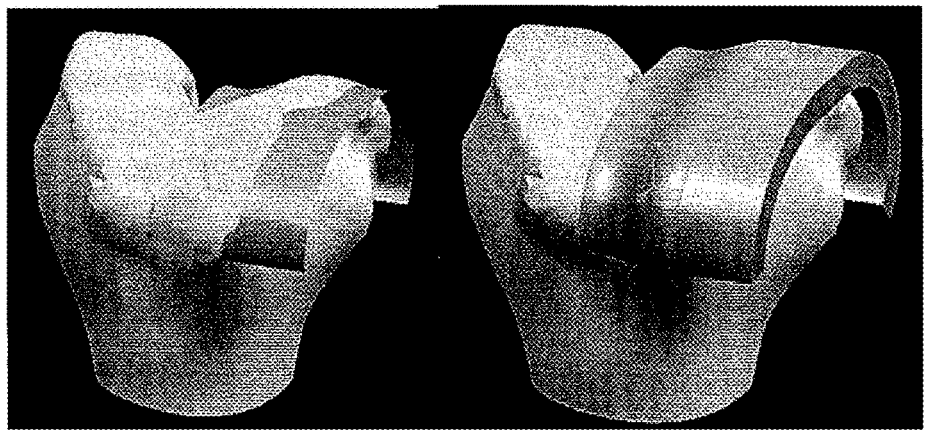

Referring to FIGS. 118-120, the side AP track is shown positioned with respect to the lateral ML track. The computer program evaluates the swath created by the cutting tool and creates the sheet body superimposed onto the distal femur with cartilage in place. In this circumstance, the sheet body provides an observer with and indication of the amount of cartilage removed as all cartilage above the sheet body would be removed. At the same time, the software program is capable of generating the solid body superimposed onto the distal femur with cartilage to show the three dimensional cutting route of the cutting tool.

Figure 121:
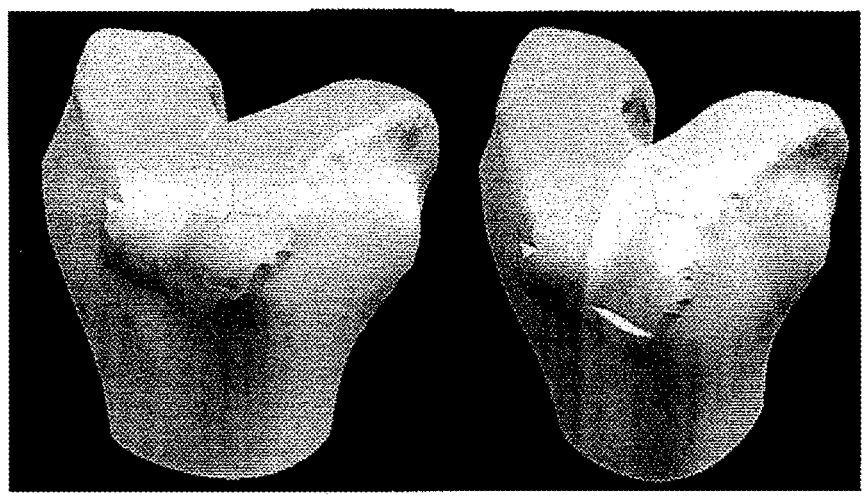
Figure 122:
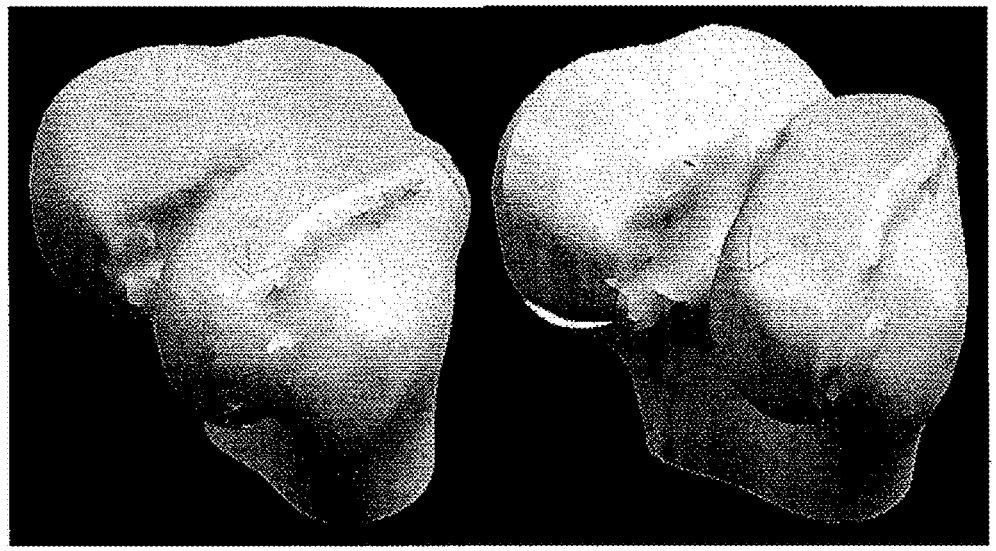
Figure 123:
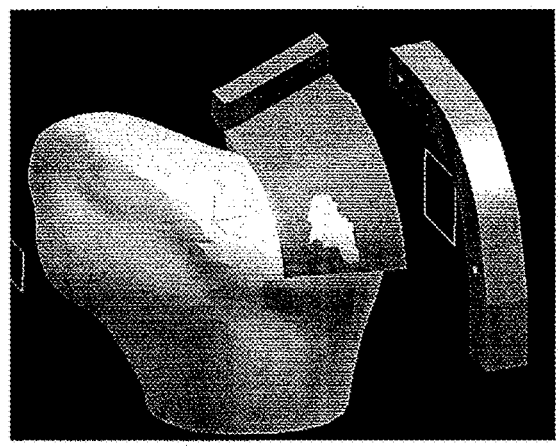
Figure 124:
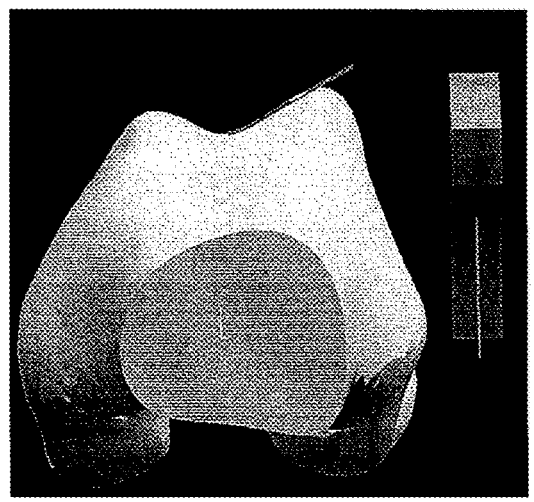
Figure 125:
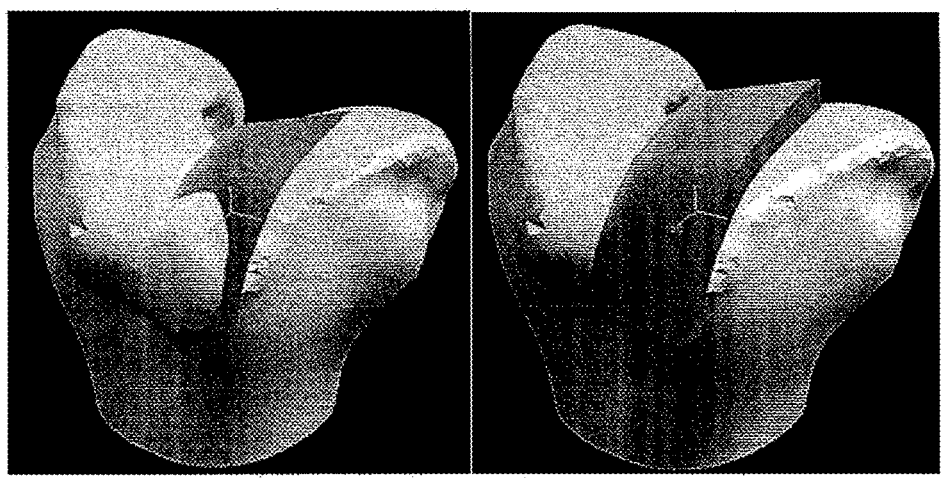
Figure 126:
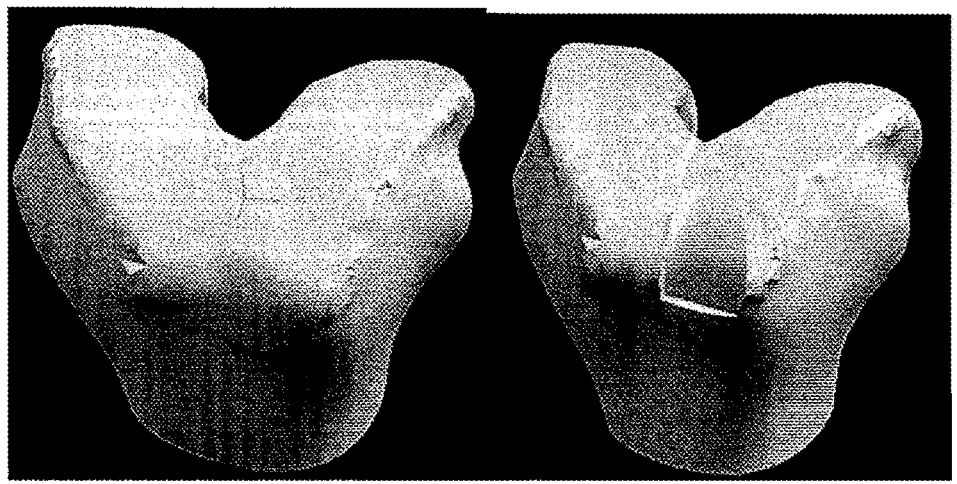

Referencing FIGS. 121 and 122, anterior and posterior views of the femur as part of the simulation carried out by the software package represent the femur with cartilage and without cartilage post cutting. As can be seen in these figures, the resulting bone is generally smooth and lacks cartilage on the bearing surfaces of the lateral condyle.

Referring to FIGS. 123-126, it was observed during the simulation that an acceptable amount of bone was gouged using the anterior ML track at a first predetermined depth. Accordingly, no additional simulation at a different cutting depth was necessary or attempted. The anterior view of the distal femur is created as part of the software package representing the femur pre and post cutting. As can be seen in this figure, the resulting bone is generally smooth and lacks cartilage on an anterior bearing surface.

Figure 127:
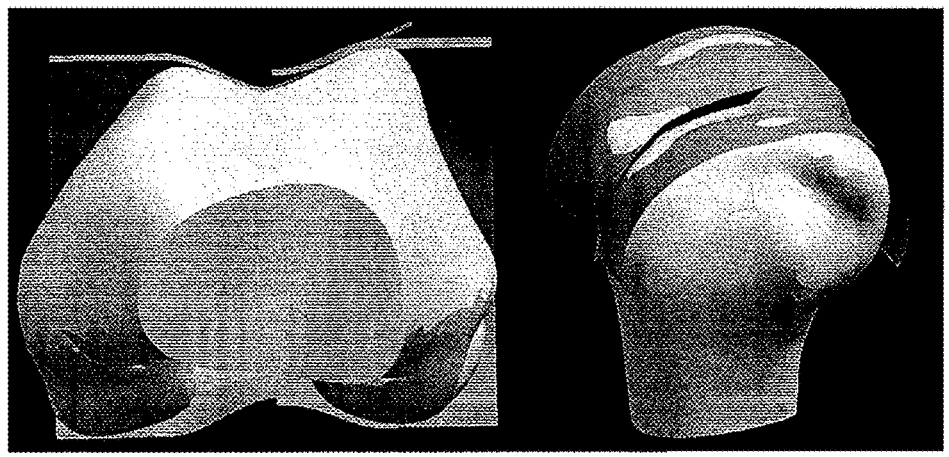
Figure 128:
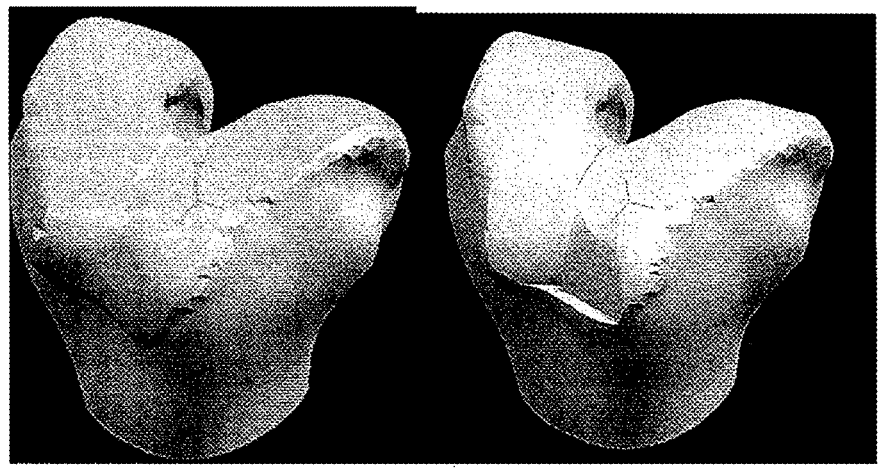
Figure 129:
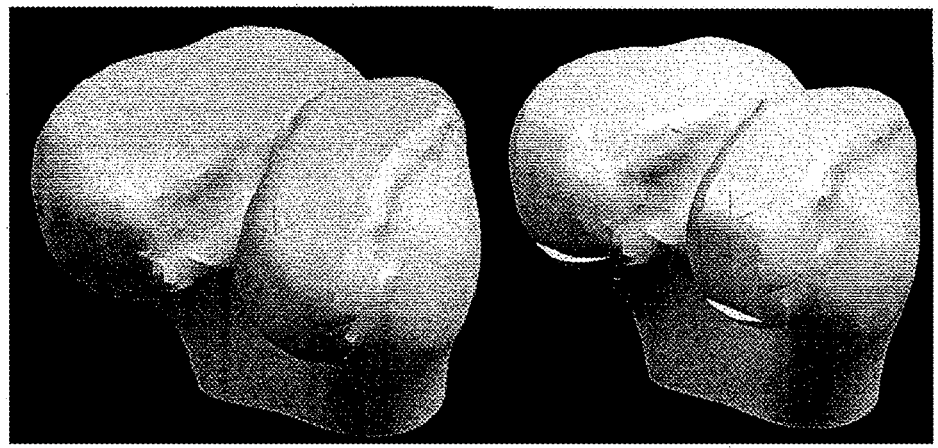

Referencing FIGS. 127-129, the software package is operative to create a femur having been cut using each of the medial, lateral, and anterior ML tracks. Overall, the combined ML tracks graze the femur in some areas. But the anterior fit is very close and all cuts come together evenly. All combined cuts cover the total area of the bearing surfaces to remove the cartilage as part of a total knee arthroplasty (TKA) procedure.

Referring back to FIG. 56 and forward to FIGS. 130 and 131, an exemplary microsurgical robot guide 252 is an advanced instrument that includes a microsurgical robot 254 that is aware of its position with respect to the distal femur 260. The microsurgical robot guide 252 makes use of the same side AP track 394 as the free form femoral cutting guide 250 to guide the microsurgical robot's 254 motion from the anterior to posterior of the femur 260. Like the free form femoral cutting guide 250, the AP track 394 is generated from the profiles of the patient's femur 260. As the microsurgical robot 254 travels over the surface of the femur in the medial-lateral direction, it adjusts its cutting depth to follow the contour of the femur, allowing the cartilage to be removed. The microsurgical robot 254 creates a cartilage resection conformal to the distal femur surface. The resulting resection is suitable for a conformal patient specific implant, which may be unilateral, bilateral, or trilateral.

Referencing FIGS. 55 and 56, preparation for using the microsurgical robot guide 252 is similar to that of the free form femoral cutting guide. Initially, a distal femur with cartilage model of the patient is obtained automatically using one or more imaging modalities such as, without limitation, CT, X-ray, and MRI. A more detailed discussion of how the distal femur with cartilage model is created from imaging modalities has been previously recited herein and will not be repeated for purposes of brevity.

As with the free form femoral cutting guide 250, the microsurgical robot guide 252 makes use of the same base 360 and positioning template 374 for securing the base onto the anterior portion of the distal femur 260. For a more detailed discussion of the base and use of the positioning template, reference is had to the free form femoral cutting guide 250 discussion. After the base 360 has been positioned, the side AP track 394 is mounted to the base, precisely as it was discussed with respect to the free formal cutting guide 250. But what is different from the free form femoral cutting guide 250 is that the microsurgical robot guide 252 obviates the need to generate separate medial, lateral, and anterior ML tracks. Instead, the microsurgical robot guide 252 includes a microsurgical robot 254 programmed with the contours of medial, lateral, and anterior ML tracks.

Referring to FIGS. 130-136, the microsurgical robot guide 252 comprises a support frame 450 that is mounted to the side AP track 394 to provide a platform for the robot 254 to translate in the ML and proximal-distal (PD) directions. The support frame 450 includes a pair of spaced apart vertical supports 452 that straddle the side AP track 394. Two dowels 454 extend between and are concurrently mounted to the vertical supports 452. In exemplary form, the dowels 454 are vertically spaced apart from one another slightly more than the vertical thickness of the side AP track 394. In this manner, the dowels 454 sandwich the side AP track 394 in the PD direction, while the vertical supports 452 sandwich the side AP track 394 in the ML direction. This four sided constraint only provides freedom of movement of the support frame 450 along the length of the side AP track 394.

In addition to the dowels 454, a rectangular elongated support 456 is concurrently mounted to the vertical supports 452. More specifically, the rectangular elongated support 456 has a constant rectangular cross-section and has a linear longitudinal dimension. In this exemplary embodiment, the elongated support 456 is mounted at one end to the first vertical support 452 to extend perpendicularly therefrom. The second vertical support 452 includes a rectangular opening through which the elongated support 456 extends. In this orientation, the elongated support 456 is perpendicular with respect to the vertical supports 452 and also perpendicular with respect to the side AP track 394. No matter how the elongated support 456 is positioned with respect to the side AP track 394, the elongated support extends perpendicularly away from the side AP track. To ensure the elongated track 456 maintains this orientation with respect to the side AP track 394, the side AP track and the support frame are fabricated from a non-elastomeric material such as, without limitation, a metal, a metal alloy, a ceramic, and a thermoset polymer. The first vertical support 452 also includes an opening 458 adapted to accommodate a control arm 460.

The control arm 460, in exemplary form, comprises a handle 464 coupled to a straight, cylindrical shaft 466. The control arm 460 is repositionable in the ML direction because the diameter of the cylindrical shaft 466 is less than the diameter of the circular opening 458 in the first vertical support 452 through which it extends. A first end of the cylindrical shaft 466 is mounted to the handle 464, which is located on a first side of the vertical support 452, while the second end of the cylindrical shaft is mounted to a robot housing 470. The robot housing 470 includes a servo motor (not shown) coupled to a rotating cutting tool 472, in this case a drill bit. The servo motor is operative to reposition the drill bit 472 in the PD direction responsive to changes in position of the drill bit with respect to the distal femur.

The location of the drill bit 472 is tracked in the AP direction via a linear cable extension transducer (not shown). The output voltage of the transducer varies as the length of cable drawn from the transducer changes. The transducer is connected to reference points on the support frame 450 and the AP track 394. As the robot 254 is translated along the side AP track 394, the output voltage of the transducer accordingly changes and the position of the robot is known. Similarly, the location of the robot 254 in the ML direction is also determined by a linear cable extension transducer (not shown). The transducer is connected to reference points on the support frame 450 and the robot housing 470. Accordingly, the robot 254 is aware of its position with respect to the distal femur 260, which allows the robot to accurately remove soft tissue with minimal effort required from the surgeon.

The cutting depth of the drill bit 472 is determined by the software package using constructed virtual 3D models of the distal femur 260 after cutting and prior to cutting with cartilage. Using the subtraction of these two models, the resultant is a 3D model of the patient's tissue to be removed with dimensions in 3D. As a result, the robot 254 is programmed to contour the underlying bone by using the three dimensional model of tissue to be removed. As discussed previously, the software package is operative to generate mediolateral contours of the distal femur 260 by rotating a plane about the TEA in increments of ten degrees. The cartilage surface points are sampled where this plane intersects the cartilage. The software package then analyses the mediolateral contours and generates a contour map of the articulating surface along with the corresponding cartilage thickness.

To use the microsurgical robot guide 252, the surgeon moves the support frame 450 with respect to the side AP track 394 to reach a starting position. Thereafter, the surgeon manipulates the handle 464 to reposition the robot housing 470 in the ML directions to remove a predetermined amount of cartilage. As the handle 464 and, thus, the robot housing 470 are repositioned in the ML direction, the robot 254 is operative to track the position of the drill bit 472 with respect to the position of the distal femur 260. In this manner, the robot 254 controls the server motor to extend the drill bit 472 to create a deeper cut and to retract the drill bit to create a shallower cut. After the surgeon has cut a ML swath, the support frame 450 is moved anteriorly or posteriorly in order for the bit 472 to make another swath and remove cartilage in the ML direction. This same process is repeated until the entire distal end of the femur is resurfaced.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. An orthopedic implant comprising:
a distal femoral component comprising a first condyle bearing surface having a first profile comprising a plurality of consecutive arcs of curvature, the number of consecutive arcs of curvature being selected based on at least an ethnic descent of a patient to customize the distal femoral component for a patient of said ethnic descent, the number of consecutive arcs of curvature being unique for each ethnic descent; and
a proximal tibial component comprising a first condyle bearing surface having a second profile comprising at least three parallel arcs of curvature.

2. The orthopedic implant of claim 1, wherein:
the first profile is comprised of only three separate arcs of curvature; and,
the distal femoral component is customized for a patient of Asian descent.

3. The orthopedic implant of claim 1, wherein:
the first profile is comprised of four separate arcs of curvature; and,
the distal femoral component is customized for a patient of African descent.

4. The orthopedic implant of claim 1, wherein:
the first profile is comprised of four separate arcs of curvature; and,
the distal femoral component is customized for a patient of European descent.

5. The orthopedic implant of claim 1, wherein the second profile is customized for a patient of Asian descent.

6. The orthopedic implant of claim 1, wherein the second profile is customized for a patient of African descent.

7. The orthopedic implant of claim 1, wherein the second profile is customized for a patient of European descent.

8. The orthopedic implant of claim 1, wherein:
the proximal tibial component further comprises a second condyle bearing surface having a third profile comprising three parallel arcs of curvature; and,
the second and third profiles are customized for a patient of Asian descent.

9. The orthopedic implant of claim 1, wherein:
the proximal tibial component further comprises a second condyle bearing surface having a third profile comprising four parallel arcs of curvature; and,
the second and third profiles are customized for a patient of African descent.

10. The orthopedic implant of claim 1, wherein:
the proximal tibial component further comprises a second condyle bearing surface having a third profile comprising four parallel arcs of curvature; and,
the second and third profiles are customized for a patient of European descent.

11. The orthopedic implant of claim 1, wherein:
the distal femoral component further comprises a second condyle having a third profile comprising at least four separate arcs of curvature;
the second and third convex profiles are each comprised of at least four separate arcs of curvature;
an anterior-posterior dimension of the implant is between 57 and 67 millimeters for a male patient of African descent; and,
a medial-lateral dimension of the implant is between 75 and 95 millimeters for a male patient of African descent.

12. The orthopedic implant of claim 1, wherein:

the distal femoral component further comprises a second condyle having a third profile comprising at least four separate arcs of curvature;

the second and third profiles are each comprised of four separate arcs of curvature;

an anterior-posterior dimension of the implant is between 57 and 67 millimeters for a male patient of European descent; and, a medial-lateral dimension of the implant is between 80 and 95 millimeters for a male patient of European descent.

13. The orthopedic implant of claim 1, wherein:

the distal femoral component further comprises a second condyle having a third profile comprising at least three separate arcs of curvature;

the second and third profiles are each comprised of three separate arcs of curvature;

an anterior-posterior dimension of the implant is between 50 and 60 millimeters for a male patient of Asian descent; and, a medial-lateral dimension of the implant is between 77 and 92 millimeters for a male patient of Asian descent.

14. The orthopedic implant of claim 1, wherein:

the distal femoral component further comprises a second condyle having a third profile comprising at least four separate arcs of curvature;

the second and third profiles are each comprised of four separate arcs of curvature;

an anterior-posterior dimension of the implant is between 50 and 65 millimeters for a female patient of African descent; and, a medial-lateral dimension of the implant is between 70 and 85 millimeters for a female patient of African descent.

15. The orthopedic implant of claim 1, wherein:

the distal femoral component further comprises a second condyle having a third profile comprising at least four separate arcs of curvature;

the second and third profiles are each comprised of four separate arcs of curvature;

an anterior-posterior dimension of the implant is between 48 and 63 millimeters for a female patient of European descent; and, a medial-lateral dimension of the implant is between 70 and 82 millimeters for a female patient of European descent.

16. The orthopedic implant of claim 1, wherein:

the distal femoral component further comprises a second condyle having a third profile comprising at least three separate arcs of curvature;

the first and second convex profiles are each comprised of three separate arcs of curvature;

an anterior-posterior dimension of the implant is between 45 and 55 millimeters for a female patient of Asian descent; and, a medial-lateral dimension of the implant is between 67 and 85 millimeters for a female patient of Asian descent.

* * * * *